(12) United States Patent
Tewhey et al.

(10) Patent No.: US 11,104,898 B2
(45) Date of Patent: Aug. 31, 2021

(54) COMPOSITIONS AND METHODS THAT ARE USEFUL FOR IDENTIFYING ALLELE VARIANTS THAT MODULATE GENE EXPRESSION

(71) Applicant: PRESIDENT AND FELLOWS OF HARVARD COLLEGE, Cambridge, MA (US)

(72) Inventors: Ryan Tewhey, Cambridge, MA (US); Pardis Sabeti, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 263 days.

(21) Appl. No.: 16/087,558

(22) PCT Filed: Mar. 24, 2017

(86) PCT No.: PCT/US2017/024076
§ 371 (c)(1),
(2) Date: Sep. 21, 2018

(87) PCT Pub. No.: WO2017/165803
PCT Pub. Date: Sep. 28, 2017

(65) Prior Publication Data
US 2019/0112594 A1 Apr. 18, 2019

Related U.S. Application Data

(60) Provisional application No. 62/313,049, filed on Mar. 24, 2016, provisional application No. 62/313,611, filed on Mar. 25, 2016.

(51) Int. Cl.
| | |
|---|---|
| C40B 30/04 | (2006.01) |
| C12N 15/10 | (2006.01) |
| C12N 15/63 | (2006.01) |
| C12Q 1/6809 | (2018.01) |
| C12Q 1/6827 | (2018.01) |

(52) U.S. Cl.
CPC ......... *C12N 15/1051* (2013.01); *C12N 15/63* (2013.01); *C12Q 1/6809* (2013.01); *C12Q 1/6827* (2013.01); *C40B 30/04* (2013.01)

(58) Field of Classification Search
None
See application file for complete search history.

(56) References Cited

U.S. PATENT DOCUMENTS

| | | |
|---|---|---|
| 5,583,009 A | 12/1996 | Palmiter et al. |
| 2007/0038386 A1 | 2/2007 | Schadt et al. |
| 2009/0215036 A1 | 8/2009 | Stropp et al. |
| 2012/0148574 A1 | 6/2012 | Brown et al. |
| 2014/0200163 A1 | 7/2014 | Mikkelsen et al. |

OTHER PUBLICATIONS

Lee, et al., "A method to predict the impact of regulatory variants from DNA sequences," Nature Genetics, Jun. 15, 2015 (Jun. 15, 2015), vol. 47, No. 8, pp. 955-961 (entire document).

(Continued)

*Primary Examiner* — Christian C Boesen
(74) *Attorney, Agent, or Firm* — Greenberg Traurig, LLP; Melissa Hunter-Ensor; Nicholas Ballor

(57) ABSTRACT

The invention features compositions and methods that are useful for identifying allele variants that modulate gene expression. Compositions and articles defined by the invention were isolated or otherwise manufactured.

15 Claims, 33 Drawing Sheets

(56) References Cited

OTHER PUBLICATIONS

Ke, X. et al., "Presence of Multiple Independent Effects in Risk Loci of Common Complex Human Diseases," American Journal of Human Genetics, Jul. 13, 2012 (Jul. 13, 2012), vol. 91, No. 1, pp. 185-192, entire document.
International Search Report and Written Opinion in corresponding PCT Patent Application No. PCT/US2017/024076, dated Jun. 16, 2017 (10 pages).

FIG. 1A 180bp Oligo synthesis  FIG. 1B Barcode addition
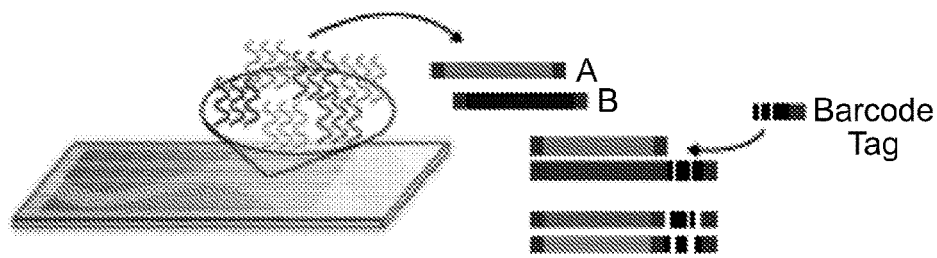
FIG. 1C Oligo assembly into an "empty" reporter vector (mpraΔorf)
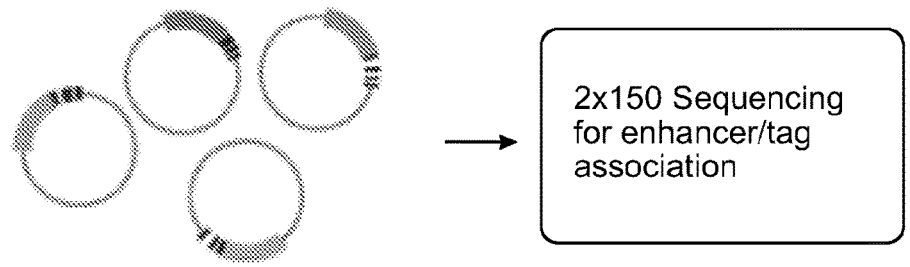
2x150 Sequencing for enhancer/tag association
FIG. 1D Insertion of GFP (mpra:gfp)  FIG. 1E Transfection
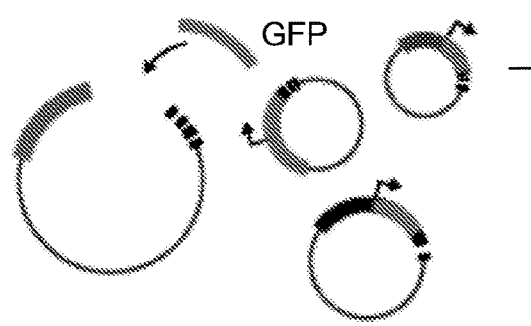
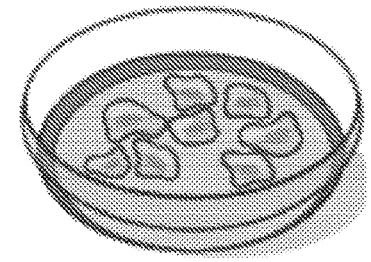
FIG. 1F GFP mRNA isolation and amplification
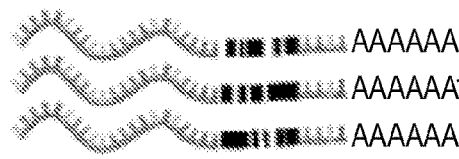
1x25 Sequencing for plasmid and mRNA tag counts
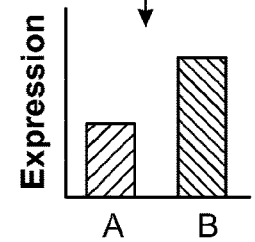

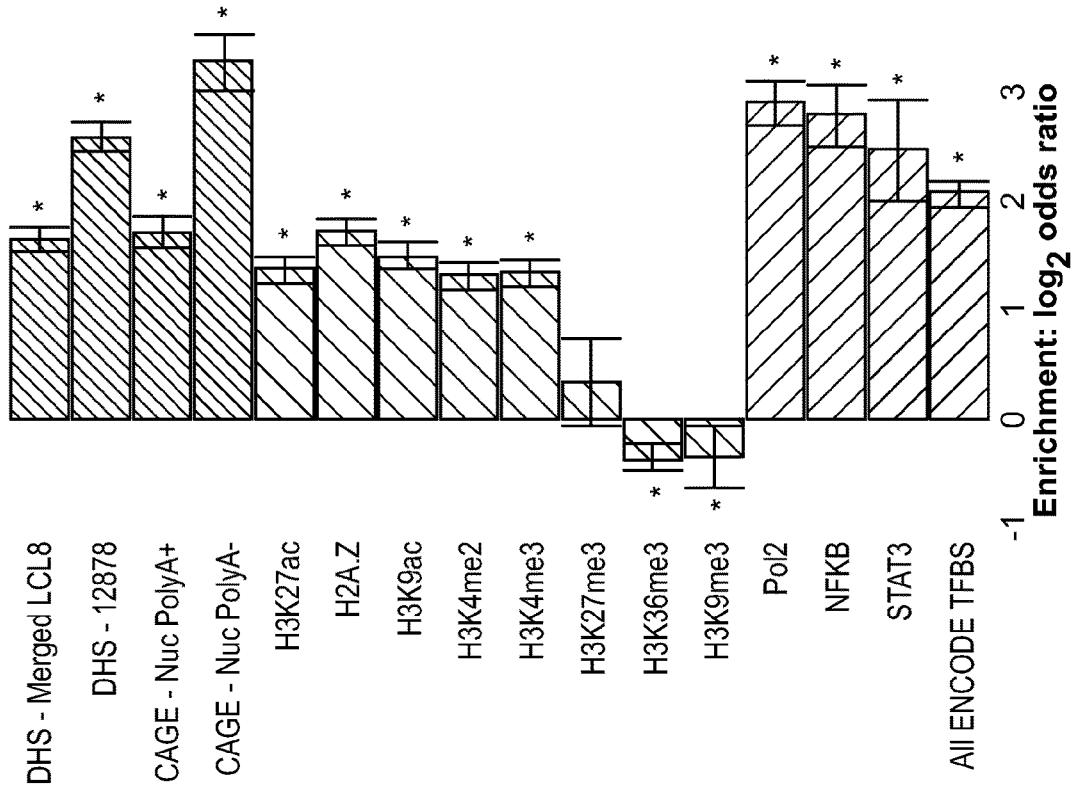
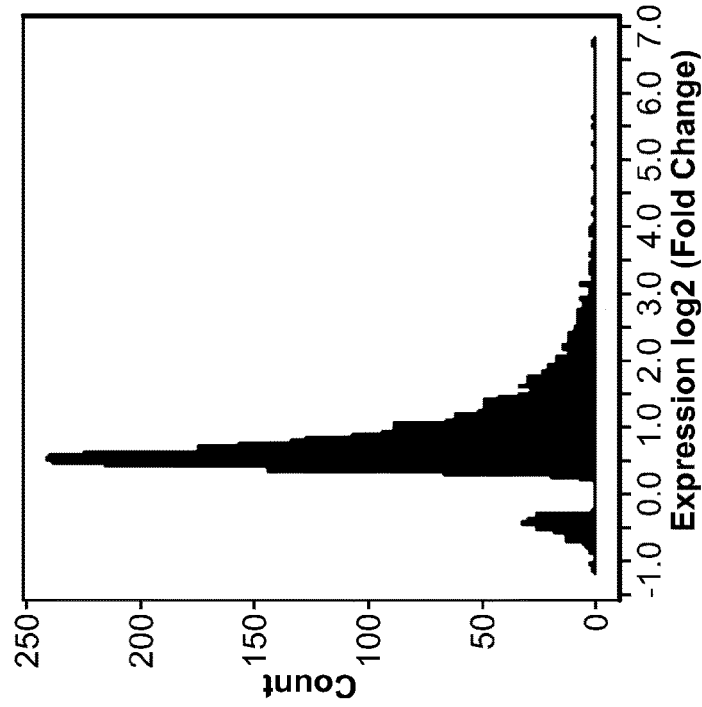
FIG. 3A
FIG. 3B

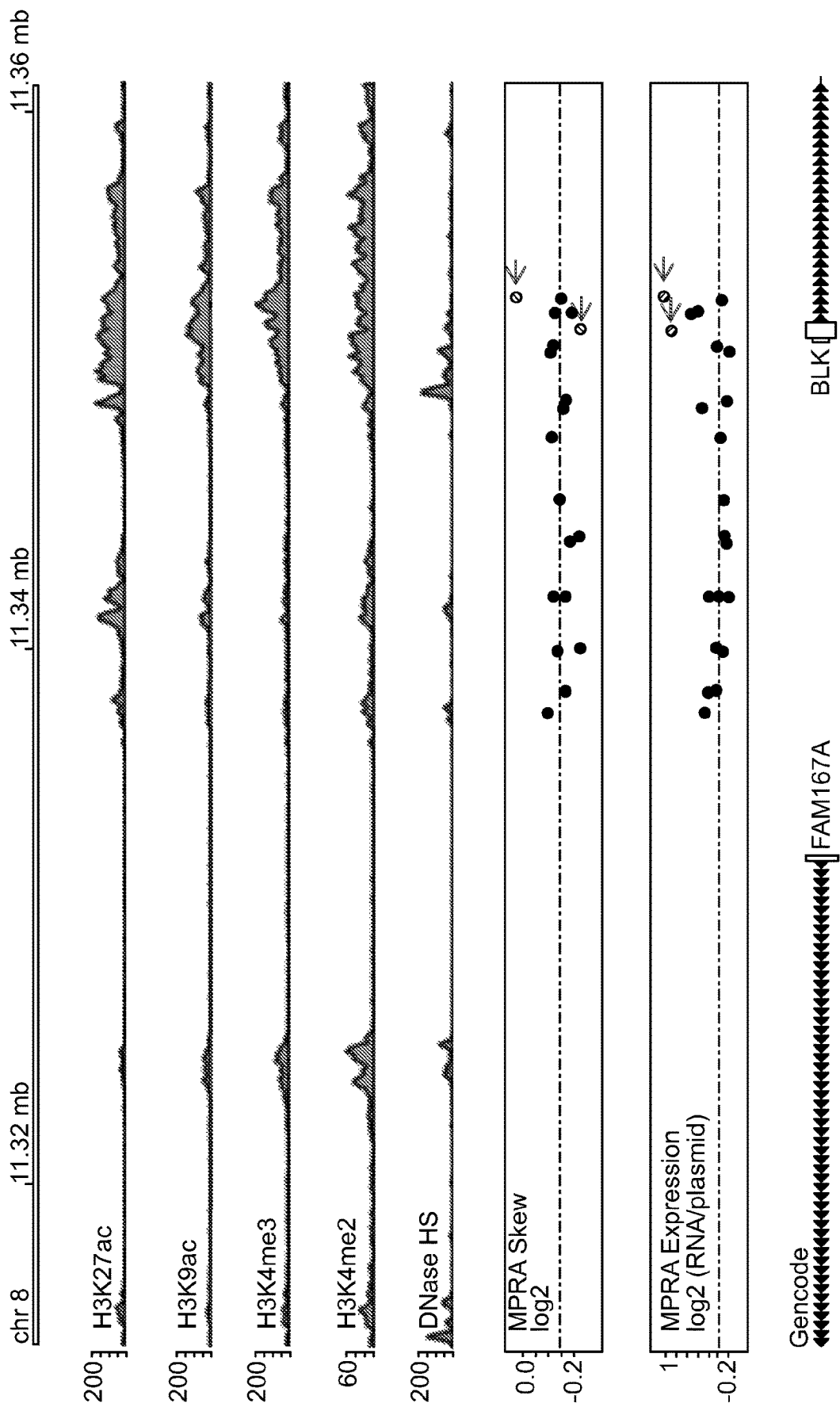

1) Standard MPRA library prep with either increased number of barcodes or the standard number of barcodes plus a unique molecular identifier positioned adjacent to the barcode 2) Transfect cells so that no cell receives the same barcode or if using a UMI there is a low probability of a repeat UMI.

3) mRNA is harvested and compared to the plasmid abundance like in traditional MPRA except individual barcodes or UMIs are compared within a single sequence element being tested ND METHODS THAT ARE
USEFUL FOR IDENTIFYING ALLELE
VARIANTS THAT MODULATE GENE
EXPRESSION

CROSS-REFERENCE TO RELATED
APPLICATION

This application is the U.S. national phase application, pursuant to 35 U.S.C. § 371, of PCT International Application Ser. No.: PCT/US2017/024076, filed Mar. 24, 2017, designating the United States and published in English, which claims the benefit of the following U.S. Provisional Application Nos. 62/313,049, filed Mar. 24, 2016, and 62/313,611, filed Mar. 25, 2016, the entire contents of each of which are incorporated herein by reference.

STATEMENT OF RIGHTS TO INVENTIONS
MADE UNDER FEDERALLY SPONSORED
RESEARCH

This invention was made with government support under Grant Nos.: DP2OD006514 and K99HG008179 awarded by the National Institutes of Health. The government has certain rights in the invention.

BACKGROUND OF THE INVENTION

The genomic era has enormously increased knowledge of human genetic variation, but understanding of the functional consequences of that variation has not kept pace. While genome-wide association studies (GWAS) and whole genome scans for natural selection have identified numerous loci linked to human traits and diseases, correlation between nearby polymorphisms (linkage disequilibrium, or LD) within individual associations often leaves dozens to hundreds of potential causal variants to be interrogated. Mounting evidence suggests that at the majority of these loci, the causal variant(s) is a non-coding regulatory change rather than an amino acid substitution. Indeed, regulatory changes drive some of the best-understood examples of phenotypic diversity and adaptive evolution. Therefore, it is critical that the question of whether a variant affects gene regulation be explored.

Current approaches for measuring a variant's effect on gene expression fall into two categories, each with its own limitation. Indirect methods, such as whole-genome epigenetic assays, can only identify the broader regulatory state of a region, not necessarily the effect of a particular variant. Direct methods, w measure the impact of individual alleles in an episomal or native context on gene expression, are currently low throughput and require substantial resources for comprehensive evaluation of a region.

SUMMARY OF THE INVENTION

The invention features compositions and methods that are useful for identifying allele variants that modulate gene expression.

In one aspect, the invention features a method of identifying a nucleic acid expression-modulating variant, the method involving introducing into a population of cells a plurality of expression vectors containing a candidate nucleic acid expression-modulating variant, an open reading frame (ORF), and an identifying randomized nucleic acid tag, wherein the ORF and the randomized nucleic acid tag is each expressed; detecting expression of the randomized nucleic acid tag; and comparing expression of the randomized nucleic acid tag with a reference level of expression, wherein detection of an alteration in expression identifies the candidate nucleic acid expression-modulating variant as a nucleic acid expression-modulating variant.

In one aspect, the invention features a method for concurrently screening a plurality of sequences to identify regulatory sequences, the method involving expressing in each cell of a population of cells a vector comprising a minimal promoter operably linked to a candidate regulatory sequence variant operably linked to a sequence encoding a detectable reporter comprising a unique randomized identifying sequence; detecting expression of the unique randomized identifying sequence; and comparing the level of the unique randomized identifying sequence expression with the expression of a control set of unique randomized identifying sequences, wherein detection of an alteration in expression identifies the candidate regulatory sequence variant as a regulatory sequence variant.

In another aspect, the invention provides a library containing a plurality of expression vectors comprising a nucleic acid expression-modulating variant, an open reading frame (ORF), and an identifying nucleic acid tag. In one embodiment, the identifying nucleic acid tag is a nucleotide barcode.

In another aspect, the invention provides a population of cells, each cell containing an expression vector comprising a nucleic acid expression-modulating variant, an open reading frame (ORF), and an identifying nucleic acid tag.

In various embodiments of the above aspects, the expression is compared with two control sets, where the first set comprises regulatory sequence variants selected randomly from the genome, and a second set containing regulatory sequence variants near but not associated with eQTL variants. In various embodiments of the above aspects, the minimal promoter directs expression at a level that is just above the limit of detection. In various embodiments of the above aspects, the variant comprises a single nucleotide variation and/or small insertion/deletion polymorphism. In various embodiments of the above aspects, the detectable reporter is luciferase or green fluorescent protein. In various embodiments of the above aspects, the identifying sequence is in the 3' untranslated region of the reporter. In various embodiments of the above aspects, the identifying sequence differentiates expression of individual oligos. In various embodiments of the above aspects, the method identifies variants that regulate genes. In various embodiments of the above aspects, the method detects differences in regulation caused by single variants within those elements. In various embodiments of the above aspects, each nucleic acid molecule is represented by an average of a thousand tags within the plurality. In various embodiments of the above aspects, the method captures the tag by hybridization. In various embodiments of the above aspects, the tag is sequenced to determine the individual oligos influencing regulation of the reporter gene. In various embodiments of the above aspects, the nucleic acid regulatory element comprises is a variant containing single nucleotide and small insertion/deletion polymorphisms. In various embodiments of the above aspects, the expression vectors are transfected into lymphoblastoid cell lines. In various embodiments of the above aspects, the method detects the over or under expression of the reporter for either the reference or alternate allele. In various embodiments of the above aspects, the method further comprises calculating the proportion of sequences that overlap open chromatin, as identified by DNase hypersensitivity sites (DHS). In various embodiments of the above aspects, the method identifies a distal enhancer. In various embodiments of the above aspects, the distal enhancer is the emVar rs9283753. In various embodiments of the above aspects, the distal enhancer regulates expression of the prostaglandin E receptor 4 (PTGER4). In various embodiments of the above aspects, the variant is a risk allele for ankylosing spondylitis. In various embodiments of the above aspects, each candidate nucleic acid expression-modulating variant is tagged with at least about 10-100 (e.g., 10, 15, 20, 25, 30, 40, 50, 60, 70, 80, 90), 100-200 (e.g., 100, 125, 150, 175, 200), or 250-500 (e.g., 250, 300, 350, 400, 450, 500) unique randomized identifying sequences. In various embodiments of the above aspects, the expression vectors are transfected into lymphoblastoid cell lines or hepatocarcinoma cell lines. In various embodiments of the above aspects, the variants are in non-coding DNA. In various embodiments of the above aspects, the method provides for the concurrent evaluation of at least about 10,000 to 100,000 (e.g., 10,000, 20,000, 30,000, 40,000, 50,000, 60,000, 70,000, 80,000, 90,000, 100,000) or 100,000 to 300,000 (e.g., 125,000, 150,000, 200,000, 250,000, 300,000) variants or more.

Compositions and articles defined by the invention were isolated or otherwise manufactured. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "plurality of expression vectors" is meant an undivided sample that contains one or more copies of at least two or more (e.g., 100, 500, 1000, 2000, 5000, 10000, or more) distinct expression vectors.

By "nucleic acid regulatory element" is meant a sequence of nucleotides which operates in part, or in whole, to regulate expression of a gene. Exemplary regulatory elements include, without limitation, promoters or cis-regulatory elements such as enhancers, silencers, boundary control elements, insulators, locus control regions, response elements, stabilizing elements, destabilizing elements and splicing elements. Such regulatory elements are, in general, but not without exceptions, located 5' to the coding sequence of the gene it controls, in an intron, or 3' to the coding sequence of a gene, either in the untranslated or untranscribed region.

By "activity of a nucleic acid regulatory element" is meant the amount of mRNA expression of an open reading frame resulting from the nucleic acid regulatory element being operatively connected to the open reading frame in the context of an expression vector. By "operatively connected" is meant that the nucleic acid regulatory element is oriented in an expression vector so as to influence the expression of the associated open reading frame.

By "nucleic acid construct" is meant an artificial (i.e., not naturally occurring) continuous sequence of nucleotides.

By "nucleic acid tag" is meant a short sequence of nucleotides (e.g., fewer than 40, 30, 25, 20, 15, 13, 12, 11, 10, 9, 8, 7, 6, 5, 4 or fewer nucleotides) included in an mRNA transcript that is unique to a particular expression vector (exclusive of the region encoding the nucleic acid tag) and/or a short sequence of nucleotides included in a nucleic acid construct that are unique to the nucleic acid construct (exclusive of the region encoding the nucleic acid tag).

By a tag "corresponding" to a particular nucleic acid element is meant that the tag is included on an mRNA sequence (or cDNA derived therefrom) that was generated under the control of the particular nucleic acid regulatory element. Because a tag "corresponds" to a particular nucleic acid regulatory element, it is possible to determine the expression vector (and, therefore, the nucleic acid regulatory element located on the identified expression vector) from which the tagged mRNA (or cDNA derived therefrom) was generated.

By "expression vector" is meant a nucleic acid that includes an open reading frame and, when introduced to a cell, contains all of the nucleic acid components necessary to allow mRNA expression of said open reading frame. "Expression vectors" of the invention also include elements necessary for replication and propagation of the vector in a host cell.

By "open reading frame" is meant a sequence of nucleotides that, when read in a particular frame, do not contain any stop codons over the stretch of the open reading frame.

By "determining the amount" is meant both an absolute quantification of a particular analyte (e.g., an mRNA sequence containing a particular tag) or a determination of the relative abundance of a particular analyte (e.g., an amount as compared to a mRNA sequence including a different tag). The phrase includes both direct or indirect measurements of abundance (e.g., individual mRNA transcripts may be quantified or the amount of amplification of an mRNA sequence under certain conditions for a certain period of time may be used a surrogate for individual transcript quantification) or both.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels."

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include ankylosing spondylitis.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2A is a scatter plot showing a correlation of normalized (Norm.) oligo counts between two transfection replicates of NA12878.

FIG. 2B is a scatter plot showing average normalized oligo counts for all five plasmid replicates compared to normalized counts for the five replicates from NA12878 RNA. Axis across all plots were kept constant with subplots added when additional datapoints were excluded from the main plot (A& B). Blue boxes within the inserts signify the displayed area of the main plots.

FIG. 2C is a scatter plot showing coefficient of variation between experimental replicates as a product of the number of barcodes tagging an oligo.

FIG. 2D is a graph showing a distribution of effect sizes (log 2 of the RNA/plasmid ratio) for oligos that were detected as being under or over expressed.

FIGS. 3A-3C show a validation of expression modifying sequences discovered by MPRA.

FIG. 3A is a graph showing a distribution of effect sizes (log 2 of the RNA/plasmid ratio) for oligos that were detected as being under or over expressed.

FIG. 3B is a box plot showing a Log 2(odds ratio) for the enrichment of regulatory annotations in the 3432 MPRA expression positive sequences within lymphoblastoid cell lines (LCLs) relative to expression negative sequences.

FIG. 3C is a box plot showing a Log 2(odds ratio) for the enrichment in LCL DNase hypersensitivity sites (DHS) sites for expression positive sequences shared between LCLs and HepG2s (left most box), expression positive in only LCLs (middle) and expression positive in only HepG2 cells (right most box). Asterisk: fisher's test p-value <0.01.

FIG. 4A is a graph that includes a distribution of expression strength (x-axis) and allelic skew (y-axis) for all 29 k variants.

FIG. 4B is a graph that shows the cumulative distribution of the absolute difference of the log 2 fold change between the reference and alternate allele for emVars, expression positive variants that were not detected as emVars and all other variants.

FIG. 4C is a scatter plot showing allelic skew as measured by MPRA for 127 positive controls values discovered in the original 79 k library (x-axis) that were tested in the 7.5 k library (y-axis).

FIG. 4D is a scatter plot showing a comparison of allelic skew as estimated from the mean of 2 independent LCLs (NA12878 & NA19239). Red points in both plots denote variants called as emVars from the joint LCL analysis. Correlation is provided as Pearson's R.

FIG. 5A is a graph showing MPRA skew estimates for LCL emVars with transcription factor (TF) motif/ChIP annotations compared to the predicted change in binding between the two alleles.

FIG. 5B is a graph showing a comparison between skew seen in MPRA and that in DHS for all emVars passing stringent filters for high-confidence DHS skew sites (methods). Skew is calculated as log 2(Alt-allele counts/Ref allele counts).

FIG. 5C is a graph showing the proportion of EUR expression quantitative trait loci (eQTLs) explained by an emVar plotted against the difference in variance explained between the top variant and the second strongest association in the EUR eQTL analysis. grey line: all emVars, solid line: annotation positive emVars, dashed line: annotation negative emVars.

FIG. 5D is a Ven diagram showing proportion of variants by their MPRA classification that fall in an ENCODE transcription factor (TF) ChIP-seq peak and contain the predicted motif. Variants are binned according to the difference in predicted binding strength between the two alleles. (For multiple TF associations, the one with the largest delta is used).

FIG. 5E is a graph showing overlap between annotation-positive sites (methods), sequences detected as regulatory by MPRA and emVars. All Correlations are provided as Pearson's R.

FIG. 6A-6I shows emVars associated with ankylosing spondylitis and systemic lupus erythematosus.

FIG. 6A is a graph showing a plot of the PTGER4 locus which overlaps a GWAS peak for ankylosing spondylitis displaying ChIA-PET and ENCODE annotations (top 6 tracks), observed allelic skew (track 7) and expression strength (track 8) from MPRA. Significant variants for expression (bottom arrow) and skew (top arrow) in the MPRA; others were: non-significant.

FIG. 6B is a box plot showing MPRA expression values of the PTGER4 variant rs9283753 in LCL's normalized to the plasmid library. Plasmid control is furthest left in Ref and Alt. NA12878 is in the middle. NA19239 is at the right in Ref and Alt.

FIG. 6C provides an analysis of LCL eQTL results in EUR and YRI populations for the PTGER4 with rs9283753.

FIGS. 6D and 6E are box plots showing (D & E) PTGER4 expression as measured by qPCR for two LCL's that underwent allelic replacement at rs9283753.

FIG. 6F provides plots of the FAM167A-BLK locus associated with systemic lupus erythematosus. Significant variants for expression (bottom arrow) and skew (top arrow) in the MPRA; others were: non-significant.

FIG. 6G provides a box plot of MPRA expression values of the chr8:11353110 deletion variant in LCL's normalized to the plasmid library. Plasmid control is furthest left in Ref and Alt. NA12878 is in the middle. NA19239 is at the right in Ref and Alt.

FIGS. 6H and 6I plot LCL eQTL results in EUR and YRI populations for the FAM167A and BLK associations.

FIG. 7A shows a coefficient of determination of normalized oligos counts between all replicates.

FIG. 7B shows correlation of counts for oligo with values of 7500 or less demonstrating the difference between replicates are largely driven by highly expressed sequences.

FIG. 8A is a graph showing unnormalized mean reads from the sum of all barcodes counts for the five plasmid replicates and the 13 experimental samples.

FIG. 8B is a graph showing the effect of barcode abundance on the oligo mean. The 79 k MPRA library was downsampled to select the specified number of barcodes for each oligo. Barcodes were summed to obtain oligo counts for normalization in DESeq. Replicates for NA128 78 were averaged and compared to oligo counts calculated from all barcodes.

FIG. 9A provides bar plots of the number of barcodes tagging each oligo for the initial 79 k MPRA library and the 7.5 k libraries at before and after downsampling.

FIG. 9B provides bar plots for of the base mean value and dispersion (variance) as estimated in DESeq2 for the 79 k MPRA library and the 7.5 k library using all barcodes and a downsampled subset.

FIGS. 9C and 9D are plots showing effect sizes from 7.5 k MPRA experiment for expression and (D) skew effect sizes of positive and negative control variants from the downsampled 7.5 k library.

FIG. 9E is a graph showing log 2 fold change of oligo expression in RNA data plotted against the normalized abundance of each oligo in the plasmid library for the combined LCL analysis.

FIG. 10A is a scatter plot showing a comparison of allelic skew as estimated from the mean of 2 independent LCL experiments. Points indicated were called in the joint LCL analysis. Shaded points represent variants called significant when analyzing only NA12878 but failed to reach significance in the joint analysis.

FIGS. 10B and 10C are graphs showing Z-score qq-plots of the expression differences between alleles. Differences between n log ratios of the reference and alternate allele were converted to z-scores for each oligo pair using all sequence in (B) NA12878 and (C) NA19283.

FIGS. 10D and 10E are graphs showing q q-plots of p-values from the allelic skew t-test at non-expressed sequences. Ref/alt pairs in (D) NA12878 and (E) NA19283 were considered not expressed if both oligos had uncorrected expression p-values of 0.05 or greater.

FIG. 11A-1C show correlation of MPRA allelic skew with existing datasets. (A & B) Correlation of skew in TF binding with skew on the MPRA.

FIG. 11A is a scatter plot. Plotted are all emVars that passed stringent filters for high-quality transcription factor binding sites demonstrating allelic skew (supplemental methods) with MPRA allelic skew FDR<0.05, and with DHS skew P<0.1. For variants that were overlapped by multiple transcription factors binding sites, we picked the transcription factor with the most statistically significant skew. Skew is calculated as log 2(Alt−allele counts/Ref−allele counts) and correlation is provided as Pearson's R.

DETAILED DESCRIPTION OF THE INVENTION

Figure 2B:
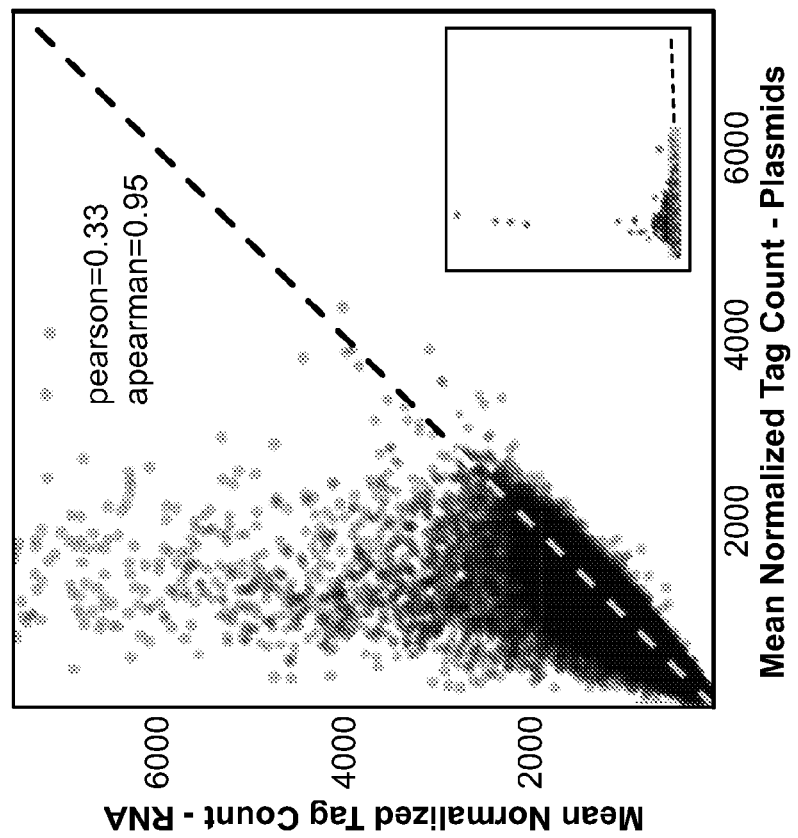
FIG. 2A-2D shows an analysis of experimental reproducibility.
Figure 2A:
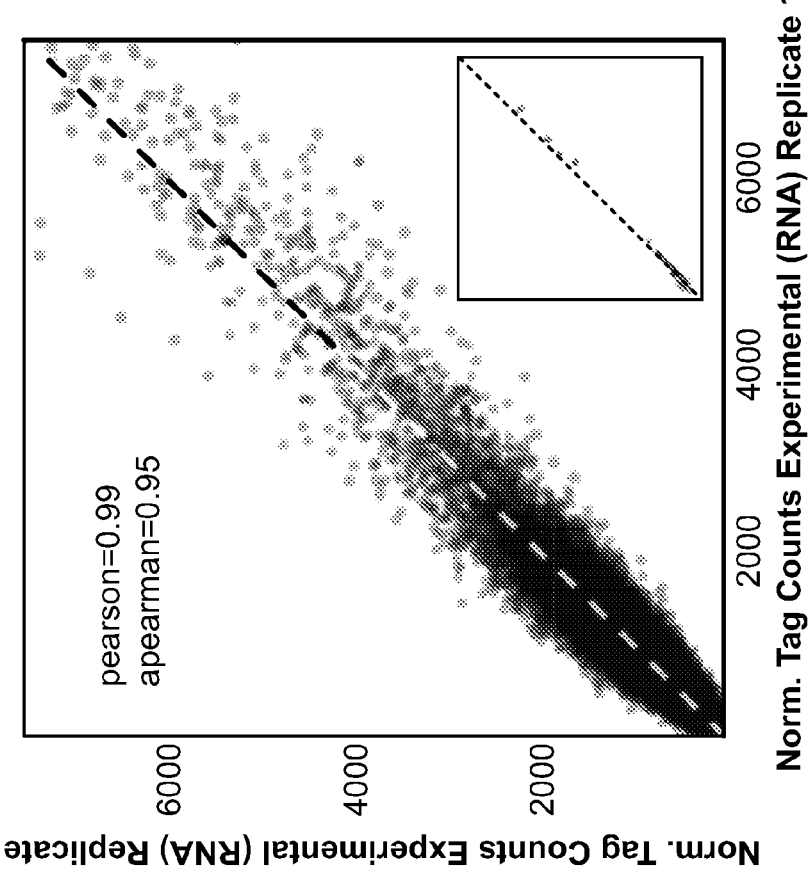

The invention features compositions and methods that are useful for identifying allele variants that modulate gene expression.

Although studies have identified hundreds of loci associated with human traits and diseases, pinpointing causal alleles remains difficult, particularly for non-coding variants. To address this challenge, the massively parallel reporter assay (MPRA) was modified to identify variants that directly modulate gene expression. This technique was used to characterize 29,000 variants from 3,965 cis-expression quantitative trait loci. A strong correlation was discovered with measures of regulatory function, a sensitivity of ~20% and a positive predictive value of 60-65% to detect the causal allele. 842 variants showing differential expression between alleles, including 53 well annotated variants associated with diseases and traits, were identified. One of these was investigated in detail, a risk allele for ankylosing spondylitis. This analysis provided direct evidence of a non-coding variant that alters expression of the prostaglandin EP4 receptor. A resource of concrete leads was created, which illustrates the promise of this approach for comprehensively interrogating how noncoding polymorphism shapes human biology.

Massively Parallel Reporter Assay

The MPRA assay was modified to permit the large-scale, sensitive and direct testing of potential regulatory variants. This assay is based upon the well established reporter gene assay, in which a vector containing a reporter gene (e.g. luciferase or green fluorescent protein (GFP)), a promoter and a potential regulatory sequence is inserted into a plasmid, which is transfected into a cell; sequences that regulate gene expression then alter the amount of luciferase/GFP expressed. Through the use of unique barcodes in the 3' untranslated region (UTR) of the reporter to differentiate expression of individual oligos, MPRA can test many different sequences simultaneously, and it has been shown to reproducibly detect segments of the genome that change expression levels. An aim of this work was to incorporate single nucleotide and small insertion/deletion polymorphisms, (referred to below as single nucleotide variants or SNVs), into these assays, to see if the assay could detect subtle differences in how each allele drives expression. Because only a minimal promoter with very low baseline expression was used in this iteration of the assay, this approach identifies regulatory sequences that increase (i.e. enhancers and promoters), rather than decreases, expression; the latter will be difficult to detect, since baseline expression is already low.

Ideally, one would test the assay for sensitivity and specificity by applying it to a set of 'gold-standard' variants previously identified as expression quantitative trait loci (eQTLs) that act on enhancer and promoter elements. However, there is a dearth of such known variants. As the best available alternative, a set of thousands of candidate eQTL variants in regions associated with differential gene expression in the population was studied.

There are important considerations in interpreting the results of such a test. First, multiple candidate variants were tested (sometimes dozens) within each eQTL region that are in linkage disequilibrium with one another. It was generally expected that at most one of these variants will be causal, and sometimes the true causal variant will not appear in the set, because the degree of linkage disequilibrium falls below the cutoff used for inclusion. For these reasons only a minority of the variants tested were expected to give a signal in the MPRA assay. Conservative estimates suggested that in 34-41% of eQTL peaks (dependent on the population tested), the causal variant will be the top associated allele. Second, only a subset of the true variants responsible for eQTLs (23-64%, according to recent estimates) will act on enhancers or promoters, which are the functional classes that will be detected in the MPRA assay. Variants that work by other processes, such as microsatellites or post-transcriptional regulation, would not be captured or expected to score.

The specificity, sensitivity and reproducibility of MPRA to localize causal alleles within large genomic loci linked to variation in gene expression was estimated. In addition, genome wide association studies (GWAS) loci that overlap with eQTLs were comprehensively interrogated to identify and characterize potential regulatory variants underlying human diseases and traits.

Accordingly, the invention provides expression vectors, cells, constructs, kits, systems, and methods for determining qualitative or quantitative activities or both of a plurality of nucleic acid regulatory elements which have been distinctively tagged. Such activity of the tagged regulatory element is assayed at, e.g., the transcriptional level. The methods described herein facilitate, e.g., the systematic reverse engineering or optimization of cis-regulatory elements at high resolution and at a large scale. Exemplary cis-regulatory elements include, without limitation, elements functional in plants, bacteria, animals (e.g., humans), protists, and fungi. The methods further include integration of multiplexed DNA synthesis and sequencing technologies to generate and quantify the transcriptional regulatory activity of such cis-regulatory elements, e.g., thousands of arbitrary DNA sequences in parallel in cell-based assays (e.g., mammalian cell-based assays).

Briefly, tens of thousands of oligonucleotides encoding the regulatory element of interest, and a set of engineered variants, are obtained (e.g., by parallel synthesis on a microarray). Each variant is linked to one or more distinct tags, as well as several common restriction and/or primer sites that facilitate amplification and cloning. These variants are then PCR amplified and cloned in parallel into an arbitrary expression vector (e.g., a bacterial, yeast, or mammalian expression vector). A constant fragment containing an arbitrary open reading frame (ORF) (e.g., a fluorescent protein such as green fluorescent protein ("GFP") or luciferase) and optionally a promoter is then inserted between the regulatory elements and their associated tags. In some examples, distinct plasmids are maintained as an undivided single high complexity library.

To assay the relative transcriptional activities of the regulatory elements, the plasmids are co-transfected into a population of cultured cells. In some examples, cells containing plasmids, fragments of plasmids, or plasmid-derived viral or transposon vectors that have been stably integrated into the genome are selected based on drug resistance (e.g., puromycin resistance) or fluorescence (e.g., GFP expression). After optional perturbations of the cell population, the cells may be harvested for total RNA and/or poly(A)+RNA isolation. Optionally, first strand cDNA synthesis may be performed and an cDNA library (e.g., an cDNA library) may be generated using fusion PCR or ligation. Optionally, the cDNA synthesis may include addition of one or more distinct nucleic acid tags to all synthesized molecules that may serve to identify the cell population or sample from which the library was generated. The mRNA or cDNA containing individual tags may then be quantified (e.g., by quantitative sequencing, microarray hybridization, or bead hybridization) representing the relative abundances of mRNAs transcribed from each distinct reporter construct in the experiment. To normalize for differences in the relative concentrations of the transfected plasmids, similar tag counts may be generated by sequencing the plasmid pool or the all or part of the genomes of stable transfected cells. Finally, the relative activities of the various regulatory element variants may be inferred from the set of normalized tag counts using a statistical algorithm. For example, the activity of a single regulatory element variant linked to a single tag is first estimated by dividing the sequence count or hybridization signal of the tag in the mRNA or cDNA sample to the corresponding sequence count or hybridization signal of the same tag in the corresponding plasmid pool. If the plasmid pool contains multiple distinct constructs that link the same regulatory element variant to different tags, a more accurate estimate of the activity of the element may optionally be obtained by computing a summary statistic (e.g., the median or mean) of the mRNA or cDNA to plasmid ratios obtained for each individual tag. The relative activities of each distinct regulatory element may then be inferred by comparing these normalized sequence count or hybridization signals.

In certain embodiments, nucleic acid constructs including restriction enzyme sites ("R" and "E"), a tag, and 15 base universal tails are engineered. The construct is amplified using PCR and universal primers. The resultant construct mixture is then inserted into an expression vector generating a plasmid library. The plasmids are digested and an ORF (e.g., a sequence encoding a GFP) is inserted into the expression vector. The plasmids are then transfected into a cell population, first strand cDNA synthesis is then performed, and the tags are quantified according to standard methods, e.g., quantitative sequencing protocols.

Briefly, tens of thousands of oligonucleotides encoding a tag followed by a regulatory element of interest, and a set of engineered variants, are obtained (e.g., by parallel synthesis on a microarray). Each variant is linked to one or more distinct tags. These variants are then, e.g., PCR amplified and cloned in parallel into an arbitrary expression vector (e.g., a bacterial, yeast, or mammalian expression vector) downstream of an arbitrary ORF (e.g., a fluorescent protein such as GFP or luciferase) (the ORF optionally being downstream of an additional regulatory element). In some examples, distinct plasmids are maintained as an undivided single high complexity library. The relative transcriptional activities of the different expression vectors can be determined, e.g., as described above.

In yet another exemplary method, a short, very high-complexity tag pool (e.g., generated by degenerate column-based oligonucleotide synthesis) is cloned into a reporter background (e.g., an expression vector containing an arbitrary ORF). Various regulatory elements are then cloned into the tagged plasmid pool. The various regulatory elements can be generated, e.g., by multiplexed PCR, error-prone PCR, or shearing/digestion of genomic DNA. Variant-tag links can be established by pair-end sequencing of the resultant pool or by digestion of the plasmid library to remove all or a portion of the nucleotides between the regulatory element and tags, followed by sequencing. The relative transcriptional activities of the different expression vectors can be determined, e.g., as described above.

Nucleic acid constructs are generated by any means known in the art, including through the use of polymerases and solid state nucleic acid synthesis (e.g., on a column, multiwall plate, or microarray). Furthermore, a plurality of nucleic acid constructs may be generated by first generating a parent population of constructs (e.g., as described above) and then diversifying the parent constructs (e.g., through a process by which parent nucleotides are substituted, inserted, or deleted) resulting in a diverse population of new nucleic acid constructs. The diversification process may take place, e.g., within an isolated population of nucleic acid constructs with the nucleic acid regulatory element and tag in the context of an expression vector, where the expression vector also contains an open reading frame operatively connected to the nucleic acid regulatory element.

The nucleic acid regulatory elements may be naturally-occurring sequences, variants based on the naturally-occurring sequences, or wholly synthetic sequences. The source of the nucleic acid regulatory element is not critical. Variants include those developed by single (or greater) nucleotide scanning mutagenesis (e.g., resulting in a population of nucleic acid regulatory elements containing single mutations at each nucleotide contained in the naturally-occurring regulatory element), transpositions, transversions, insertions, deletions, or any combination thereof. The nucleic acid regulatory elements may include non-functional sequences (e.g., sequences that create space between nucleic acid regulatory subunits but do not themselves contribute any sequence specific effect on the regulatory element's activity). In other embodiments, the regulatory element is entirely arbitrary, and genetic reporter constructs are constructed that link such arbitrary DNA elements to distinguishing tags as described below.

The invention provides for the inclusion of nucleic acid tags to facilitate the determination of the activity of specific nucleic acid regulatory elements. These tags are included in the nucleic acid constructs and expression vectors containing the nucleic acid regulatory elements. Each tag is unique to the corresponding nucleic acid regulatory element (i.e., although a particular nucleic acid regulatory element may have more than one tag (e.g., 2, 3, 4, 5, 10, or more), each tag is indicative of a single nucleic acid regulatory element). These tags are oriented in the expression vector such that they are transcribed in the same mRNA transcript as the associated open reading frame. The tags may be oriented in the mRNA transcript 5' to the open reading frame, 3' to the open reading frame, immediately 5' to the terminal poly-A tail, or somewhere in-between.

The nucleic acid tags may be greater than 4 (e.g., greater than 10) nucleotides in length and/or fewer than 40, 30, 25, 20, 15, 13, 12, 11, 10, 9, 8, 7, 6, 5, or 4 nucleotides in length (e.g., the tags may be 5, 6, 7, 8, 9, 10, 11, 12, 13, 14, or 15 nucleotides in length). The unique portions of the nucleic acid tags may be continuous along the length of the tag sequence or the tag may include stretches of nucleic acid sequence that is not unique to any one tag. In one application, the unique portions of the tags may be separated by a stretch of nucleic acids that is removed by the cellular machinery during transcription into mRNA (e.g., an intron).

The expression vectors include a nucleic acid regulatory element, an open reading frame, and a nucleic acid tag. These elements may be arranged in a variety of configurations. For example, the nucleic acid regulatory element may be 5', 3', or within the open reading frame. The nucleic acid tag may be located anywhere within the region to be transcribed into mRNA (e.g., upstream of the open reading frame, downstream of the open reading frame, or within the open reading frame). Importantly, the tag is located 5' to the transcription termination site. The expression vectors may also include additional elements (e.g., invariant promoter elements (e.g., a minimal mammalian TATA box promoter or a synthetic inducible promoter), invariant or low complexity regions suitable for priming first strand cDNA synthesis (e.g., located 3' of the nucleic acid tag), elements to aid in isolation of transcribed RNA, elements that increase or decrease mRNA transcription efficiency (e.g., chimeric introns) stability (e.g., stop codons), regions encoding a poly-adenylation signal (or other transcriptional terminator), and regions that facilitate stable integration into the cellular genome (e.g., drug resistance genes or sequences derived from lentivirus or transposons).

The plurality of expression vectors includes an undivided sample containing one or more copies of at least two or more (e.g., 100, 500, 1000, 2000, 5000, 10000, or more) distinct expression vectors. Each distinct expression vector in the plurality of expression vectors differs from the remaining expression vectors by the inclusion of an identifying nucleic acid tag and, optionally, a distinct nucleic acid regulatory element. For example, each expression vector may share any or all of the following: one or more open reading frames, one or more invariant promoter element (e.g., a minimal mammalian TATA box promoter), one or more invariant or low complexity regions suitable for priming first strand cDNA synthesis (e.g., located 5' or 3' of the nucleic acid tag), one or more elements to aid in isolation of transcribed RNA, one or more elements that increase or decrease mRNA transcription efficiency (e.g., chimeric introns) or stability (e.g., stop codons), regions encoding a poly-adenylation signal (or other transcriptional terminator), and regions that facilitate stable integration into the cellular genome (e.g., drug resistance genes or sequences derived from lentivirus or transposons) The regulatory elements and tags of the plurality of expression vectors may differ from each other, e.g., as described herein.

The tags are quantified by methods known in the art, including quantitative sequencing (e.g., using an Illumina® sequencer) or quantitative hybridization techniques (e.g., microarray hybridization technology or using a Luminex® bead system).

The invention provides multiple rounds of reporter assays to be performed where the variant sequences tested in one round are designed based on information gleaned from the previous round. Therefore, the invention also provides a strategy for systematically reverse engineering cis-regulatory elements and for iteratively developing and refining novel synthetic cis-regulatory elements.

In one embodiment, a regulatory element of interest is systematically mutated at every position to reveal the location of subsequences that are critical for the activity of the element. The method may also include identifying regulatory subsequences by mutating multiple consecutive nucleotides in each variant, thereby uncovering weak binding sites. Second, a new series of variants may then be synthesized to probe for constraints on the relative spacing, order, and orientation of the identified regulatory subsequences. The data from these two rounds may be used to develop a qualitative model of the regulatory element. Additional rounds of assays may then be performed to iteratively test and refine the model. This method may be applied to study a large number of distinct regulatory elements in parallel. In order to construct physical models of the regulatory element, the biochemical properties and protein-DNA interactions of the critical subsequences identified in this assay may be further studied using standard methods for studying individual protein-DNA interactions, such as high-throughput systematic evolution of ligands by exponential evolution enrichment (HT-SELEX) and mechanically induced trapping of molecular interactions (MITOMI).

The invention also provides kits for performing the methods of the invention. Such kits may include expression vectors, cells, nucleic acid constructs containing open reading frames, restriction enzymes, reaction buffers, and instructions for performing the methods described herein.

The invention also provides systems for performing the methods of the invention. Such systems include combinations of the following: populations of the above-described cells, reagents for isolating mRNA generated from such a population of cells, reagents for performing first strand cDNA synthesis using the isolated mRNA as a template, and a device for quantitatively sequencing the cDNA products.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Adapting MPRA to Test ~30 k Candidate Variants

The massively parallel reporter assay (MPRA) was modified to increase throughput while also improving its reproducibility and sensitivity (FIG. 1, Experimental Procedures); the latter is important since the goal of this technique is not merely to find genetic elements that regulate genes, but to detect differences in regulation caused by single variants within those elements. To accommodate the large library size and to increase the sensitivity of the assay, 20 bp nucleotide barcodes were added to the oligos by emulsion PCR, thus allowing each oligo to be represented by an average of a thousand tags within the plasmid library. Post transfection, the GFP mRNA was captured by hybridization and Illumina sequencing of the UTR barcode was performed to determine the individual oligos influencing regulation of the reporter gene. This new experimental approach decreased inter-experimental noise and allowed the application of a parametric statistical framework during analysis.

Example 2: Selection of Variants Tested

For benchmarking and discovery, nearly thirty thousand single nucleotide variants (SNVs) were first examined within a set of eQTLs. eQTLs were identified from the Geuvadis RNA-seq dataset of lymphoblastoid cell lines (LCLs) from individuals of European (EUR) and West African (YRI) ancestry due to the availability of both genome sequences and immortalized cell lines for these individuals. For each of the 3,642 eQTLs, there was designed and synthesized DNA oligonucleotides (oligos) representing the top associated variant and all variants in perfect LD with it. This approach selects an average of 3 SNVs per eQTL peak. As noted above, it was expected that (i) this 129 set will often fail to contain the true causal variant, and (ii) when the set does contain the causal variant, the other two variants will not be causal. This approach included 209 eQTLs that overlapped GWAS hits for deeper investigation; for these, all alleles in moderately strong LD ($r2>=0.9$) with the lead variants were tested. After inclusion of several smaller sets of variants, and accounting for neighboring variants and orientation of the variant when associated with multiple genes, this first 79 k oligo library included 39,479 oligo pairs, originating from 29,173 unique variants.

A second MPRA experiment was performed that assayed 264 positive control variants (sites identified in the first 79 k MPRA library) and 3200 negative control variants. The negative controls included 2700 variants chosen at random across the genome matching the minor allele frequency distribution of the larger 79 k library. To select a set of negative control variants with a similar biological profile, 500 SNVs were included that were in close proximity to an eQTL peak (within 250-1000 bp) and not in LD with the lead variant. All variants were incorporated into a 7.5 k oligo library. In total, across the two experiments 85,358 oligos (42,679 reference/alternate pairs) were evaluated, centering the variant of interest in 150 bp of its genomic sequence.

Figure 2C:
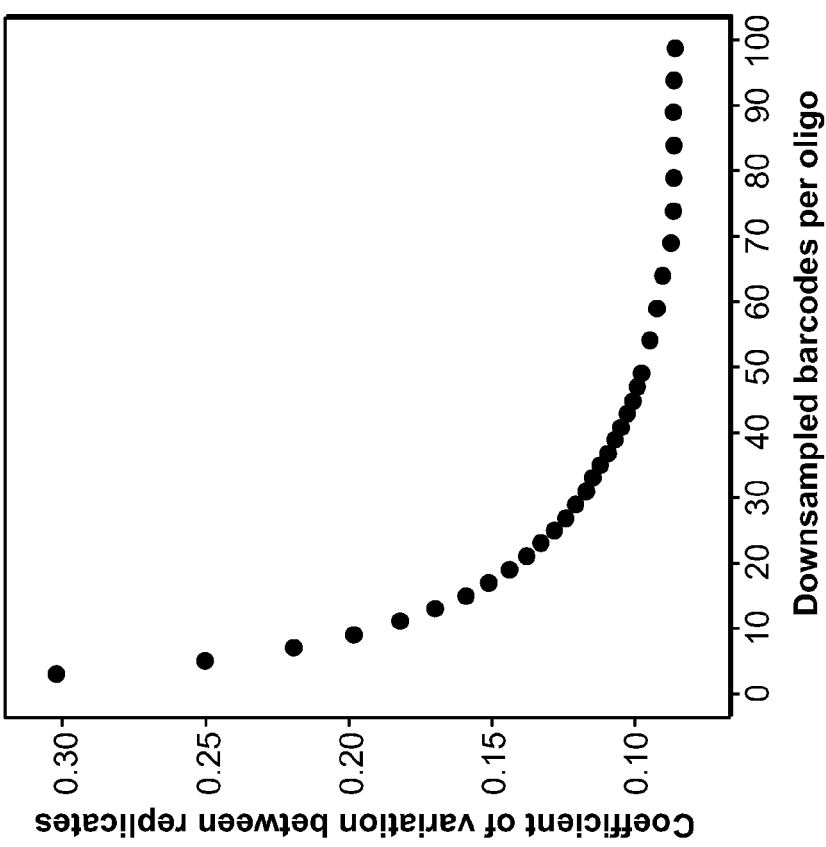

The original 79 k MPRA library was transfected into two separate lymphoblastoid cell lines (NA12878 & 117 NA19239) from the 1000 Genomes (1000G) project as well as into a hepatocarcinoma cell line 118 (HepG2). Eight and five technical replicates for the lymphoblastoid and hepatocarcinoma cell lines were performed, respectively. High coverage and excellent reproducibility in the assay was observed, capturing 98.4% of the 79K oligos tested at a depth of 20 reads or greater. Reproducibility was excellent between experimental replicates of identical cell lines, with an average correlation of 0.99 (FIGS. 2A and 2B, and 7A and 7B) and expression values were strongly correlated with a traditional single-plexed luciferase assay for the 29 sequences examined (R=0.84, FIG. 2C).

Figure 8A:
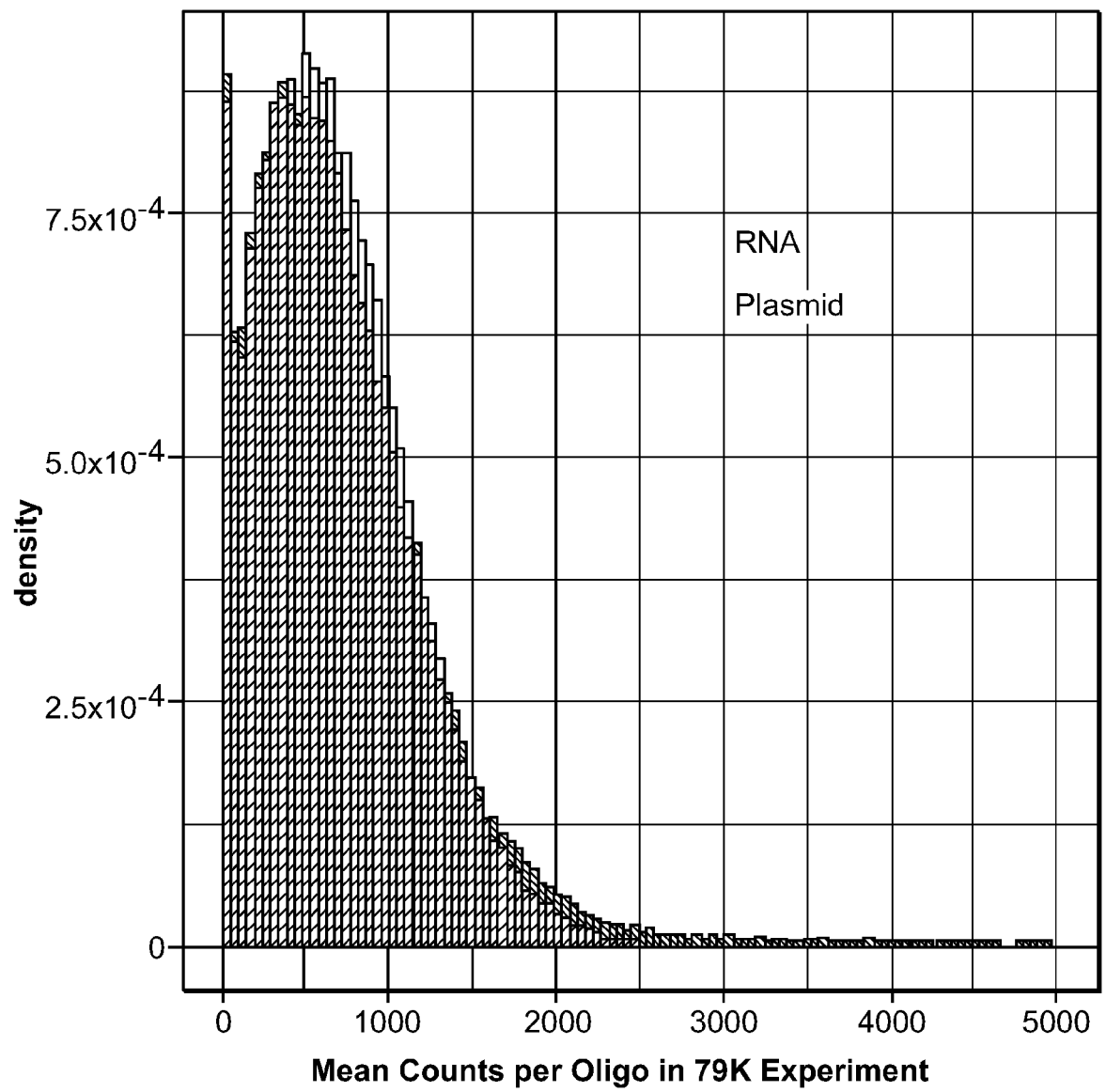
FIGS. 8A and 8B show read and tag count s per oligo.

Each oligo was captured by an average of 73 unique barcodes per replicate during sequencing (per sample range 34-117 barcodes) and a total read count of 1102 (FIG. 8A). A key feature of the approach is the use of additional barcodes to reduce variability between replicates; reducing this variability is key to achieving the sensitivity required to detect subtle difference between alleles, since detection requires distinguishing the distributions for the two alleles.

Figure 2D:
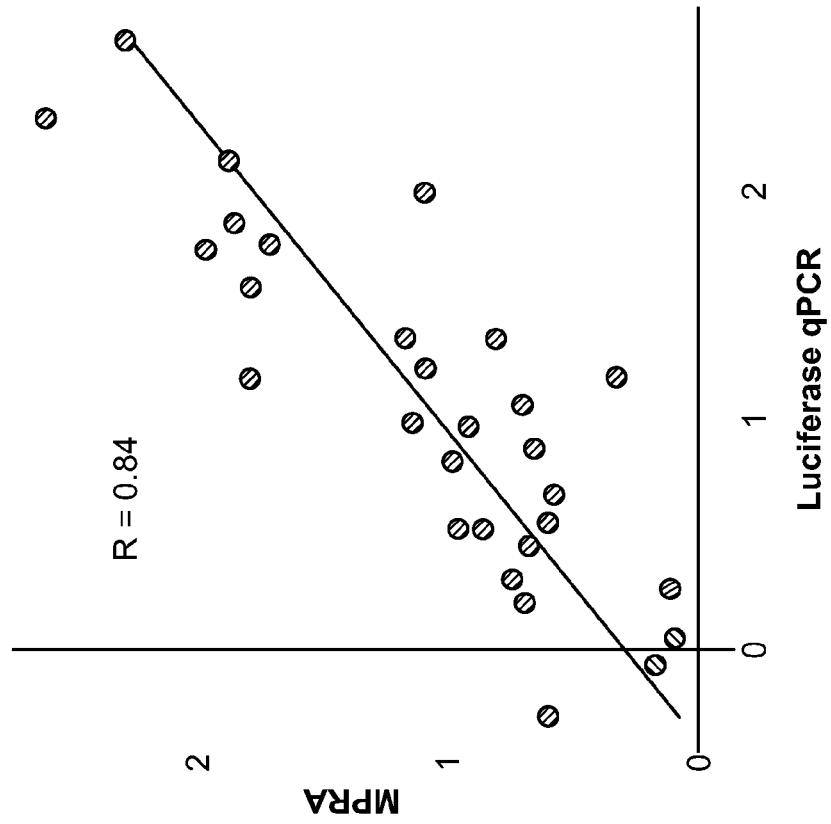
Figure 8B:
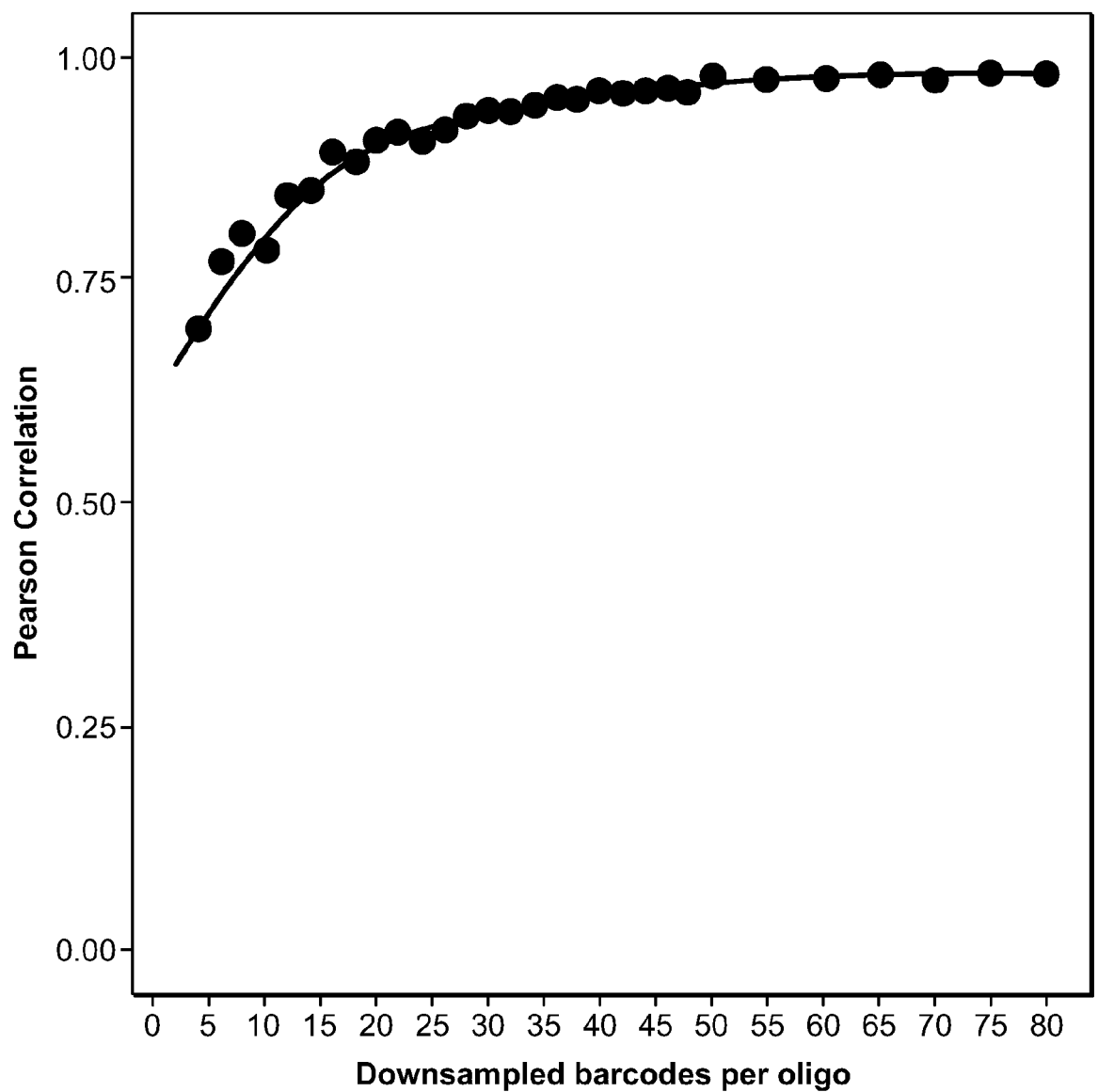

To evaluate how this variability depended on the number of barcodes, we downsampled barcodes for each oligo. Little fluctuation in the estimated mean oligo count was observed, as long as they were captured with greater than 20 barcodes (FIG. 8B). The variance between the individual replicates, on the other hand, continued to improve throughout the range from 20 to 50 barcodes, indicating that power to detect subtle differences between oligos is substantially impacted by barcode count (FIG. 2D).

This effect was highlighted in the second 7.5 k library: its smaller size allowed each oligo to be tagged with an average of 350 barcodes. This resulted in a greater sensitivity to detect weak expression changes, illustrating the impact of the number of barcodes tagging each variant, and also highlighting the requirement for normalization when comparing between libraries (FIG. 9A-D).

Example 3: Evaluating Regulatory Activity of the Oligos

Figure 9A:
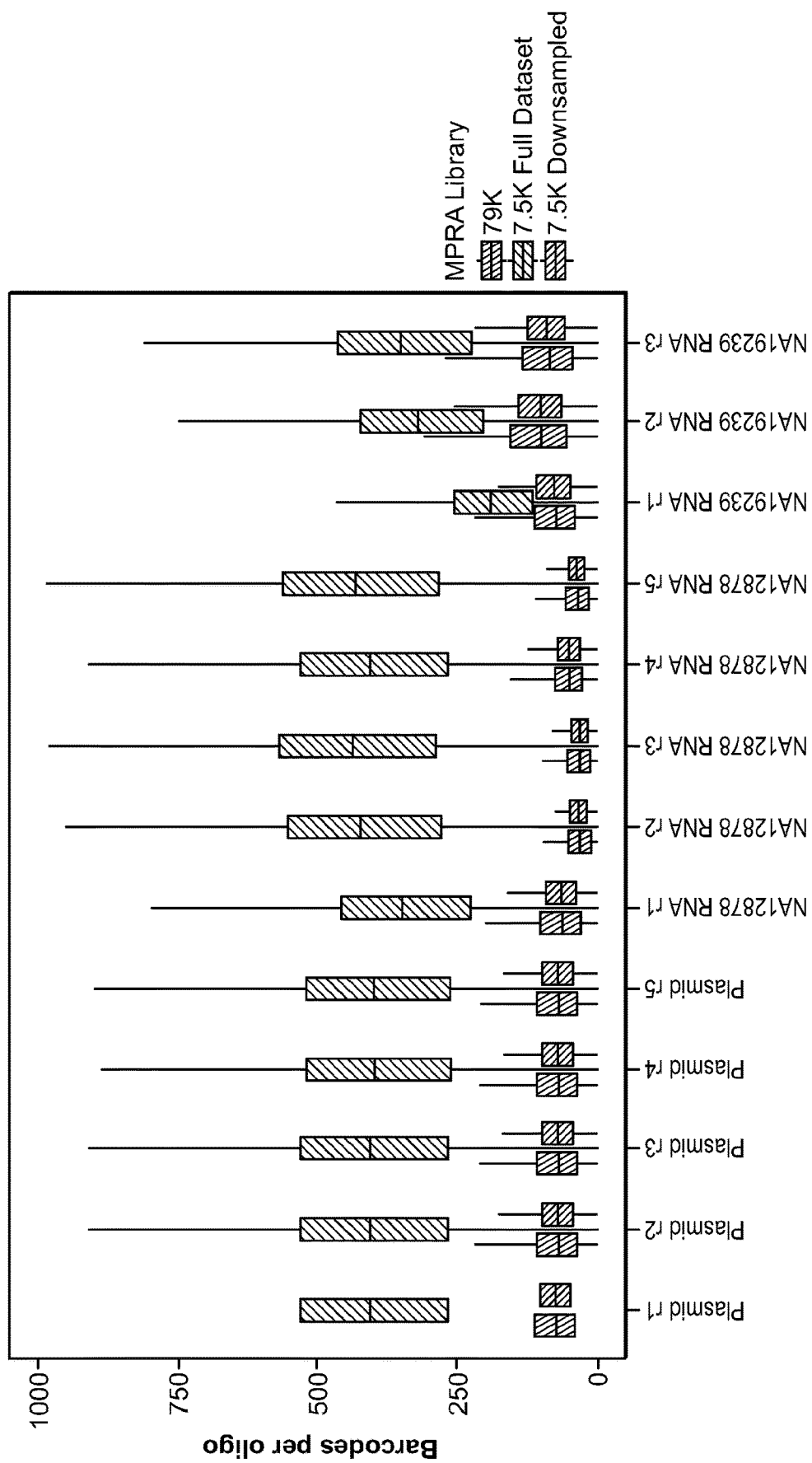
FIG. 9A-9E provides performance measures of the 7.5 k & 79 k MPRA experiment s.
Figure 9B:
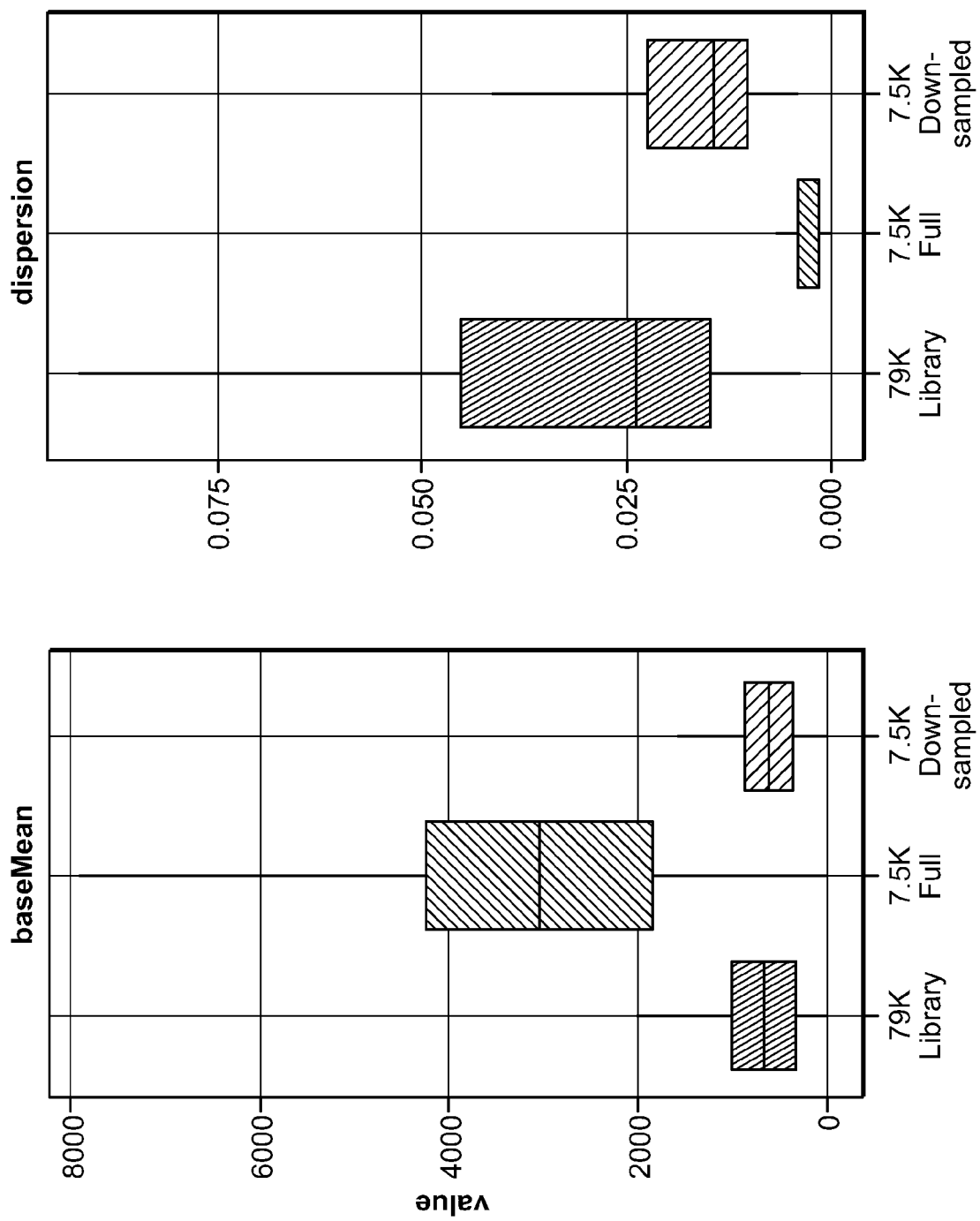
Figure 9C:
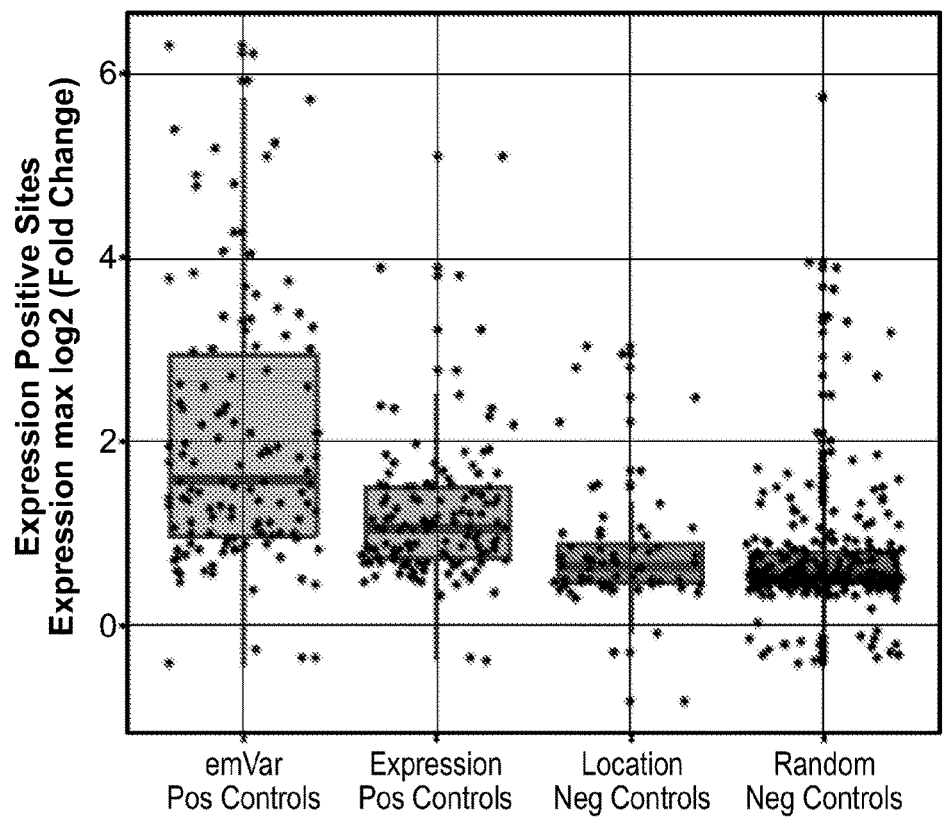
Figure 9D:
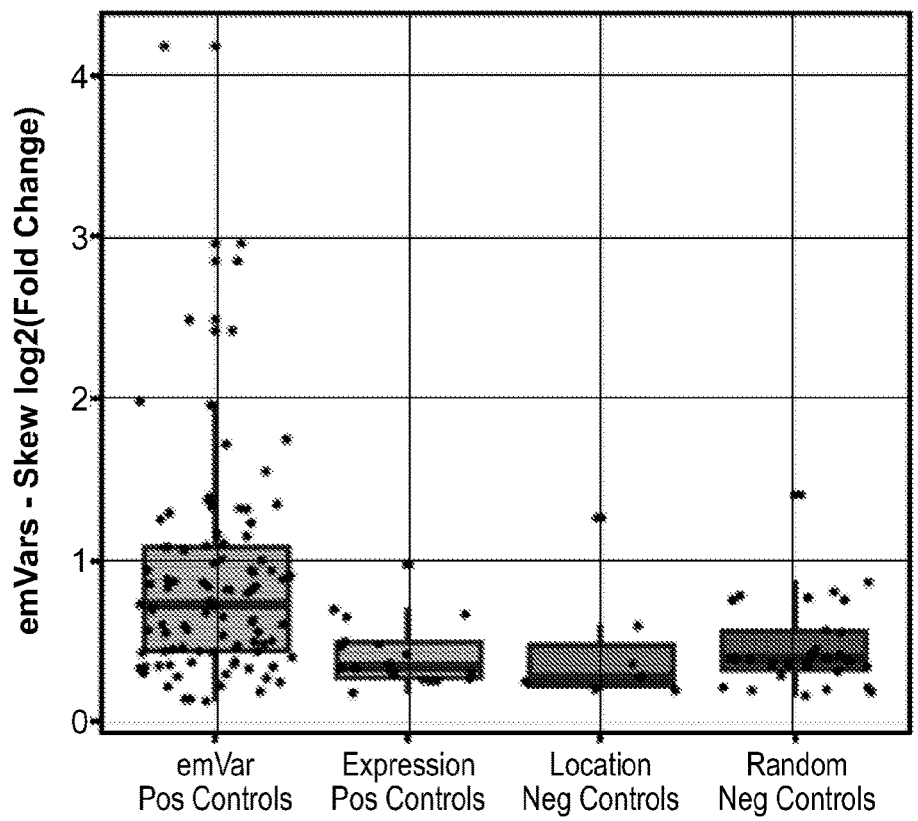
Figure 9E:
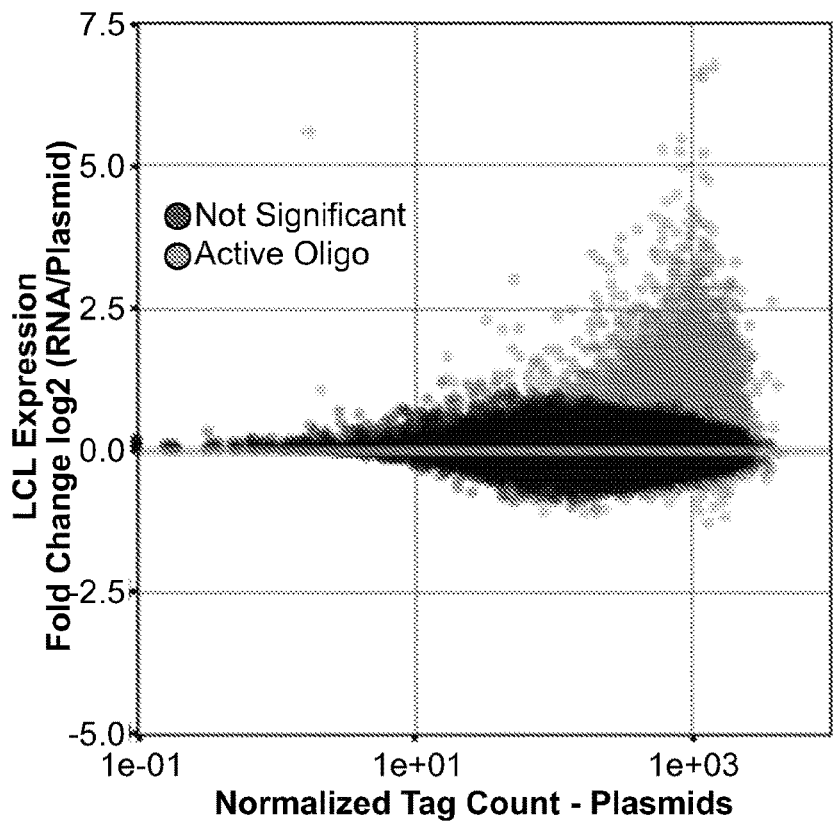
Figure 9F:
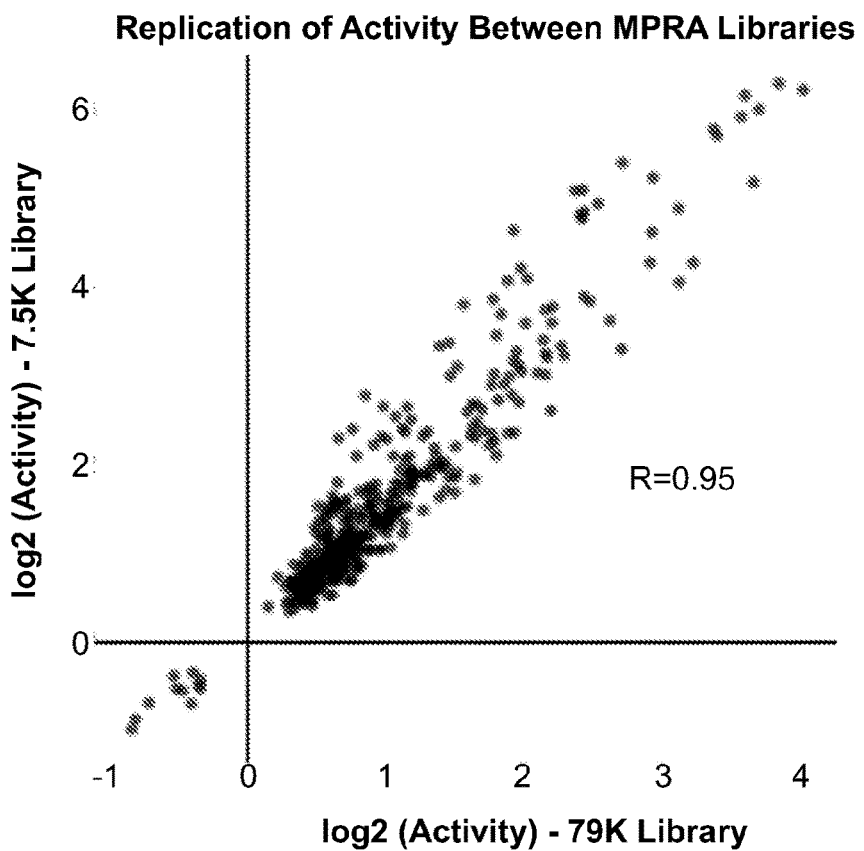
FIG. 9F is a scatter plot showing replication of MPRA active sequences for positive controls oligos discovered in the original 79 k 1 library (x-axis) and tested in the 7.5 k library (y-axis). Only sequences that past significance thresholds in the 79 k library are shown.

Before looking for allelic effects, we first identified the subset of sequences for which either or both variants altered the expression of the reporter. Of the 29 k variants evaluated in the assay, 3432 (12%) resided within a sequence context that showed over or under expression of the reporter for either the reference or alternate allele in LCLs (Table 1).

often than between different cell types (74% between NA12878 147 & NA19239 compared to 52% between NA12878 and HepG2). This difference in overlap is likely an underestimate, since only three replicates were performed in NA19239 compared to five in HepG2. The active sequences were reproducible, with the effect sizes being highly correlated when active variants were re-tested in the 7.5 k MPRA experiment (R=0.95) (FIG. 9F).

Figure 3C:
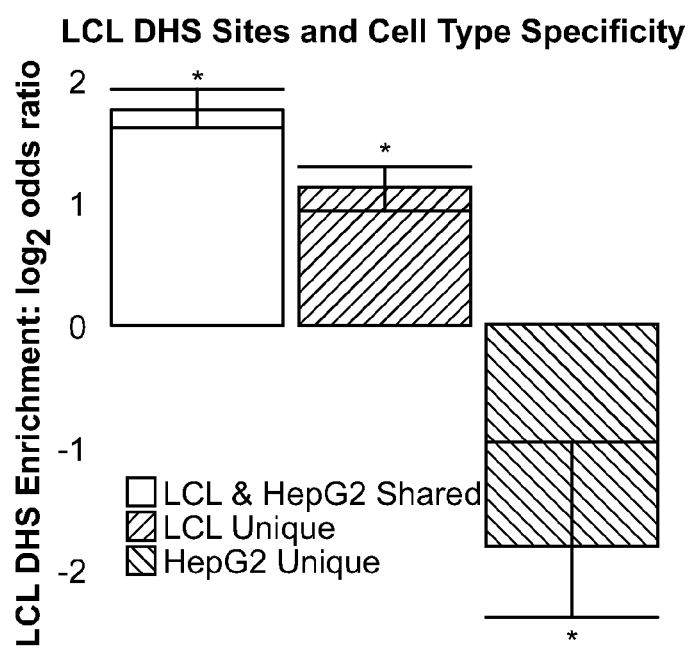

The sequences that scored as active in the assay are significantly enriched for markers associated with regulation in the genome, including open chromatin, biochemical marks denoting active promoters and enhancers, and individual transcription factors. We first evaluated overlap with open chromatin, as identified by DNase hypersensitivity sites (also termed DHS). We found 43.3% of the active sequences were marked as DNase hypersensitivity sites compared to only 19.4% for the non-active sequences, a 2.2 fold enrichment (OR=3.2, p=1.8×10-191, FIG. 3B). Histone marks associated with active promoters and enhancers (H3 k4me3, H2az, H327ac, CAGE) were both similarly enriched, while marks associated with heterochromatin and/or the blocking of transcription initiation (H3 k9me3 and H3 k36me3) were significantly depleted, as expected (FIG. 3B). The strongest enrichments were seen with individual transcription factor (TF) binding locations, with increases rang-

TABLE 1

High confidence emVars associated with known GWAS loci

| GWAS Trait | Gene(s) | Sites Tested by MPRA | | | Encode & | chr | Pos (hg19) | $r^2$ with lead GWAS SNP |
| --- | --- | --- | --- | --- | --- | --- | --- | --- |
| | | All[a] | Encode[b] | emVar | emVar[c] | | | |
| Mean platelet volume | KIF1B | 2[a] | 4 | 3 | rs4240912 | 1 | 10437778 | 0.92 |
| | | | | | rs5670157 | 1 | 10458439 | 0.92 |
| Wilms tumor | DDX1 | 70 | 3 | 1 | rs50016948 | 2 | 15728544 | 1 |
| Renal function-related traits | PAX8 | 18 | 5 | 1 | rs7578384 | 2 | 113903395 | 0.96 |
| Ankylosing spondylitis | PTGER4 | 5 | 4 | 1 | rs9282753 | 5 | 40490609 | 0.99 |
| Chrohn's disease | ERAP2 | 147 | 25 | 2 | rs1383974 | 5 | 96293810 | 0.91 |
| Nasopharyngeal carcinoma | IFITM4P, HLA-H, HCG4P5, HLA-L, HLA-G | 73 | 22 | 5 | rs116025518 | 8 | 29910189 | 0.98 |
| Beta-2 microglubulin plasma levels | HCG27, HLA-L | 41 | 39 | 1 | rs118587107 | 8 | 31239227 | 0.92 |
| Systemic lupus erythematosus | BLKFAM107A | 16 | 14 | 1 | chr8:11353110:D | 8 | 11353110 | 1 |
| Narcolepsy with cataplexy | UBXN2B | 12 | 3 | 1 | rs563161688 | 8 | 59323811 | 0.95 |
| IgG glycosylation | B4GALT1 | 12 | 8 | 1 | rs12342831 | 9 | 33124872 | 1 |
| Inflammatory bowel disease | MAP3K8 | 31 | 2 | 3 | rs306587 | 10 | 30722908 | 0.98 |
| Crohn's disease | CREM | 241 | 22 | 5 | rs16935880 | 10 | 35415468 | 0.99 |
| | | | | | rs4034730 | 10 | 35415558 | 0.99 |
| Body mass index | C1QTNF4 | 26 | 1 | 1 | rs35184771 | 11 | 47475489 | 0.97 |
| Atopic dermatitis | AP5B1, OVOL1 | 2 | 1 | 1 | rs10791824 | 11 | 65559268 | 0.91 |
| Mean corpuscular hemoglobin | PTPLAD1 | 60 | 7 | 1 | rs28640237 | 15 | 66070902 | 0.99 |
| Body mass index, Obesity, Weight | EIF3CL, EIF3C, SPN51, CDC37P1 | 137 | 33 | 4 | rs7198606 | 16 | 28875122 | 1 |
| Parkinson's disease | STX4 | 50 | 10 | 2 | rs58726213 | 16 | 31044653 | 0.95 |
| | | | | | rs11805038 | 18 | 31085171 | 1 |
| Bone mineral density | C17orf53 | 56 | 15 | 1 | rs227578 | 17 | 43210189 | 1 |
| Coronary heart disease | UBE2Z | 105 | 18 | 8 | rs4378858 | 17 | 46993370 | 0.99 |
| Liver enzyme levels (alkaline phosphatase) | GIN51, ABHD12 | 310 | 45 | 5 | rs2258769 | 20 | 25278650 | 0.99 |

[a]All variants tested in this study by MPRA with and r2 at 0.9 or greater to the lead eQTL variant.
[b]Variants within the tested subset classified as having strong encode support (Supplemental Experimental Procedures).
[c]emVars that were classified has having strong encode support.

Of these, 95% enhanced expression of the reporter (FIGS. 3A & 10A-10C). This bias towards higher expression could reflect the true proportion of activating to silencing elements in the genome. On the other hand, it likely also reflects a limited power to detect a signal reduction in this version of the assay, which includes only a minimal TATA box promoter between the oligo and GFP. Regulatory sequences were shared between LCLs from different individuals more ing from 3 to 39-fold for all TFs surveyed in LCLs by ENCODE, except for the repressor element Ezh2. Enrichment was cell type specific, again as expected, with sequences were active only in LCLs and not HepG2 cells being enriched for DNase hypersensitivity sites in LCLs only (OR=2.2, p=6.6×10-32). Similarly, sequences that were active only in HepG2 cells were depleted in LCL DNase hypersensitivity sites (OR=0.29, p=8.7×10-8) compared to all other sites tested (FIG. 3C).

Example 4: Identification of Alleles with Differential Activity

Focusing on those sequences for which at least one allele affected the expression of the reporter, those that showed differential expression between the reference and alternate allele ("allelic skew") were identified. Of the 3432 active sequences, 842 showed allelic skew, which are referred to herein as "expression-modulating variants" (emVars) (Table 1).

Figure 4B:
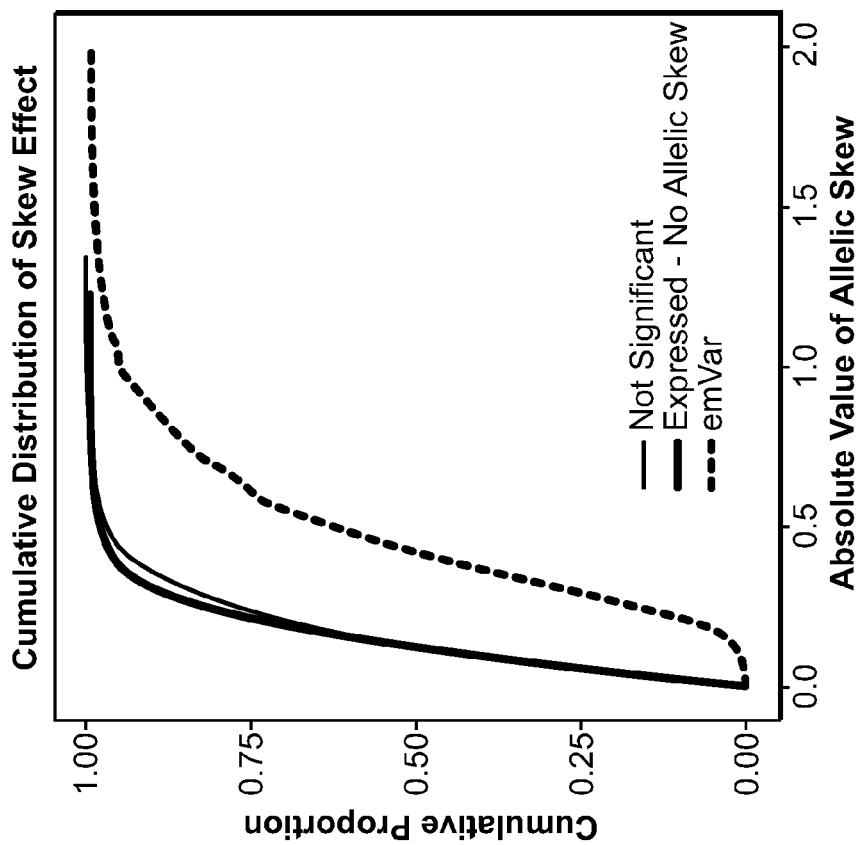
FIGS. 4A-4D show expression-modulating variant (em-Var) reproducibility and effect size distribution.
Figure 4A:
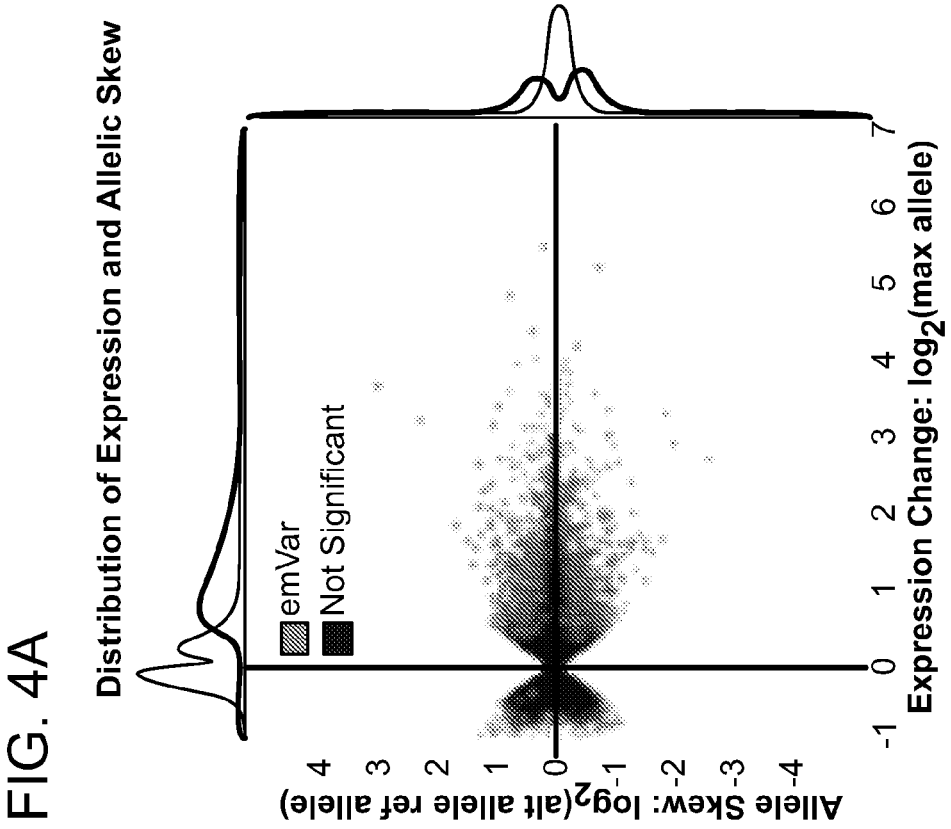
Figure 4C:
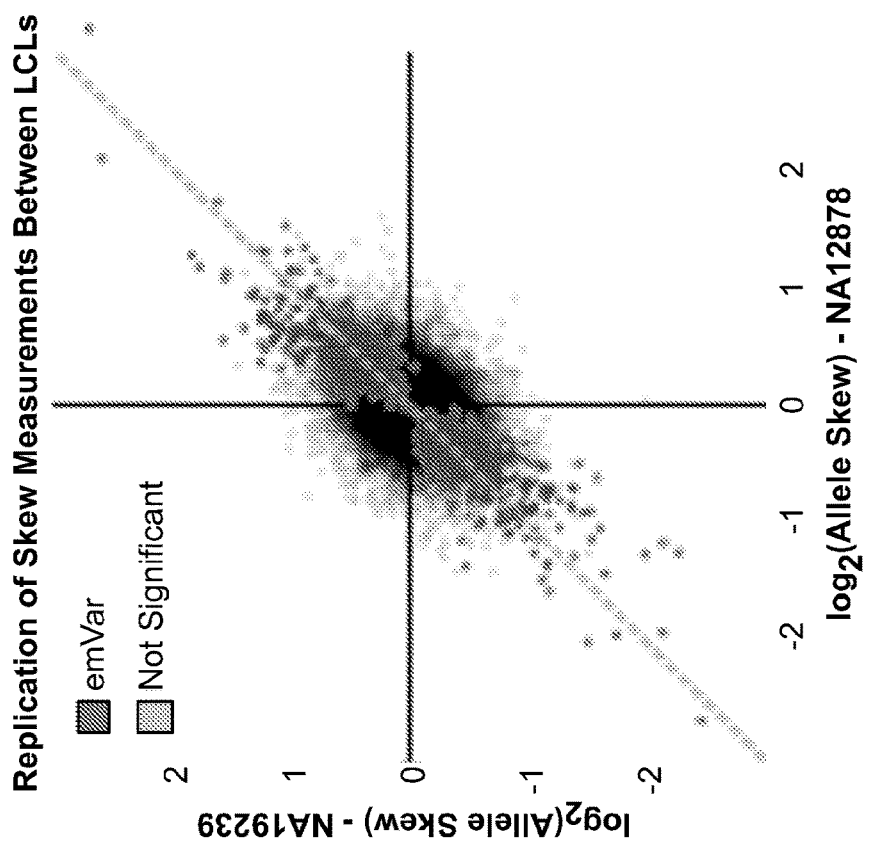
Figure 4D:
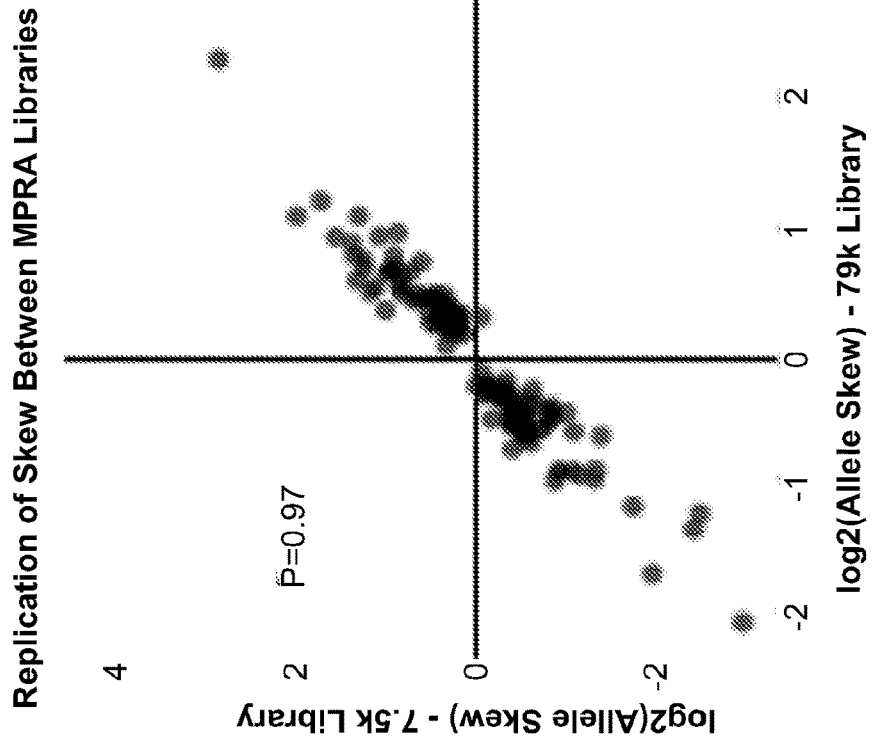
Figure 10A:
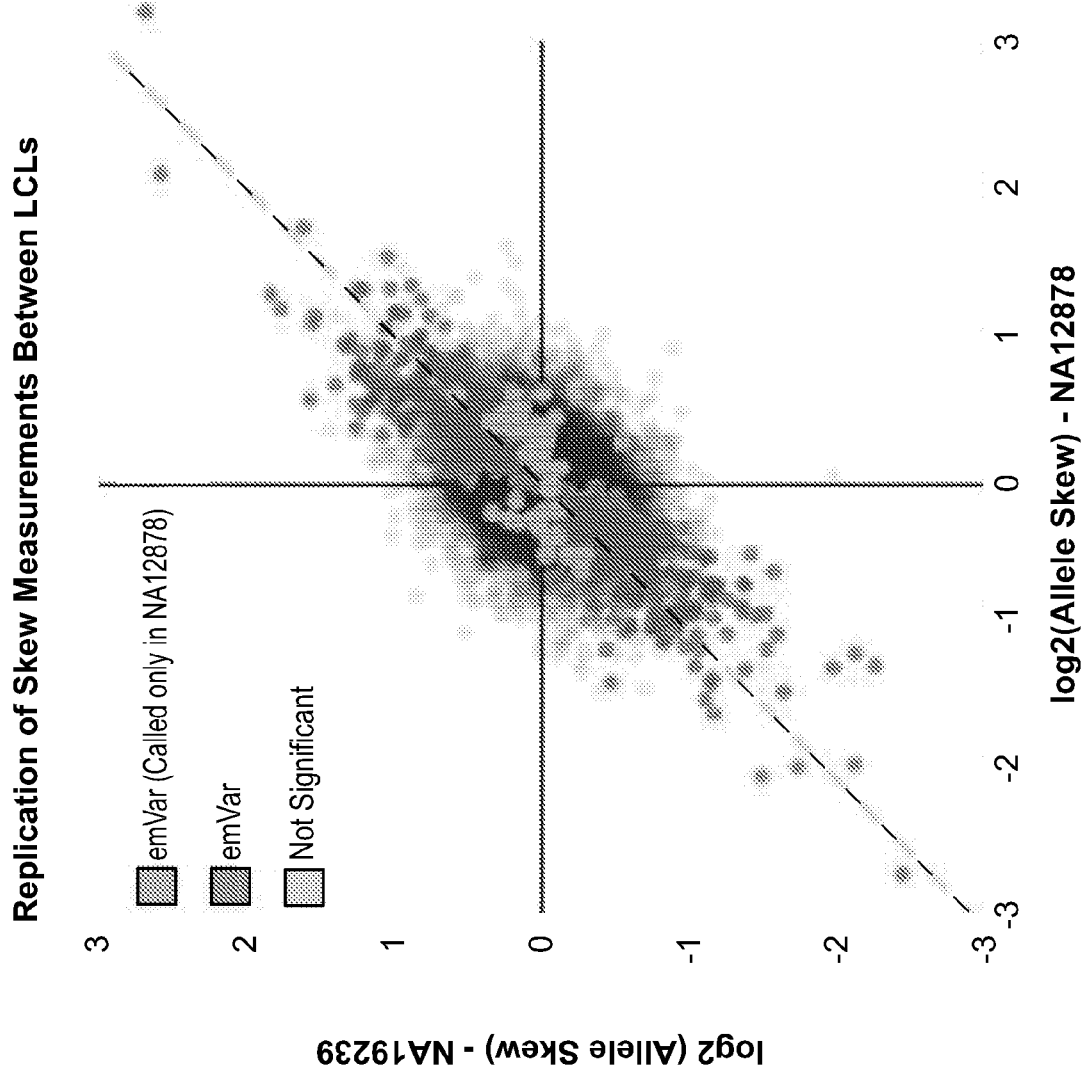
FIG. 10A-10E plots performance of the allelic skew measurements in the 79 k library.

Most of the emVars exhibited modest expression differences between alleles: only 46 had more than a 2-fold change (FIGS. 4A & 4B). The changes were, however, highly reproducible. 127 emVars were randomly selected for testing in the second, 7.5 k MPRA experiment and observed strong correlation for allelic skew to that of the 79 k experiment (R=0.97) (FIG. 4C). For all 842 emVars, the effect size was highly correlated between the two LCLs tested (r=0.92) and moderately correlated between LCLs and HepG2 cells (r=0.63) (FIGS. 4D & 10A). Concordant with observations that eQTLs are associated with promoter regions, we saw a 13.6-fold enrichment of emVars within core promoters (+100/−50 bp) relative to our test set of 29 k variants, and a 113.7-fold enrichment relative to all common variation (RR=14.8, p=2.7×10-52 & RR=113.7, p=1.2×10-121 respectively). Despite this enrichment, many emVars fell outside promoters, with 59% lying at a distance of 10 kb or more from the nearest transcription start site (TSS), suggesting a prominent role for distal regulatory elements.

Figure 5A:
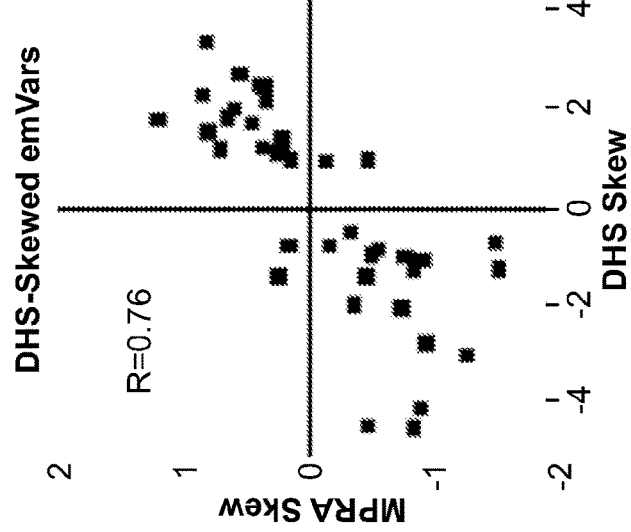
FIGS. 5A-5E shows emVar concordance with existing measures of allelic effect.
Figure 5B:
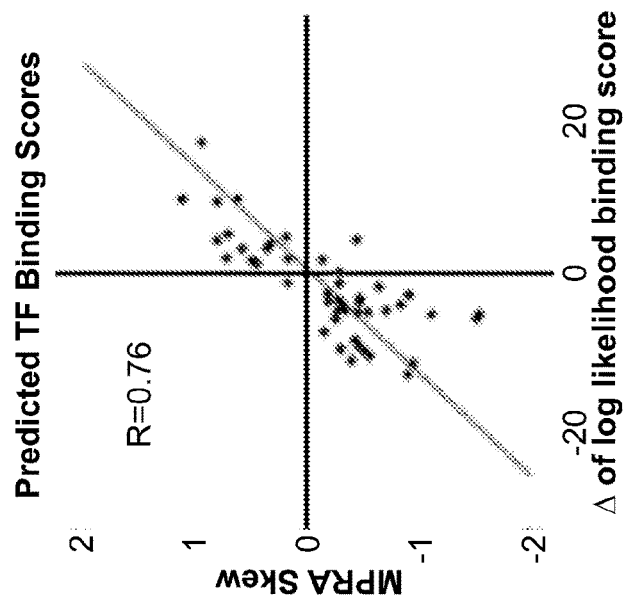

Like the overall set of active sequences, emVars were enriched for markers associated with regulation such as TF binding. It was next determined whether the presence of allelic skew correlated with predicted disruption of a TF motif. Of the emVars that overlapped a ChIP-seq peak for a given TF and that contained the corresponding TF motif, the predicted strength of TF binding (based on position weight matrices) differs significantly between alleles in 76% of cases (35 out of 46, had a difference of at least 3 in log-likelihood binding score based on the position weight matrices). This was 4-fold greater than the difference for active sequences that did not show allelic skew (OR=4.1, p=8.1×10-8) and 41-fold greater than for the non-active sequences (OR=42.7, p=1.9×10-36, FIG. 5A). The quantitative change in predicted binding also correlated with the magnitude of allelic skew observed by MPRA, supporting a direct relationship between predicted binding dynamics and regulatory 227 activity within MPRA (R=0.47, p=6.4×10-10, FIG. 5B).

Figure 5C:
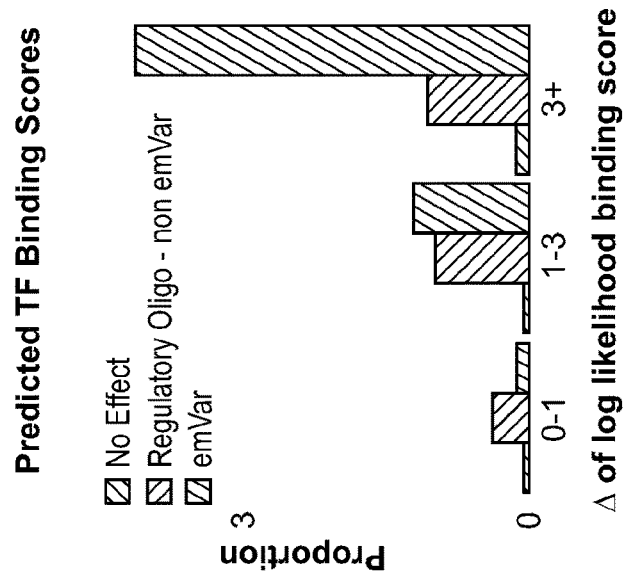

It was predicted that if emVars were true regulatory variants, then the allele associated with higher expression would also be associated with greater chromatin accessibility as measured by DNase hypersensitivity sites in their native context. emVars that were heterozygous at DNase hypersensitivity sites in LCLs were examined to see if there was an allelic skew in DNase hypersensitivity sites status by counting the number of DNase hypersensitivity sites reads attributed to each allele. emVars were significantly more likely to show DHS skew than active sequences that were not emVars (OR=2.5, p=0.003). Furthermore, 89% of variants shared the same direction of effect with a strong correlation in the magnitude of allelic skew in the activity of emVars and the number of reads at DHS sites (R=0.78, p=1.0×10-8, FIG. 5C). It was also predicted the same effect would be observed for TF-binding as measured by ChIP-seq. emVars were more likely to show allelic skew in the binding of at least one overlapping TF than active sequence that were not emVars (OR=1.9, p=0.03). For emVars that showed allelic skew in TF occupancy for at least one TF, there was a substantial concordance of direction and magnitude between the allelic skew in TF binding and the allelic skew in activity (77% agreement in directionality, R=0.60, p=2.1× 10-7, FIGS. 11A & B).

Example 5: Estimating Assay Reproducibility and False-Discovery Rate (FDR)

One goal was to estimate the specificity of the MPRA assay. Because many of the variants tested are not actually drivers of eQTLs, a set that is likely to be enriched was a focus: the top associated variant for each eQTL and all variants in perfect LD. An analysis was carried out on these 11,213 variants from 3,642 eQTLs taking into consideration that only one, if any, of the variants in each region may be a true regulatory variant and only a fraction of these may drive transcriptional regulation discoverable by MPRA.

Allelic skew in activity was observed for 27% of the active sequences associated with an EUR eQTL, and 26% of the YRI variants. In contrast, only 9% of the active sequences for the location-matched controls exhibited allelic skew, suggesting that two-thirds of the emVars associated with an eQTL peak are true causal variants for that peak. Randomly selected controls gave a similar result: 11% of active sequences contained emVars. Based on these results, the positive predictive value (PPV) was estimated to be 58-68%. Because the controls were tested independently in a second library, it was important to normalize the tag-counts to match those of the first experiment. To validate this normalization, the proportion of active sequences in the two libraries was compared. In the second, 7.5 k library, 13.4% of the 500 location-matched and 9.7% of the 2700 randomly selected controls scored as active sequences, compared to 12% for the 79 k library (Supplemental Experimental Procedure).

As an alternative approach to explore the false discovery rate, how often the direction of effect agrees between MPRA and the eQTL analysis was compared. A first focus was on those emVars that reside in regions biologically annotated as likely to be related to enhancer function (by virtue of being marked by at least two of the following; DHS, CAGE, histone ChIP or TF-ChIP). 80% agreement in directionality was observed, corresponding to a PPV of 59% (R=0.61, p=7.5×10-15, FIGS. 5D & 11C). Notably, when sites not supported by annotation were examined, a level of agreement consistent with random chance (48%, R=0.06, p=0.61) was observed. When all emVars were considered together (regardless of whether they are annotated as related to enhancer function), the concordance was 67% (PPV of 34% (R=0.33, p=4.8×10-7). (It should be noted that MPRA may not always correctly model the direction or magnitude of a variant's effect because the assay isolates a sequence from potential cofactors that may modify the effect; this has been observed for the genes yy1 and dorsal.) Finally, it was explored whether some of the discordant emVars might represent false eQTL discoveries by removing 277 the weakest one-third of eQTL associations; a further increase in agreement for annotation-supported emVars of 84% was observed, suggesting that false positive eQTLs indeed contribute to the discordance.

Example 6: Estimating Sensitivity of the MPRA Assay

The sensitivity of MPRA to identify a causal eQTL variant was estimated. Based on previous estimates, the causal allele was expected to be in our enriched set (top eQTL variant and all variants in perfect LD) 34% of the time in the EUR population. Given the assay identified emVars in 8.6% (273/3171) of eQTL peaks, and 3-6% after accounting for false positives, a sensitivity of 9-18% in the EUR population was estimated. In the YRI population, lower LD makes it more likely that a top-scoring eQTL variant will be the causal allele, an estimated 41%. As expected a larger fraction was observed for YRI eQTLs with 13.8% ($^{65}/_{471}$) containing an emVar, 5-10% after accounting for false positives, giving an estimated sensitivity of 12-24%. When only taking into account variants supported by functional annotation, the estimated sensitivity was nearly equal by virtue of an increased PPV, emphasizing the value of filtering MPRA emVars with existing annotations. These estimates that MPRA can identify the causal allele for an eQTL for 9-24% of peaks when tested is in line with the previous observations that 23%-64% of eQTLs are driven by promoter or enhancer modifications, the processes that MPRA was expected to capture.

Figure 5E:
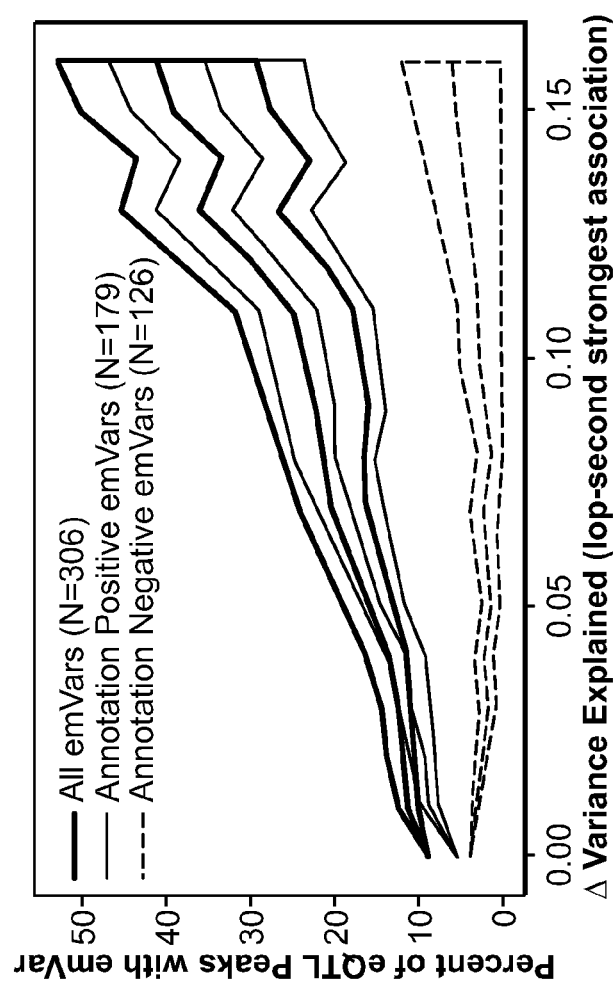
Figure 5D:
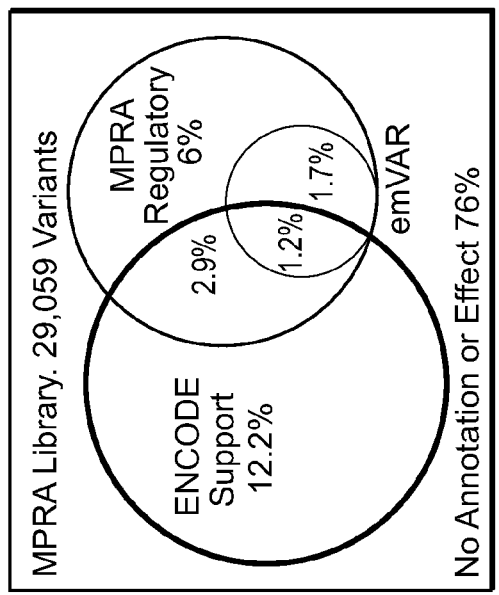

Two alternate estimates for sensitivity focusing on regions where the causal allele is likely to be in our data set were performed. Peaks were first partitioned based on the difference in correlation ($\Delta r2$) between the lead variant (the variant tested by MPRA) and the second strongest association. The top eQTL variant is most likely to be causal when the $\Delta r2$ is large; accordingly an increase of emVars in these regions was observed (FIG. 5E). Modeling this relationship using a logistic regression that also controlled for the effect size of the eQTL a sensitivity of 16-21%, was derived. Second, eQTL peaks were identified where the same top associated variant occurred in both EUR and YRI. Differing LD structure between the two populations decreased the number of linked variants and increased the confidence that the top variant is causal. Of the 34 shared variants, 8 were identified as emVars, suggesting a 24% sensitivity of MPRA to correctly identify the causal allele when it is tested. Both orthogonal approaches are consistent with the initial estimate of 9-24%.

Example 7: GWAS Associated Regions

Regions previously associated with a trait or disease in human studies were investigated in greater depth. For 209 eQTLs overlapping 163 GWAS loci, all alleles in strong LD ($r2>0.9$) of the lead eQTL variant were tested, a total of 9664 variants. 248 emVars in 99 eQTLs were identified. The emVars that also carry annotations associated with an enhancer or promoter were prioritized; 53 emVars in 56 eQTLs (a subset of these, further restricted by LD, is shown in Table 1). This represents a highly promising set of candidates and greatly reduced testing burden compared to current approaches. For example, applying only our ENCODE annotation criteria identifies 1302 variants across 171 of the 209 eQTL peaks.

Figure 6A:
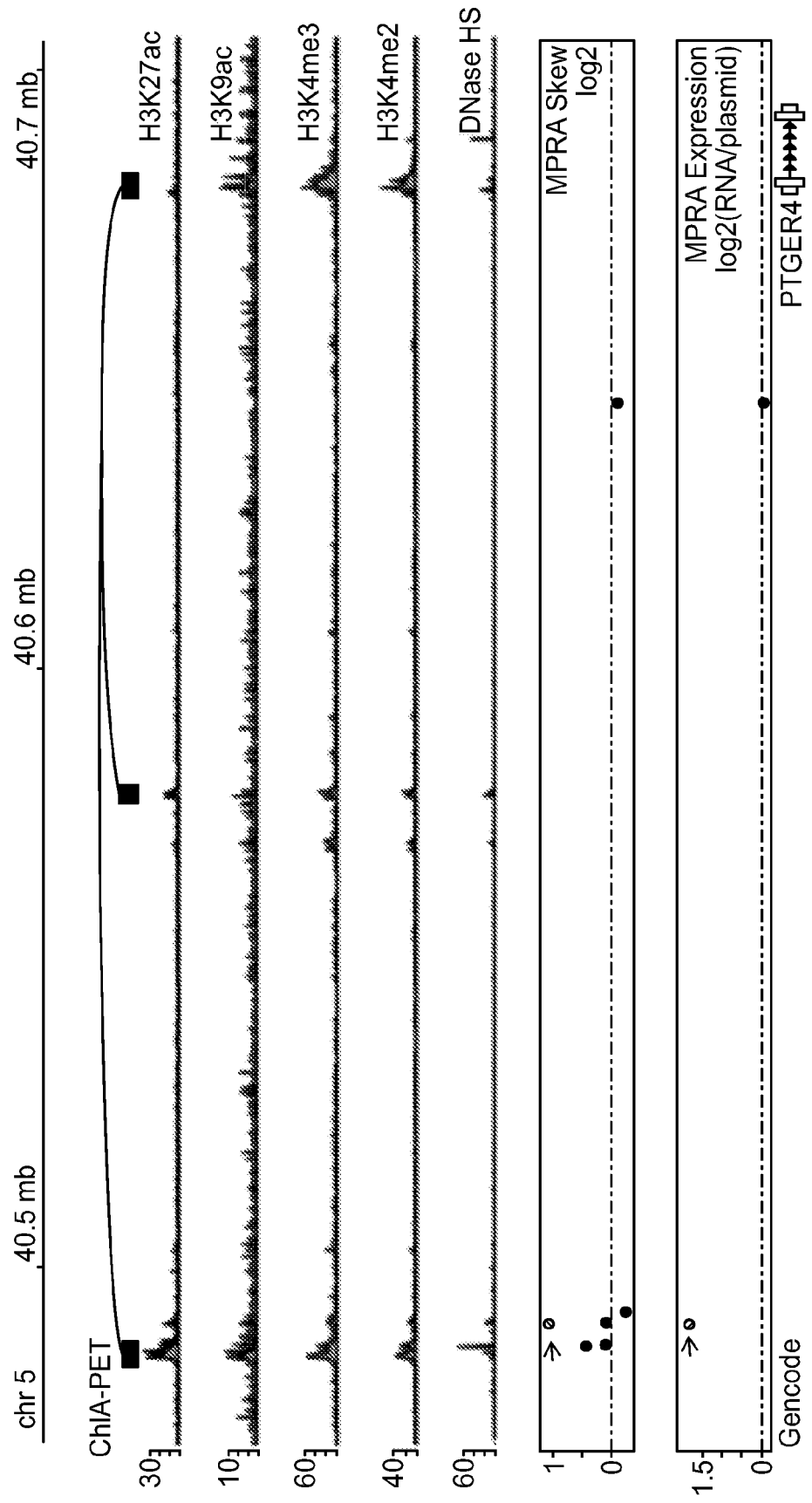
Figure 6B:
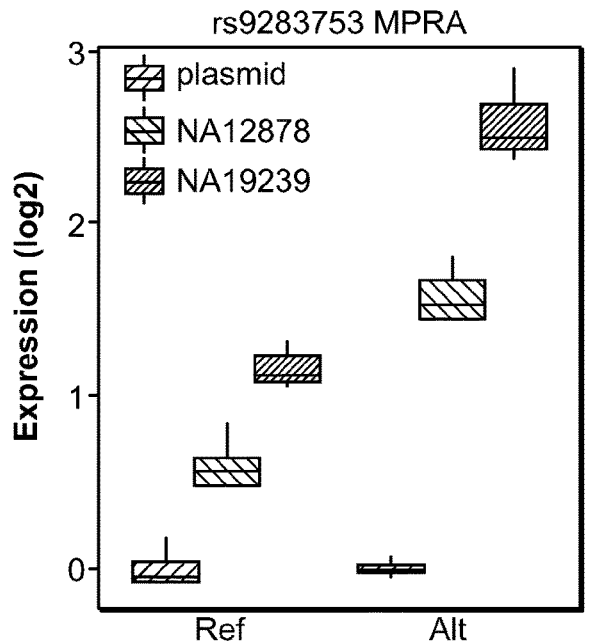
Figure 6C:
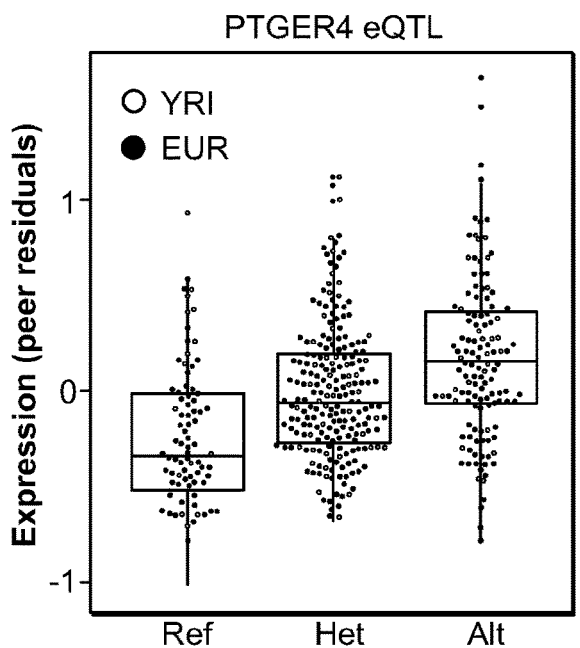
Figure 6D:
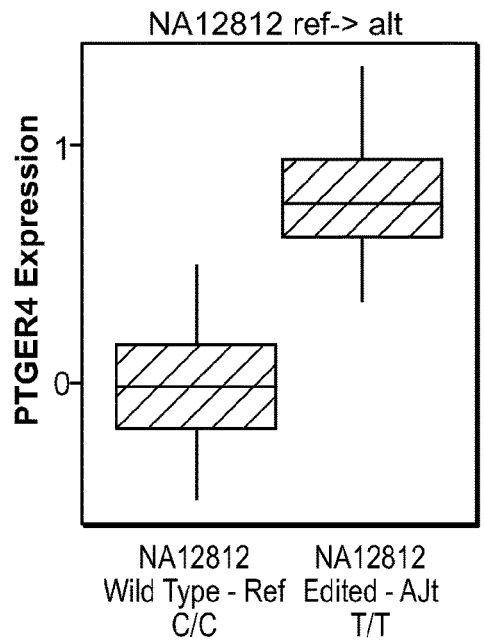
Figure 6E:
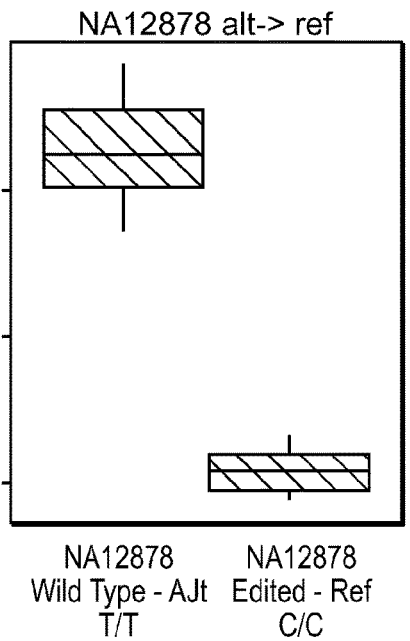
Figure 6G:
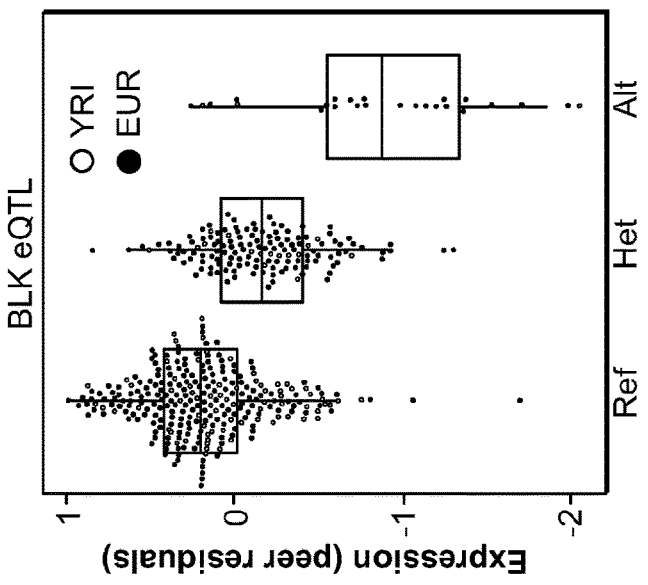
Figure 6H:
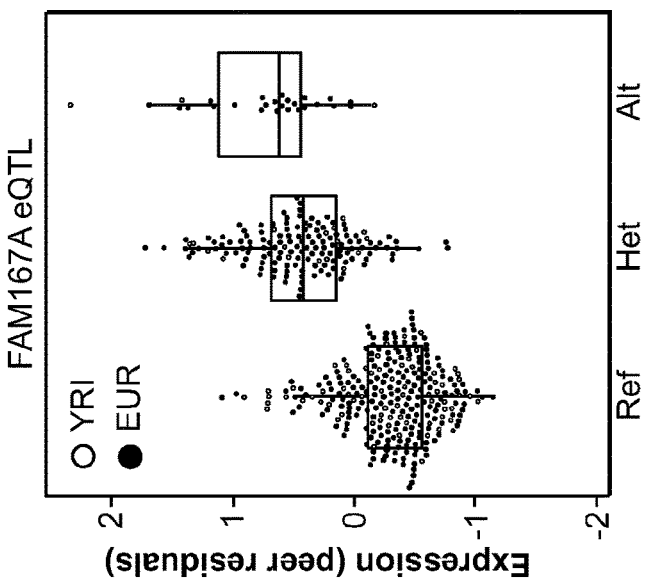
Figure 6I:
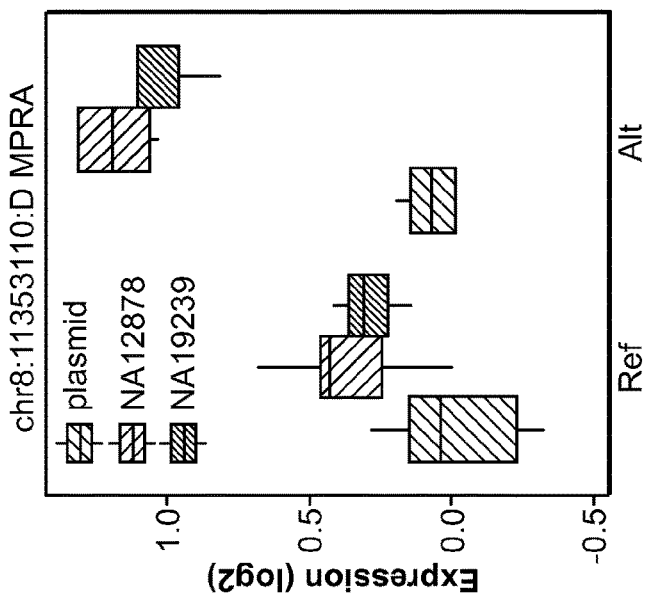

Candidates identified through MPRA still require experimental validation. A striking example was pursued in a distal enhancer for prostaglandin E receptor 4 (PTGER4). The emVar rs9283753 sits 150 kb away from the gene and is in strong LD with the top associated risk allele for ankylosing spondylitis (with moderate LD to risk alleles for Crohn's disease and multiple sclerosis) (FIG. 6A-C). The variant resides in a distal enhancer clearly defined by strong DHS and H3K27ac marks, with a C/EBP motif residing over rs9283753. The allele change is not predicted to alter binding of C/EBP, however, and further work will be needed to elucidate the mechanism of regulation. The PTGER4 emVar was validated by performing allelic replacement using homology directed repair with CRISPR/Cas9. Two cell lines, a homozygous ancestral (NA12878) and a homozygous derived (NA12812) individual were edited for the variant to test the effect of the allele in a controlled isogenic background. As expected from the MPRA and eQTL data, switching NA12878 to be homozygous for the derived allele caused a decrease in expression for PTGER4, while the replacement with the ancestral allele increased expression of NA12812 (FIGS. 6D-E). The concordant MPRA, eQTL and CRISPR data supported the hypothesis that the risk allele is associated with increased expression of PTGER4.

The finding of a regulatory variant in the distal enhancer in PTGER4 is consistent with prior observations that identify elements outside core promoters as a significant contributor to the heritable component of complex diseases. Looking more broadly, the 188 emVars in strong LD ($r2>=0.9$) with GWAS variants tend to lie further from promoters than randomly chosen eQTL variants: 78% (147) reside greater than 10 kb from an active TSS, compared to 53% for all other emVars. We observed a corresponding depletion in strongly linked GWAS emVars within core promoters compared to all non-GWAS emVars (RR=5.3, p=0.0015). There are many other promising candidates to pursue, including both a core promoter and intronic emVar in the BLK locus associated with systemic lupus erythematosus (SLE). The locus has previously been characterized by Guthridge and colleagues, who reported the promoter variant rs922483. We replicated this finding via MPRA while also observing a second emVar within the first intron of the gene. This is a one base deletion at chr8:11353110 that introduces a novel NF-kB binding site. Notably, we found this emVAR decreased expression of BLK while increasing expression of the nearby gene FAM167A, and was validated with the traditional luciferase assay (FIG. 6F-I). Moreover, this emVAR is in perfect LD with the top associated 352 SLE risk variant among Europeans, rs2618476.

The findings reported herein demonstrate that MPRA can be an invaluable tool for localizing individual causal variants influencing phenotypic traits. Hundreds of variants as putative causal alleles for gene expression were discovered, many of which are linked to known disease-causing loci. Furthermore causality was demonstrated by allelic replacement of an ankylosing spondylitis risk allele, rs9283753, which modulates expression of PTGER4 from a distal enhancer.

Figure 8C:
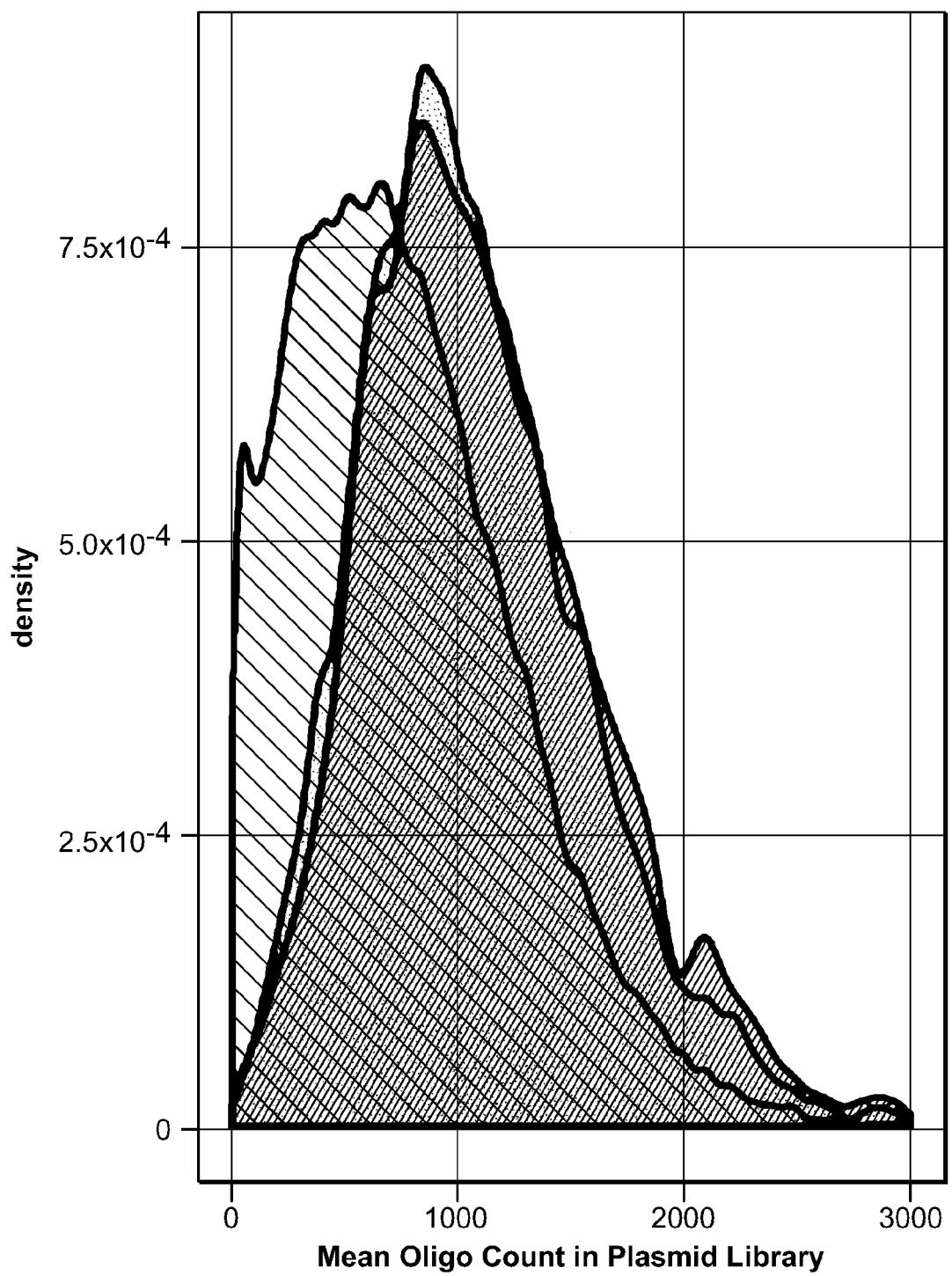
FIG. 8C is a density plot of unnormalized plasmid counts for all variants, expression—positive skew—negative, and skew positive variants tested in the 79 k assay.

Analysis of the proportion of expression variants suggests that for one third of the 79 k library, the analysis was underpowered due to a low abundance of the plasmid pool, something that could be overcome by increased sequencing and library uniformity (FIG. 8C). In addition, further improvements, such as longer oligo sequences to capture greater contextual information and the use of a stronger constitutive promoter to detect repressive elements, may provide substantial gains in sensitivity. Nevertheless, there is undoubtedly contextual information, such as long distance interactions, that will never be captured by an episomal assay.

One of the largest influences to the current sensitivity is the substantial role of post-transcriptional effects driving eQTLs; these are not targeted by our assay. For example, a recent analysis of eQTL causal variants estimated that 36% of sites fall within transcripts themselves and only 23% are attributed to known promoter/enhancer elements, suggesting a substantial role for post transcriptional activities. This implies that, at best, MPRA would have a maximum sensitivity of 23-64% for detecting an eQTL causal allele, since it is not designed to detect variants acting post-transcriptionally. In contrast, the same study reported a very different picture for autoimmunity GWAS hits: only 19% of causal alleles fell in transcripts and 67% resided in known promoter/enhancers, with the remainder associated with unannotated non-coding sequence. The discrepancy in the predicted mechanisms of eQTL and GWAS causal sites suggests that the sensitivity of MPRA may well be higher for disease-associated variants than reported here.

While the sensitivity may be increased through further technical development, the positive predictive value of 34-68% is likely an inherent property of the assay. This suggests that a substantial segment of the genome has the potential to change gene expression but is repressed from doing so, at least in immortalized lymphoblastoid cells, through modulating interactions or heterochromatin silencing. Endogenously silenced sequences likely also explain a proportion of the active sequences observed by MPRA, which was unexpectedly high. As a result some variants discovered by MPRA will be of little biological value. However, the assay still identifies 1-2 true causal allele for every 3 variants that score, which provides an enrichment and throughput unparalleled by alternative approaches. While MPRA does not prove causality it does substantially reduce the test space of alleles linked to a trait locus and provides a concise list of high priority targets for follow-up. Furthermore, the improved agreement with eQTL directionality when subsetting those emVars with supporting biological annotation demonstrates the strength of a combined approach when searching for non-coding causal alleles.

Regardless of the high-throughput approach taken to identify variants influencing gene regulation, whether it is computational or experimental, it is critical the results are interpreted as the product of a discovery tool and not a test for causality; a first step in the difficult task of linking a genetic loci to a physiological phenotype. By example, it was demonstrate for PTGER4 how the analysis can readily identify and validate an allele that influences gene expression and extending this observation further to a disease causation will require further work. Being able to identify and validate expression modulating variants from tens of thousands of sites will ultimately greatly aid in our ability to translate non-coding regulatory code and will bring us a step closer to the difficult task of linking human genetic variation to specific phenotypic traits.

Example 8: Additional Refinements

Figure 12:
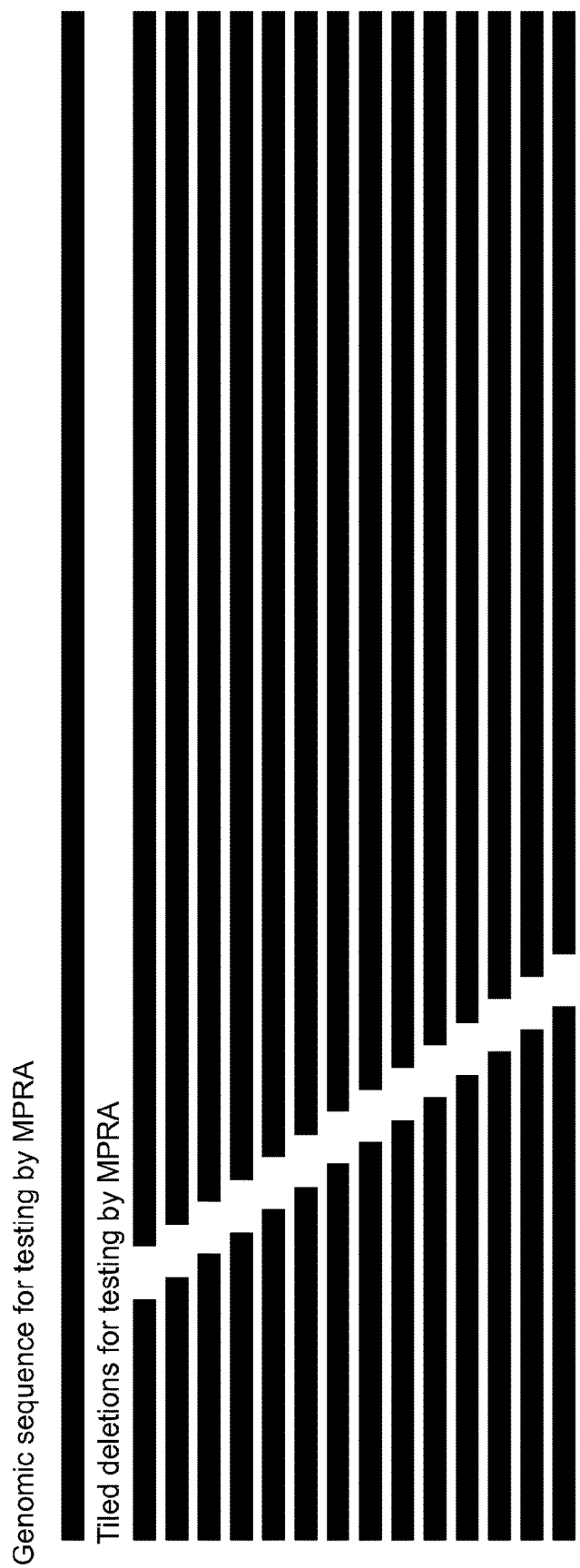
FIG. 12 is a schematic showing deletion mutagenesis using MPRA. For sequences identified by MPRA or by alternative characterization assays that are active but have cryptic/unknown mechanisms driving the activity, tiling deletions across the sequence can be performed to identify specific regions responsible for expression activity.
Figure 12:
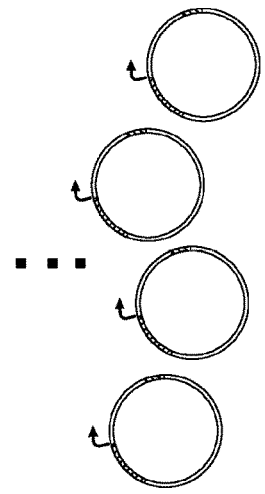
Figure 13:
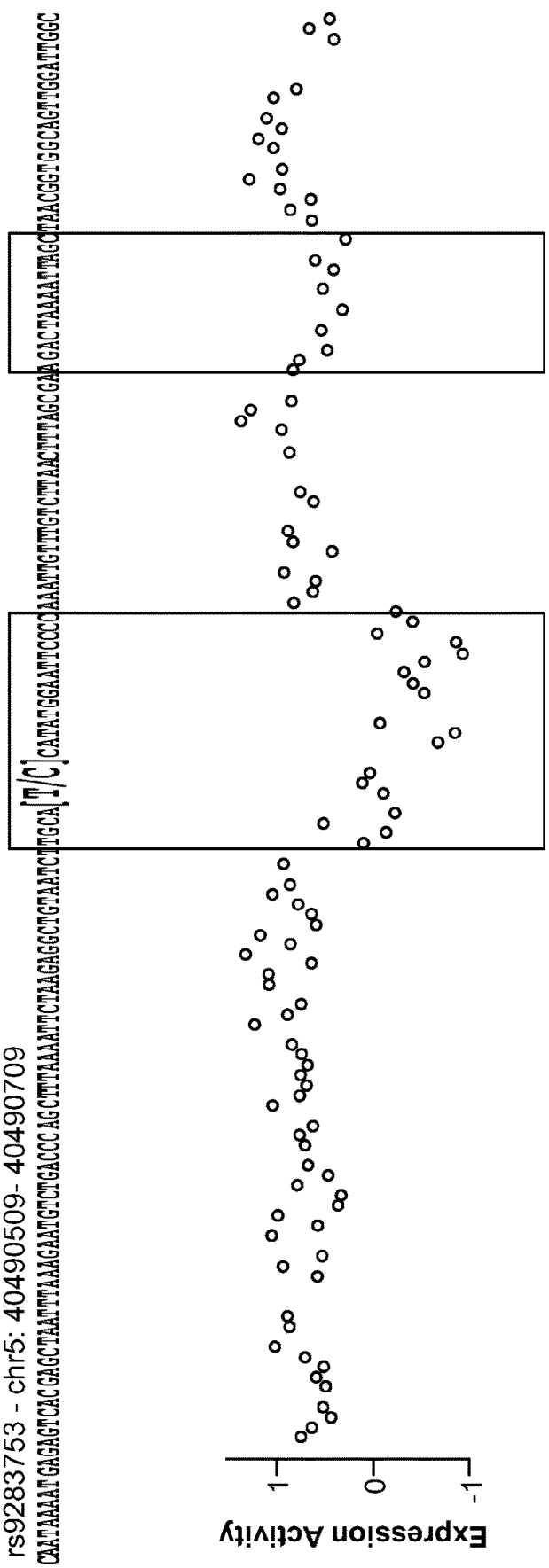
FIG. 13 is a schematic showing how activity measurements from tiled deletions identifies regions responsible for gene expression activity.
Figure 14:
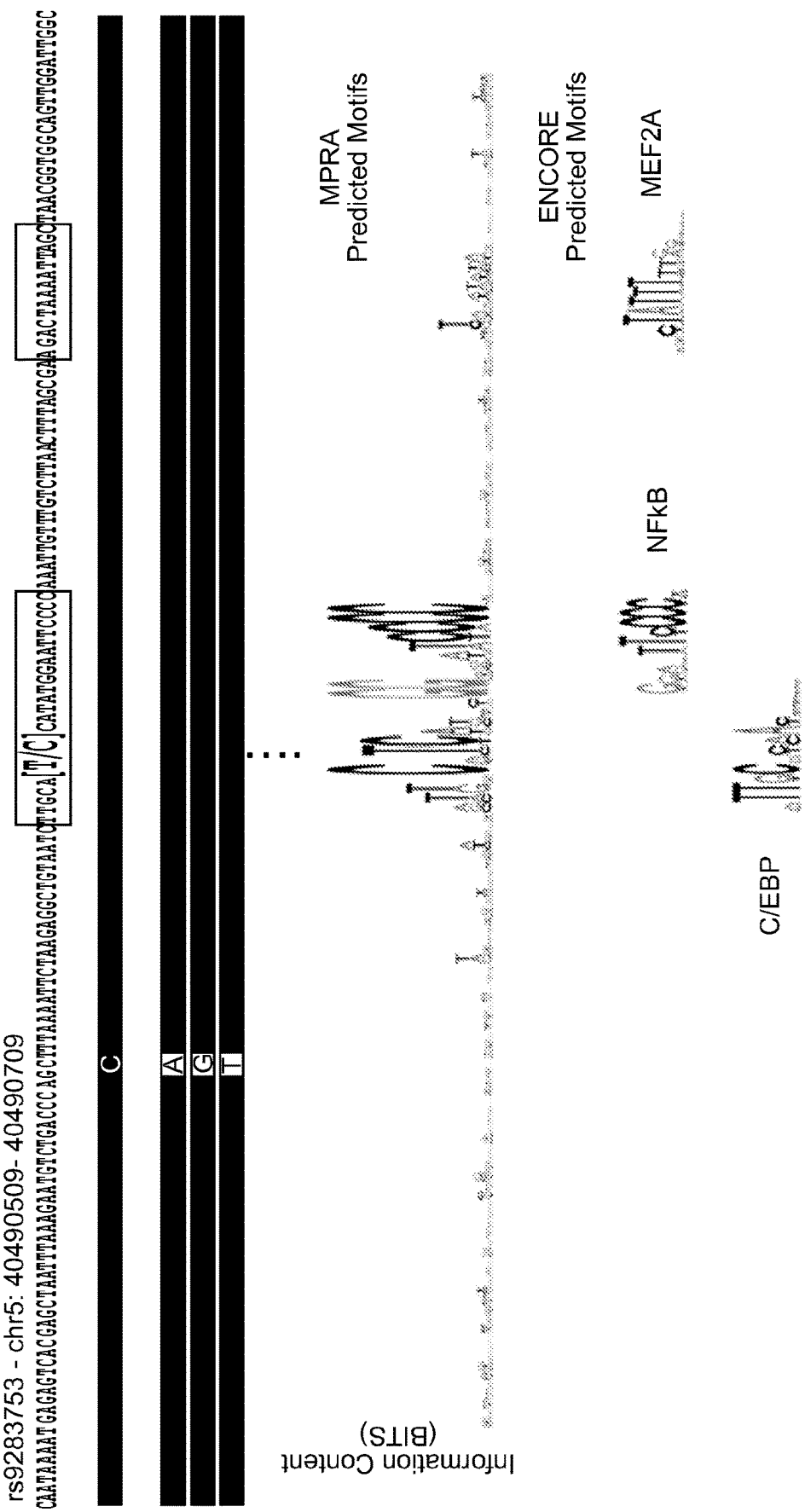
FIG. 14 is a schematic showing how saturation mutagenesis is used to identify precise binding partners and binding motifs. Saturation mutagenesis can be performed by mutating each base independently to the other four states (A/C/G/T/−). MPRA activity measurements from each position can be used to construct binding motifs for each position allowing the identity of the transcription factor to be determined.
Figure 15:
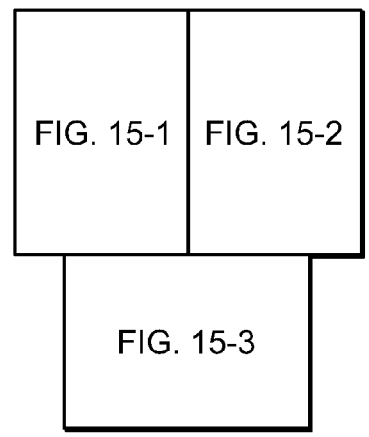
FIG. 15 is a schematic illustrating how MPRA can be used to measure activity in single cells. By increasing the numbers of barcodes, MPRA can be used to measure activity within individual cells allowing cell-to-cell variance of a regulatory element to be directly measured.
Figures 1, 15:
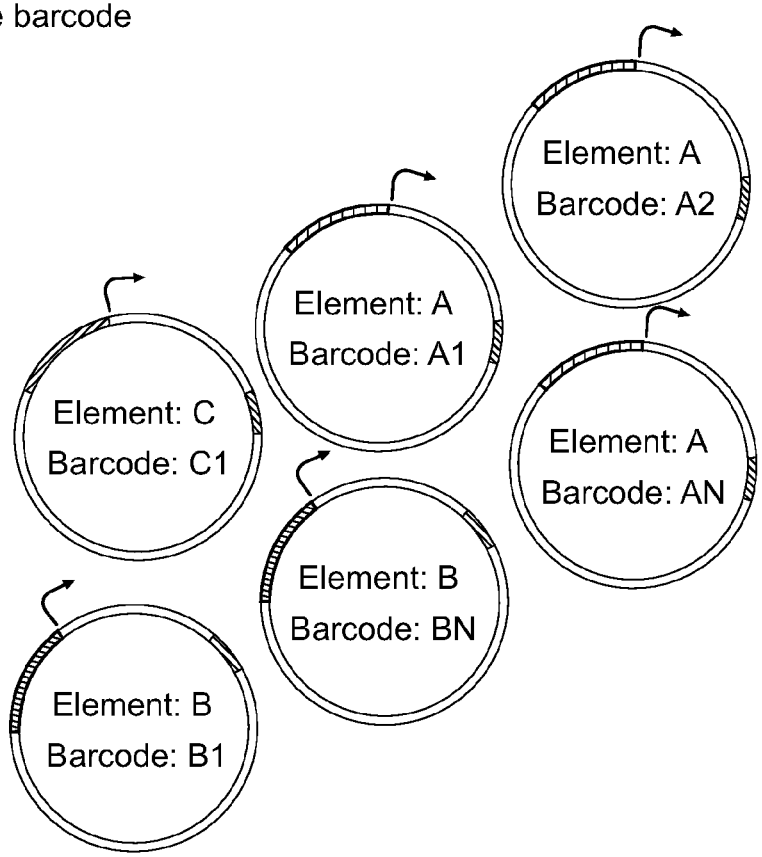
FIG. 1 is a schematic diagram showing an overview of the MPRA workflow. (A) Oligos are synthesized as 180 mers followed by cleavage off of the array. (B) The ssDNA is amplified, barcoded and converted to dsDNA by emulsion PCR which is then cloned into a reporter vector which has had the reporter gene removed to create the mpra:Δorf library (C). The plasmid library is linearized between the barcode and oligo sequence by restriction digest and a minimal promoter and GFP open reading frame is inserted by gibson assembly to create the final mpra:gfp library (D) which is used for transfection into the desired cell type (E). RNA is harvested from the transfected cells, mRNA is captured, sequenced (F) and barcode counts are compared to the count estimates from the sequencing of the mpra:orf library (D).
Figures 2, 15:
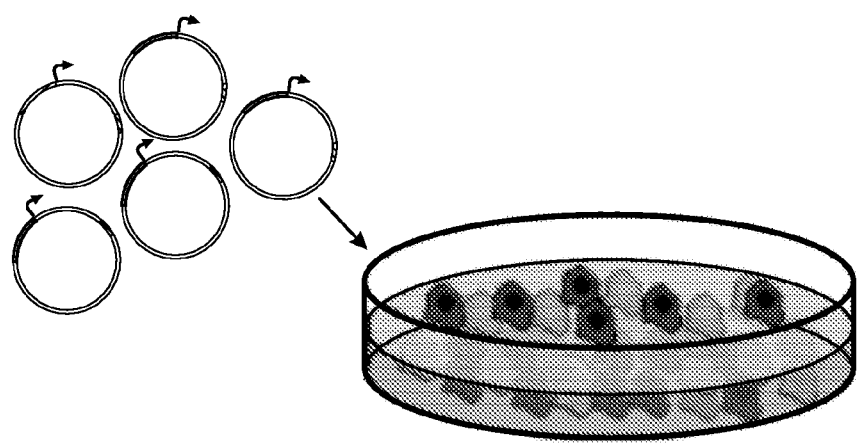
Figures 3, 15:
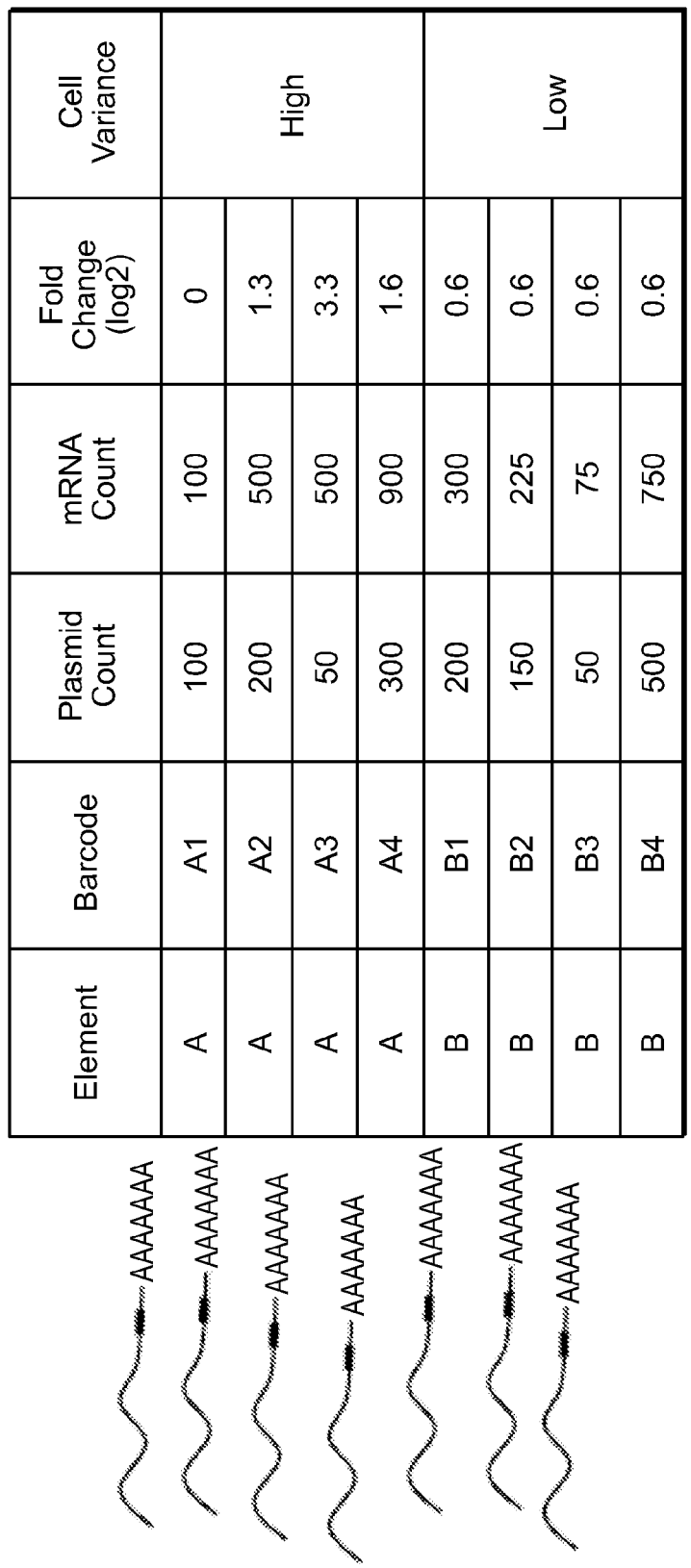

FIGS. 12-14 illustrate approaches that may be taken to identify specific regions responsible for expression activity and to determine the specific nucleotide motif influencing expression activity. FIGS. 12 and 13 show that tiling deletions across a sequence may be helpful in identifying the region having expression modulating activity. FIG. 14 suggests that saturation mutagenesis may be used to identify precise binding partners and binding motifs and to identify how all possible perturbations to the sequence may impact expression activity. FIG. 15 shows that increasing the number of barcodes used in MPRA can allow each cell to receive a unique barcode. This diversity results in the measurement of an individual barcode representing the activity within a single cell allowing sequences with cell-to-cell variance in activity to be identified.

The results described herein above were carried out using the following methods and materials.

Variant Selection

To construct the 79 k oligo library eQTLs were identified by reanalysis of the Geuvadis RNA-seq dataset of lymphoblastoid cell lines (LCLs) from individuals of European (EUR) and West African (YRI) ancestry (Supplemental Experimental Procedures). We identified 3,965 eQTLs within EUR and YRI using significance thresholds corresponding to a 0.1% false positive rate within permuted samples. Using the selection and design criteria described in the Supplemental Experimental Procedures we selected 29,173 variants to test by MPRA. After accounting for both the reference and alternate alleles, neighboring variants and in some instances orientation of the oligo relative to the promoter we designed a total of 78,956 oligos with the variant of interest centered within 150 bp of genomic sequence.

The 7.5 k oligo was constructed by selecting variants representing four different classes. (i) 425 Variants called as expression positive in the 79 k oligo experiment. (ii) Variants called as 426 expression positive and having allelic skew (emVars) in the 79 k oligo experiment. (iii) Location 427 matched controls, selected for being between 250-1000 bp of a lead eQTL association, not in LD with the lead candidate ($r2<=0.25$) and not having an appreciable eQTL signal in the Geuvadis or GTEx datasets. (iv) Randomly selected variants from across the genome matching only to the minor allele frequency spectrum of EUR eQTL variants. A subset of the randomly selected variants were further filtered for having no detectable eQTL signal in the Geuvadis and GTEx datasets. The two sets of randomly selected sites behaved similarly by MPRA and were combined as a single set during analysis.

Massively Parallel Reporter Assay

Oligos were synthesized (Agilent Technologies) as 180 bp sequences containing 150 bp of genomics sequence and 15 bp of adapter sequence on either end. Unique 20 bp barcodes were added by emulsion PCR along with additional constant sequence for subsequent incorporation into a backbone vector by gibson assembly. The oligo library was expanded by electroporation into *E. coli* and the resulting plasmid library was sequenced by Illumina 2×150 bp chemistry to acquire barcode/oligo pairings. The library underwent restriction digest and GFP with a minimal TATA promoter was inserted by gibson assembly resulting in the 150 bp oligo sequence positioned directly upstream of the promoter and the 20 bp barcode falling in the 3' UTR of GFP. After expansion within *E. coli* the final MPRA plasmid library was sequenced by Illumina 1×30 bp chemistry to acquire a baseline representation of each oligo within the library.

Libraries were electroporated into LCLs using the Neon system (Life Technologies). We performed multiple independent replicates for NA12878 (5 replicates) and NA19239 (3 replicates) with each replicate consisting of ~$5\times10^8$ cells. Transfections for 5 independent replicates of HepG2 cells were performed using Lipofectamine 3000 (Life Technologies). For both cell types RNA was harvested 24 hours post transfection followed by DNA digestion, capturing of the GFP transcripts and cDNA synthesis. Sequencing libraries were constructed by adding adapters by PCR and sequenced using Illumina 1×30 bp biochemistry. Detailed experimental conditions as well as oligo and primer sequences are provided herein below.

Allelic Replacement at PTGER4 Locus

Cas9-GFP vector, guide RNA (gRNA) targeting rs9283753, and a 150 bp homology oligo with either the reference (T) or alternate (C) allele, were transfected into $5 \times 10^6$ LCLs. 24 hours post-transfection cells were sorted for GFP expression and expanded for two week in bulk. Single cell dilutions of each bulk population were performed and after two weeks of growth genotyped using Illumina sequencing to identify mutations of interest. All clones were confirmed by Sanger sequencing. To quantify changes in expression of PTGER4 qPCR was performed on clonal colonies identified as either HDR or wild-type. RNA was collected from ~$7.5 \times 10^{\wedge}6$ cells, and cDNA was synthesized. qPCR was performed with technical triplicates for each reaction. Detailed transfection and qPCR conditions as well as gRNA, homology oligo and primer sequences are provided herein below.

Data Analysis

The sum of the barcode counts for each oligo within replicates were normalized and oligos 471 showing differential expression relative to the plasmid input were identified by modeling a negative binomial with DESeq2 and applying a threshold of 0.01 for the Bonferroni corrected p-value. For sequences that displayed regulatory activity we tested if the reference and alternate allele showed similar activity by applying a t-test on the log transformed RNA/plasmid ratios for each experimental replicates. Combining independent results from NA12878 and NA9239 using Fisher's method generated a final LCL specific call set. We used an FDR (Benjamini-Hochberg) cutoff of 5% as a threshold for calling emVars. Detailed procedures for calculating enrichments, sensitivity/specificity and concordance with established measures of regulatory activity are provided herein.

RNA Mapping

Illumina 100 bp paired-end RNA-seq reads from 446 lymphoblastoid cell lines (LCLs) sequenced by the Geuvadis consortium were downloaded from http://www.ebi.ac.uk/ena/data/view/ERP001942 (Lappalainen et al., Nature 501, 506-511 2013). Samples were mapped with Tophat v2.0.9 without coverage searching and an edit distance of 3 against human genome build 37 using Gencode v13 as a transcriptome guide (Harrow et al., Genome Research 22, 1760-1774, 2012; Kim et al., Genome Biology 14, R36, 2012). Coverage across genes were estimated with Cufflinks v2.1.1 using multi read correction and masking of rRNA and tRNA loci (Trapnell et al., Nature Biotechnology 28, 511-5152010). Fragments per kilobase of transcripts (FPKM) estimates for each gene were acquired from Cufflinks and genes were filtered for having at least one individual with an FPKM of 0.5 or greater. Expression values were log 2 transformed and normalized for both known and hidden covariates using the PEER software package (Stegle et al., PLoS Computational Biology 6, e1000770 2010). Gender, population and the sequencing laboratory for each sample were provided to PEER as known covariates and the number of unknown covariates was set to 10.

Sample Imputation

Genotypes were obtained for 420 RNA-seq samples from the phase 1 release of the 1000 genomes (1KG) project (Consortium). For the remaining 26 samples where 1KG phase1 data was not available, we obtained Illumina OMNI 2.5M, Affymatrix Axiom 5M and HapMap data. Merged genotypes for the 26 individuals were imputed against the full phase 1 collection of genotypes using IMPUTE2 with the requirement of an imputation confidence score of 0.9 or greater for keeping the imputed call. All indels greater than 35 bp were removed from subsequent analysis (Howie et al., PLoS Genetics 5, e1000529, 2009).

eQTL Calling

Genotypes were separated into three groups by population: all (1KG), Yoruba (YRI) and European (EUR) individuals, and filtered to include only variants at greater than 5% minor allele frequency within each population group. PEER residuals and genotypes were provided to matrix eQTL to calculate cis eQTLs (SNP/gene distance less than 1 Mb) using an additive linear model. To set a significance threshold we ran 1000 permutations for chromosomes 1,7,16 and 19 in each population group and calculated the p-value that corresponded to an empirical 0.1% false positive rate and used these values as significance thresholds in our eQTL analysis. This resulted in p-value cutoffs of $6.3 \times 10-11$ and $4.1 \times 10-10$ for YRI and EUR respectively (eQTL count: 471 in YRI & 3171 in EUR). For every gene with a significant snp/gene association, we performed a conditional analysis for all other SNPs within the 1 Mb window of the gene using the top associated variant as a covariate in the linear model and the same p-value thresholds used in the initial pass. We iterated through consecutive rounds of conditional analysis adding each new top associated SNP to the linear model until no other variants in the region showed a significant association with gene expression (conditional eQTL count: 315 in EUR & 8 in YRI).

SNP Selection for Reporter Assay

To select variants for testing in the 79 k reporter assay we first selected the top associated variant for each significant eQTL in both the primary and conditional eQTL analysis of EUR and YRI (3,965). Linkage disequilibrium (LD) was calculated for every top association within the discovery population and selected all variants that were in perfect LD ($r2=1$) with it (12,321 variants). In addition, for each gene significantly associated in EUR we selected the top associated variant and all variants in perfect LD within the YRI and 1KG analysis regardless of the strength of the association (12,230 variants, 4,177 redundant with prior selections).

A subset of eQTL peaks was selected to characterize comprehensively, beyond only the top associated variants. 209 eQTLs were chosen for testing of all variants having an r2 of 0.9 or greater with the most highly associated variant (9,921 variants, 1,122 redundant with prior selections). These 209 peaks were selected based on their intersection with SNPs in the NHGRI's catalog of published GWAS hits, capturing a total of 163 GWAS SNPs. To determine overlapping peaks, r2 was calculated within the 1KG EUR supergroup to top associated variants in the eQTL and GWAS analysis. Loci overlapping was called when a shared variant was within 0.8 r2 of the GWAS loci and 0.9 r2 of the eQTL peak.

To create oligonucleotides (oligos) for the 29,173 sites we centered the variant within 150 bp of flanking hg19 sequence (74 bp on the 5' and 75 bp on the 3' end for SNPs). To determine the orientation of the oligo we chose the direction of the variant relative to the transcription start site of the gene it was associated with in the eQTL analysis. If the variant was associated with multiple genes in different orientations, we designed oligos in both the forward and reverse direction. For variants within the test set where other variants fell within the 150 bp oligo, we created an additional alternative haplotype oligo testing the alternate and reference allele of the centered variant with the alternative allele(s) inserted into the flanking sequence. Finally, there were 7 variants that contained an AsiI restriction site within the flanking sequence that would cause these oligos to be lost during construction of the MPRA library. To rescue the oligos we made a single base change in the restriction site; none of these changes altered the variant site or 20 bp flanking either side. In total we designed 78,956 oligos for synthesis, testing a total of 29,173 variants.

The smaller 7.5 k oligo reporter library was constructed of 5 subsets of variants (2 positive controls and 3 negative controls). For positive controls we randomly selected 137 variants that were expression positive but emVar negative and 127 emVar positive variants from the 79 k oligo experiment. For the location matched negative controls we compiled a list of all variants with a MAF>=5%, residing 150-1000 bp away from a top eQTL association in the EUR analysis. Variants were filtered for having low LD with the lead association (<=0.25 r2) and for having no detectable signal of eQTL association in both the Geuvadis LCL dataset (p-value >=0.001) and 13 tissues from the GTEx consortium (p-value >=0.0001). If multiple variants met this criteria at any one loci, only a single site was selected at random for testing. For the randomly selected control variants we picked 2700 sites at random from the EUR population matching the allele frequency distribution of lead variants in the primary EUR eQTL analysis. For 1200 of the 2700 variants we set an additional criteria on requiring eQTL signal in LCLs and GTEx at the same thresholds as the location matched controls. Downstream analysis suggested not differences between the two randomly selected control sets prompting us to combine all 2700 sites together as a single set. All sites were tested in the forward orientation with the flanking sequence taken from hg19. There were 572 additional variants designed on the assay that were unrelated to the positive and control sets that were discarded from the primary analysis.

Massively Parallel Reporter Assay
Oligo Synthesis

Oligos were synthesized by Agilent Technologies as 180 bp sequences containing 150 bp of genomic context and 15 bp of adapter sequence at either end (5'ACTGGCCGCTTGACG[150 bp oligo]CACTGCGGCTCCTGC3') (FIG. 1A). Post synthesis (FIG. 1B), 20 bp barcodes and additional adapter sequences were added by performing 28 emulsion PCR reactions each 50 µL in volume containing 1.86 ng of oligo, 25 µL of Q5 NEBNext MasterMix (NEB, M0541S), 1 unit Q5 HotStart polymerase (NEB, M0493S), 0.5 uM MPRA_v3_F and MPRA_v3_20I_R primers and 2 ng BSA (NEB, B9000). PCR master mix was emulsified by vortexing with 220 µL Tegosoft (Evonik), 60 µL ABIL WE (Evonik) and 20 µL Mineral Oil (Sigma, M5904) per 50 µL PCR reaction at 4° C. for 5 min. 100 µL of Emulsion mixture was plated per well across a 96 well plate and cycled with the following conditions; 95° C. for 30 sec, 15 cycles of (95° C. for 20 sec, 60° C. for 10 sec, 72° C. for 15 sec), 72° C. for 5 min. Amplified emulsion mixture was broken and purified by adding 1 mL of 2-butanol (VWR, AA43315-AK), 50 µL of AMPure XP SPRI (Beckman Coulter, A63881) and 80 µL of binding buffer (2.5M NaCl, 20% PEG-8000) per 350 µL of Emulsion mix and vigorously vortexing followed by incubation for 10 minutes at room temperature. Broken emulsion/butanol mixture was spun at 2900 rcf for 5 min and the butanol phase was discarded. The aqueous phase was placed on a magnetic rack for 20 minutes prior to aspiration. Remaining beads were washed once with 2-butanol, three times with 80% EtOH and eluted in EB (Qiagen, 19086).

MPRA Vector Assembly

To create our mpraΔorf library (FIG. 1C), barcoded oligos were inserted into sfiI digested pGL4:23:ΔxbaΔluc by gibson assembly (NEB, E2611) using 1.1 µg of oligos and 1 of digested vector in a 40 µL reaction incubated for 60 min at 50° C. followed by SPRI purification and elution in 20 µL of EB. Half of the ligated vector was then transformed into 100 µL of 10-beta E. coli (NEB, C3020K) by electroporation (2 kV, 200 ohm, 25 Electroporated bacteria were immediately split into eight 1 mL aliquots of SOC (NEB, B9020S) and recovered or 1 hour at 37° C. then independently expanded in 20 mL of LB supplemented with 100 µg/mL of carbenicillin (EMD, 69101-3) on a floor shaker at 37° C. for 6.5 hours. After outgrowth aliquots were pooled prior to plasmid purification (Qiagen, 12963). For each of the aliquots we plated serial dilutions after SOC recovery and estimated a library size of >108 CFUs.

To create our final mpra:gfp library (FIG. 1D), 20 µg of mpra:Δorf plasmid was linearized with 200 units of AsiSI (NEB, R0630) and 1× cutsmart buffer (NEB) in a 500 µL volume for 3.5 hours at 37° C. An amplicon containing a minimal promoter, GFP open reading frame and a partial 3' UTR was then inserted by gibson assembly using 10 µg of AsiSI linearized mpraΔorf plasmid, 33 µg of the GFP amplicon in 400 µL of total volume for 90 minutes at 50° C. followed by a 1.5× beads/sample SPRI purification. The total recovered volume was digested a second time to remove remaining uncut vectors by incubation with 50 U of AsiSI, 5 U of RecBCD (NEB, M0345), 10 µg BSA, 1 mM ATP, 1×NEB Buffer 4 in a 100 µL reaction for 6 hours at 37 C followed by SPRI purification and elution with 55 µL of EB.

To generate transfection ready MPRA libraries 10 µL of mpra:gfp plasmid was electroporated (2 kV, 200 ohm, 25 µF) into 220 µL of 10-beta cells. Electroporated bacteria was split across 6 tubes and each recovered in 2 mL of SOC for 1 hour at 37° C. then added to 500 mL of LB with 100 µg/mL of carbenicillin and grown for 9 hours at 37° C. prior to plasmid purification (Qiagen, 12991). We repeated this same electroporation protocol 3 additional times, each time with an estimated transformation efficiency of >108 cfu. All plasmid preps were then pooled and normalized to 1 µg/uL to generate our final mpra:gfp library used in all subsequent transfections.

MPRA Transfections

Lymphoblastoid cells were grown in RPMI (Life Technologies, 61870) supplemented with 15% FBS (Life Technologies, 26140) maintaining a cell density of 2-10×105 cells per mL. For all 8 transfections (5×NA12878 and 3×NA19239) cells were grown to a density of ~1×106 cells/mL prior to the removal of 5×108 cells. Cells were collected by centrifugation at 120×g and eluted in 4 mL of RPMI with 500 µg of mpra:gfp library. Electroporation was performed in 100 µL volumes with the Neon transfection system (Life Technologies) applying 3 pulses of 1200 V for 20 ms each. Using separate control transfections we achieved transfection efficiencies of 40-60% for all replicates. Cells were allowed to recover in 180 mL in RPMI with 15% FBS for 24 hours then collected by centrifugation, washed once with PBS, collected and frozen at −80° C. (FIG. 1E).

Hepatocytes were grown in MEM alpha (Life Technologies, 32561) supplemented with 10% FBS. Cells were plated across ten 15 cm cell culture plates and grown to 60-70% cell density. On the day of transfection media was replaced with 30 mL fresh MEM/FBS followed by transfection with 87.5 µL of Lipofectamine 3000 (Life Technologies, L3000015) and 35 µg of DNA using the manufacturer's protocol. Cells were incubated with transfection reagents for 24 hours, then washed with 15 mL of PBS followed by dissociation with 0.05% trypsin-EDTA (Life Technologies, 25300), centrifugation, PBS wash and a final collection at 300×g prior to storage at −80° C.

RNA Extraction and cDNA Synthesis

Total RNA was extracted from cells using Qiagen Maxi RNeasy (Qiagen, 75162) following the manufacturer's protocol including the on-column DNase digestion. A second DNase treatment was performed on the purified RNA using 5 µL of Turbo DNase (Life Technologies, AM2238) in 750 µL of total volume for 1 hour at 37° C. The digestion was stopped with the addition of 7.5 µL 10% SDS and 75 µL of 0.5M EDTA followed by a 5 minute incubation at 70° C. The total reaction was then used for pulldown of GFP mRNA. Water was added to the DNase digested RNA to bring the total volume to 898 µL to which 900 µL of 20×SSC (Life Technologies, 15557-044), 1800 µL of Formamide (Life Technologies, AM9342) and 2 µL of 100 uM biotin-labeled GFP probe (GFP_BiotinCapture_1-3, Table S3) were added and incubated for 2.5 hours at 65° C. Biotin probes were captured using 400 µL of pre-washed Streptavidin beads (Life Technologies, 65001) eluted in 500 µL of 20×SSC. The hybridized RNA/probe bead mixture was agitated on a nutator at room temperature for 15 minutes. Beads were captured by magnet and washed once with 1×SSC and twice with 0.1×SSC. Elution of RNA was performed by the addition of 25 µL water and heating of the water/bead mixture for 2 minutes at 70° C. followed by immediate collection of eluent on a magnet. A second elution was performed by incubating the beads with an additional 25 µL of water at 80° C. A final DNase treatment was performed in 50 µL total volume using 1 µL of Turbo DNase incubated for 60 minutes at 37° C. followed by inactivation with 1 µL of 10% SDS and purification using RNA clean SPRI beads (Beckman Coulter, A63987).

First-strand cDNA was synthesized from half of the DNase-treated GFP mRNA with SuperScript III and a primer specific to the 3' UTR (MPRA_v3_Amp2Sc_R) using the manufacturer's recommended protocol, modifying the total reaction volume to 40 µL and performing the elongation step at 47° C. for 80 minutes. Single-stranded cDNA was purified by SPRI and eluted in 30 µL EB.

Tag-Seq Library Construction

To minimize amplification bias during the creation of cDNA tag sequencing libraries, samples were amplified by qPCR to estimate relative concentrations of GFP cDNA using 1 ÂµL of sample in a 10 ÂµL PCR reaction containing 5 ÂµL Q5 NEBNext master mix, 1.7 ÂµL Sybr green I diluted 1:10,000 (Life Technologies, S-7567) and 0.5 uM of TruSeq_Universal_Adapter and MPRA_Illumina_GFP_F primers (Table S3). Samples were amplified with the following conditions: 95Â° C. for 20 seconds, 40 cycles (95Â° C. for 20 sec, 65Â° C. for 20 sec, 72Â° C. for 30 sec), 72Â° C. for 2 min. All LCL cDNA samples had a cycle threshold of approximately 11 while HepG2s showed an earlier cycle threshold corresponding to the larger amount of RNA recovered. To add Illumina sequencing adapters, cDNA samples and 5 mpra:gfp plasmid controls were diluted to match the replicate with the lowest concentration and 10 ÂµL of normalized sample was amplified using the reaction conditions from the qPCR scaled to 50 ul, excluding Sybrgreen I and using only 10 amplification cycles. Amplified cDNA was SPRI purified and eluted in 40 ÂµL of EB. Individual sequencing barcodes were added to each sample by amplifying the entire 40 ÂµL elution in a 100 ÂµL Q5 NEBNext reaction with 0.5 uM of TruSeq_Universal_Adapter primer and a reverse primer containing a unique 8 bp index (Illumina_Multiplex) for sample demultiplexing post-sequencing. Samples were amplified at 95Â° C. for 20 seconds, 6 cycles (95Â° C. for 20 sec, 64Â° C. for 30 sec, 72Â° C. for 30 sec), 72Â° C. for 2 minutes. Indexed libraries were SPRI purified and pooled according to molar estimates from Agilent TapeStation quantifications. Samples were sequenced using 1×30 bp chemistry on an Illumina HiSeq through the Broad Institute's walk-up sequencing service.

To determine oligo/barcode combinations within the mpra pool, Illumina libraries were prepared from the mpraΔorf plasmid library by performing 4 separate amplifications with 200 ng of plasmid in a 100 µL Q5 NEBNext PCR reaction containing 0.5 uM of TruSeq_Universal_Adapter and MPRA_v3_TruSeq_Amp2Sa_F primers with the following conditions: 95° C. for 20 sec, 6 cycles (95° C. for 20 sec, 62° C. for 15 sec, 72° C. for 30 sec), 72° C. for 2 minutes. Amplified material was SPRI purified using a 0.6× bead/sample ratio and eluted with 30 µL of EB. Sequencing indexes were then attached using 20 µL of the eluted product and the same reaction conditions as for the tag-seq except the number of enrichment cycles were lowered to 5. Samples were molar pooled and sequenced using 2×150 bp chemistry on Illumina HiSeq and NextSeq instruments through the Broad Institute's walk-up sequencing service.

7.5 k Oligo MPRA Experiment

To perform the MPRA experiment of the 7.5 k library we adjust the experimental conditions to 1/10th the scale used for the 79 k library with the following exceptions. The two gibson assembly steps were performed at ¼ scale of the original library and RNA extraction was performed using Qiagen Midi RNeasy (Qiagen, 75142) followed by ½ scale reactions for the GFP pulldown and cDNA synthesis. Library preparation was performed as described above but diluting the samples to the cycle threshold specific for the 7.5 k library.

Single Oligo Validation

To validate the expression values obtained by MPRA we selected 29 oligos consisting of 13 ref/alt pairs and 3 additional oligos. We selected the oligos based upon their association with an eQTL/GWAS peak while maintaining diverse representation of regulatory strength. Two of the oligos were selected as no-expression controls for having uncorrected p-values of greater than 0.01. We designed the same 150 bp sequence that was tested by MPRA as a gBlock (IDT) and cloned each into the pGL4.23 firefly luciferase reporter vector (Promega, E8411). We initially performed a standard luciferase reporter assay, co-transfecting 1×106 LCLs (NA12878) with 1 ug of the cloned firefly luciferase vector and 200 ng of a renilla luciferase control vector (pGL4.74, Promega, E6921) and recovered for 24 hour in a 96 well plate. We performed three separate experimental replicates each with two transfection replicates per experiment for a total of six replicates per oligo. Firefly luciferase luminescence for each well was normalized to the renilla luciferase luminescence for the same well and each experiment was normalized as a log-ratio value relative to the mean of the two no-expression control oligos.

Initial analysis of the luciferase expression strength to the MPRA expression values showed moderate correlation for a portion of the oligos but also displayed discordant values for many sites. Under the hypothesis that some oligos carry novel transcription start sites causing out of frame transcription of the luciferase loci, we performed qPCR as the end point for the luciferase assay instead of luminescence. Using the same transfection protocol as the luciferase assay, we performed two transfection replicates for each oligo and extracted mRNA 24 hours post transfection using the MagMAX 96 Total RNA isolation kit (Life Technologies, AM1830). DNA was digested by incubation with 2 U of Turbo DNase for 60 minutes followed by RNA SPRI purification. qPCR was performed in replicate according to the manufacturer's recommendations on the purified RNA using 1-step Sybr-to-Ct and gene-specific qPCR primers (Fluc_F/Fluc_R or Rluc_F/Rluc_R) to measure both the firefly and renilla luciferase RNA levels, with pGL4.23 and pGL4.74 plasmids serving as standards for copy number calculations. For each replicate a firefly/renilla ratio was calculated as well as a log-ratio value relative to the mean of the 2 negative control samples.

Data Analysis

Barcode/Oligo Reconstruction

Paired-end 150 bp reads from the sequencing of the mpraΔorf library were merged into single amplicons using Flash v1.2.7 (flags: –r 150, –f 220, –s 10) (Magoč and Salzberg, 2011). Amplicon sequences were kept if the 5' adapter matched with a levenshtein distance of 3 or less and 2 bp at the edges of both the 5' and internal constant sequences matched perfectly. Oligo sequences from the passing reads were then mapped back to the expected oligo sequences using BWA mem version 0.7.9a (flags: –L 100 –k 8 –O 5) (Li, 2013). Alignment scores were calculated as matching bases divided by the expected oligo size and reads with alignment scores of less than 0.95 were discarded. Remaining oligo/barcode pairs were then merged and barcodes attributable to multiple oligo sequences were marked as conflicting and removed from further analysis. In total we observed 90.2 million unique barcodes in the sequencing data.

Identification of Regulatory Oligos

Reads from the tag sequencing were filtered for the inclusion of the constant sequence within the GFP 3' UTR. Specifically, a levenshtein distance of 4 or less was required within the constant sequence at the end of the tag-seq read with the two bases directly adjacent to the barcode (base 21 & 22) required to match perfectly. Barcodes were then matched with oligo sequences determined through sequencing of the mpraΔorf library and the sum of all barcodes counts within each of the 78,956 oligos were calculated.

Oligo counts from all 18 samples (5 plasmid controls, 5 NA12878, 3 NA19239 and 5 HepG2) were passed into DESeq2 and a median-of-ratios method was used to normalize samples for varying sequencing depths (Love et al., Genome Biology 15, 550, 2013). Normalized read counts of each oligo were then modeled by DESeq2 as a negative binomial distribution (NB). DESeq2 estimates variance for each NB by pooling all oligo counts across samples and fitting a trend line to model the relationship between oligo counts and observed dispersion. It then applies an empirical Bayes shrinkage by taking the observed relationship as a prior and performing a maximum a posteriori estimate of the dispersion for each oligo. The overall result is that DESeq2 can obtain an estimate for dispersion of each oligo with greatly reduced bias by pooling information from all oligos.

We then used DESeq2 to estimate the fold change estimation between the control condition (plasmid) and each of the three experimental conditions (NA12878, NA19239, and HepG2). Again, DESeq2 applies a Bayesian shrinkage on the log ratios to prevent false positive results at the extreme ends of expression (low and high count oligos). We use Wald's test to estimate significance for expression differences between conditions and corrected for multiple hypothesis testing by Bonferroni's method accounting for 39,479 tests. We required a corrected p-value of 0.01 or less in either the reference or alternate allele in order to call a sequence as having a regulatory effect on expression (FIG. 9A-9F).

Identification of Expression-Modulating Variants

Figure 10B:
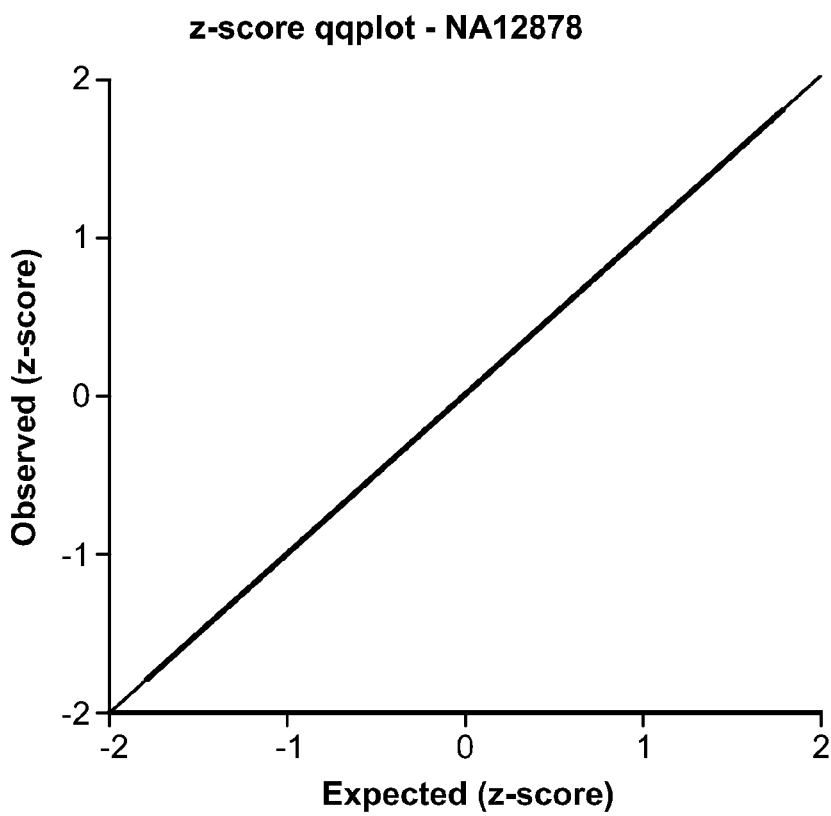
Figure 10C:
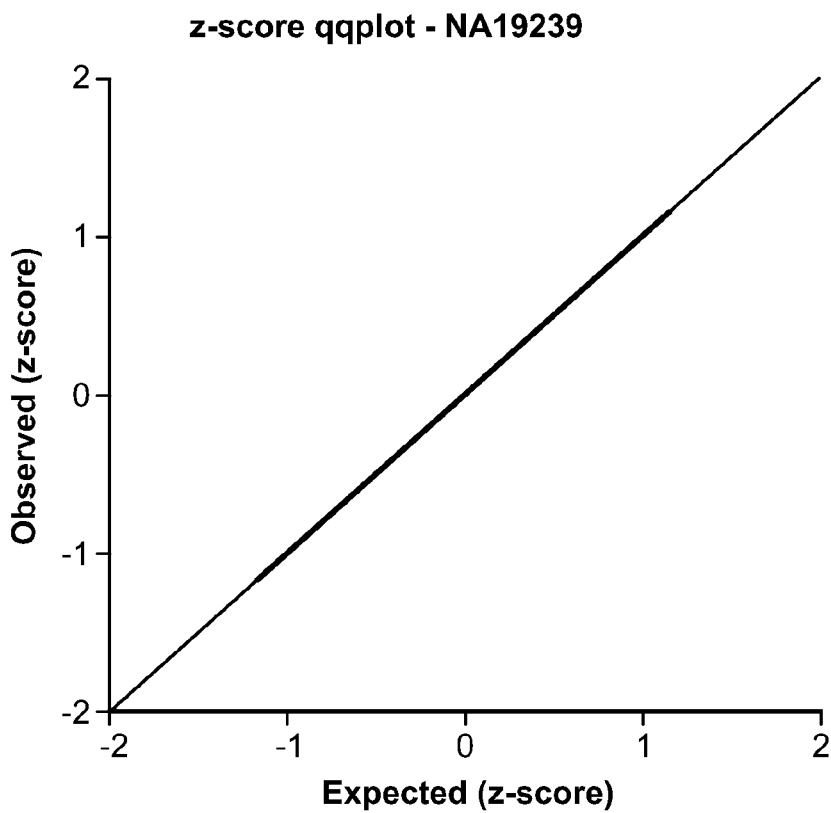
Figure 11A:
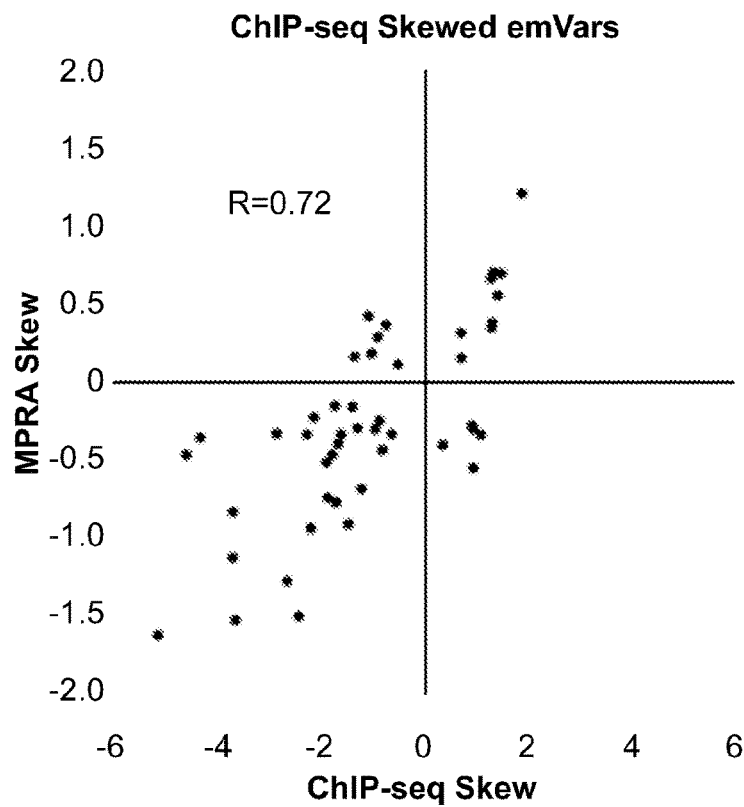
Figure 11B:
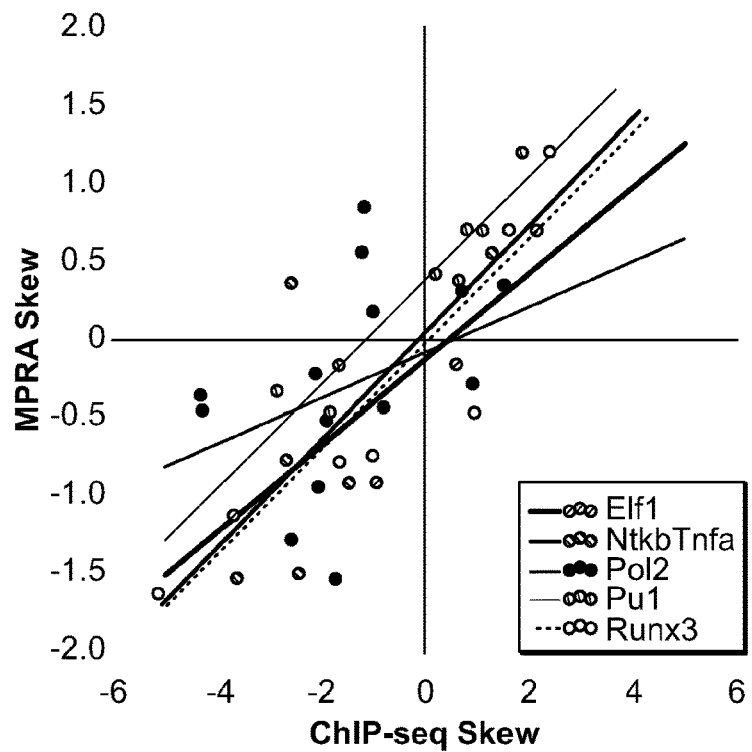
FIG. 11B is a graph similar to (A) but with points labeled by the transcription factor showing allelic skew. Points are only plotted for TFs with detectable allelic skew at 3 or more emVars. emVars overlapping more than one TF are plotted as multiple points. A simple linear regress ion line for each transcription factor is plotted through the points.
Figure 11C:
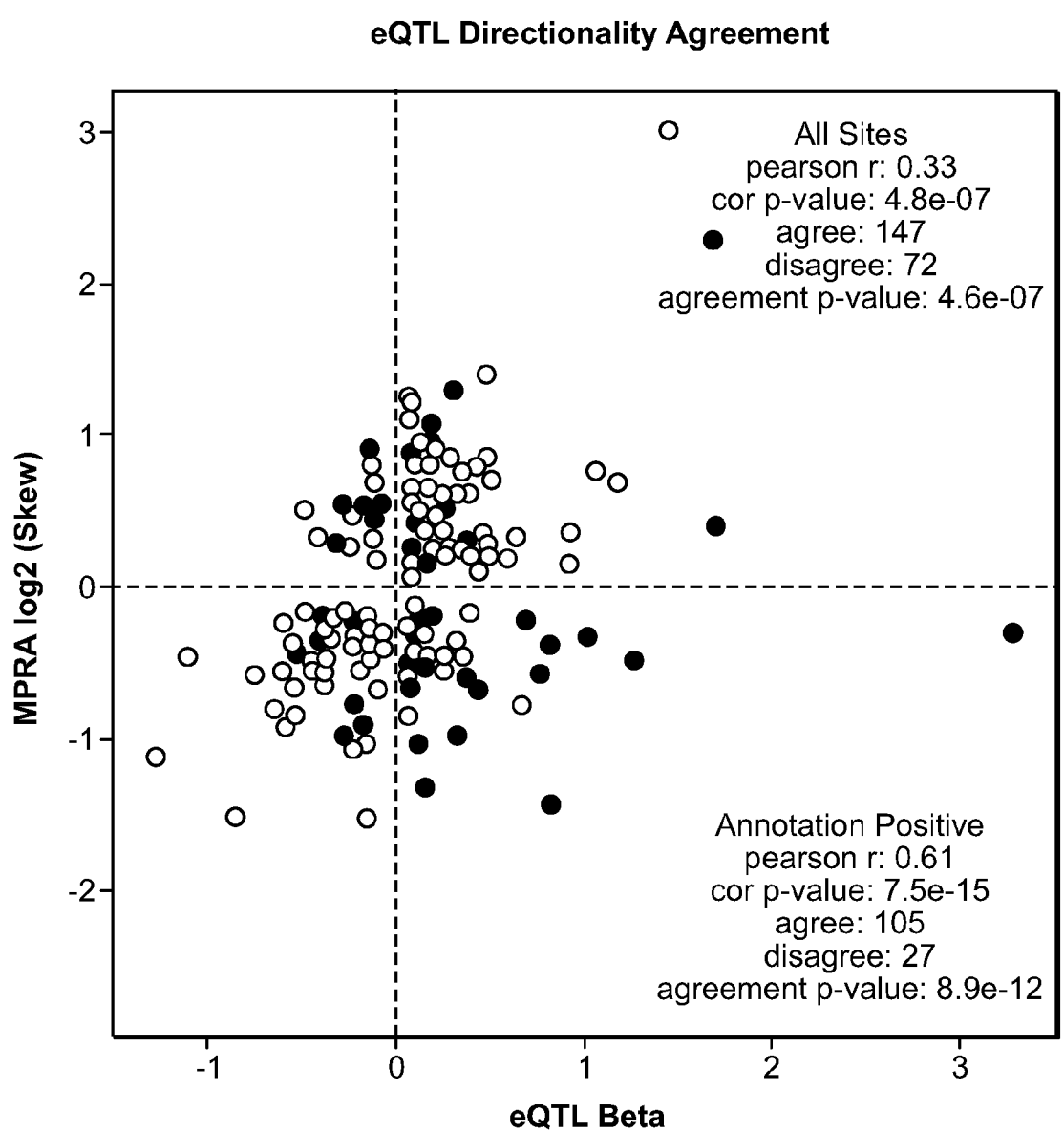
FIG. 11C is a graph showing shared directionality between MPRA and eQTL results. MPRA skew (y-axis) plotted against beta values from the EUR eQTL analysis. Variants with significant associations to multiple genes in the eQTL analysis were discarded if all genes failed to share directionality. Green points denote annotation positive emVars, annotation negative sites are plotted as grey points.

For the identification of variants altering expression strength we considered only variants originating from sequences determined to have a regulatory effect. We calculated p-values for allelic skew by comparing the log ratios of the reference and alternate alleles using a paired t-test with independent estimation of variance and Welch's adjustment to the degrees of freedom. This test assumes normality; to evaluate normality, we calculated z-scores for the differences of the log ratios for all 39,479 ref/alt pairs and observed a distribution very similar to that expected from sampling ratios from a normal distribution (FIG. 10A-10C). We further validated our approach by evaluating the qq plot for variants that failed to show regulatory effects (uncorrected expression p-value >0.01), which are not expected to have any allelic bias (FIG. 11A-11C). To collapse results from the two LCL experiments, we averaged both the expression ratio and allelic skew weighted by the number of replicates from each sample; p-values were combined using Fisher's method. For all samples as well as the combined LCL analysis FDR was calculated for the skew p-value using the Benjamini-Hochberg procedure.

Downsampling and Analysis of the 7.5 k Oligo Library

Figure 7A:
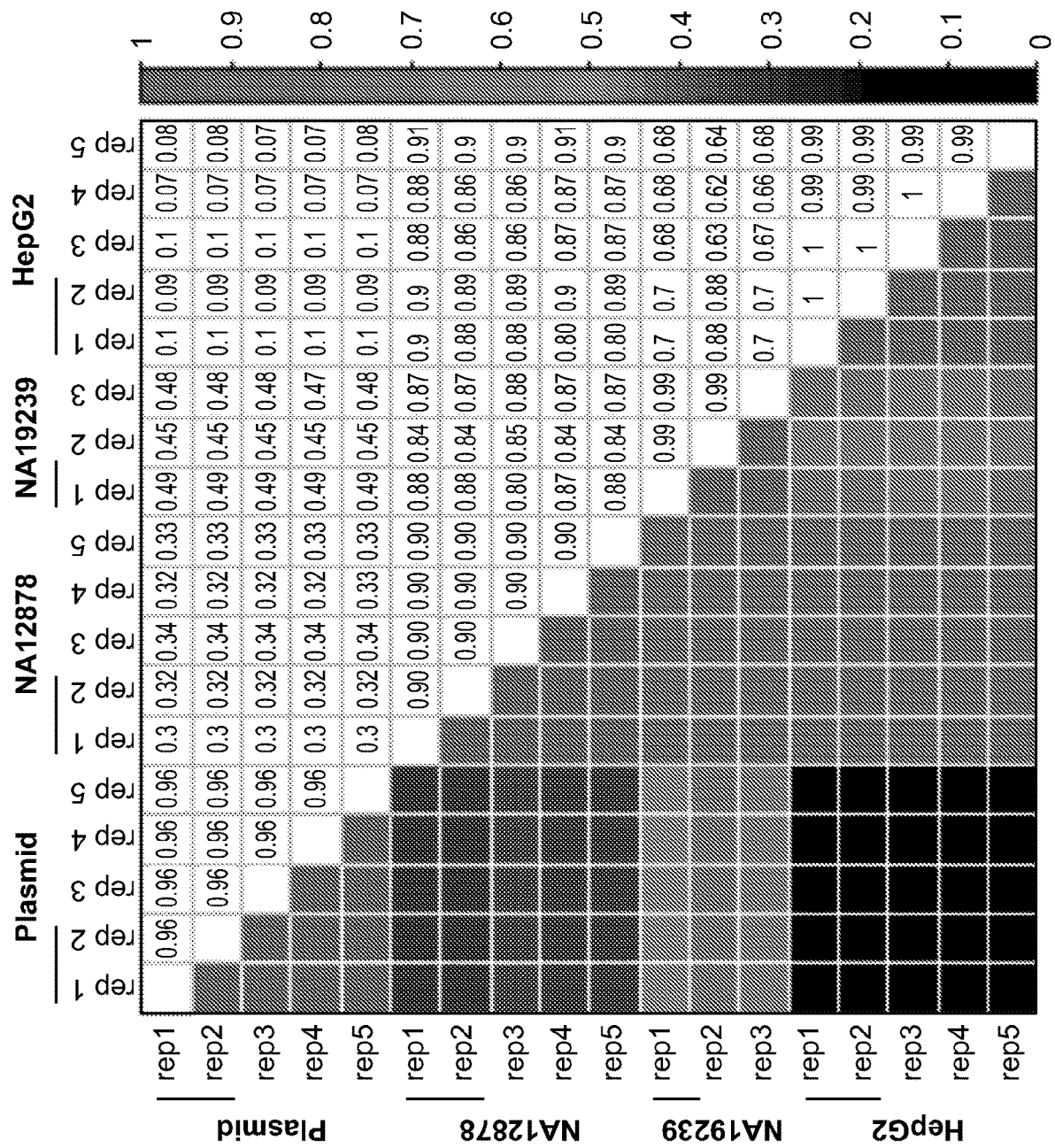
FIGS. 7A and 7B are correlation matrices of normalized read counts.
Figure 7B:
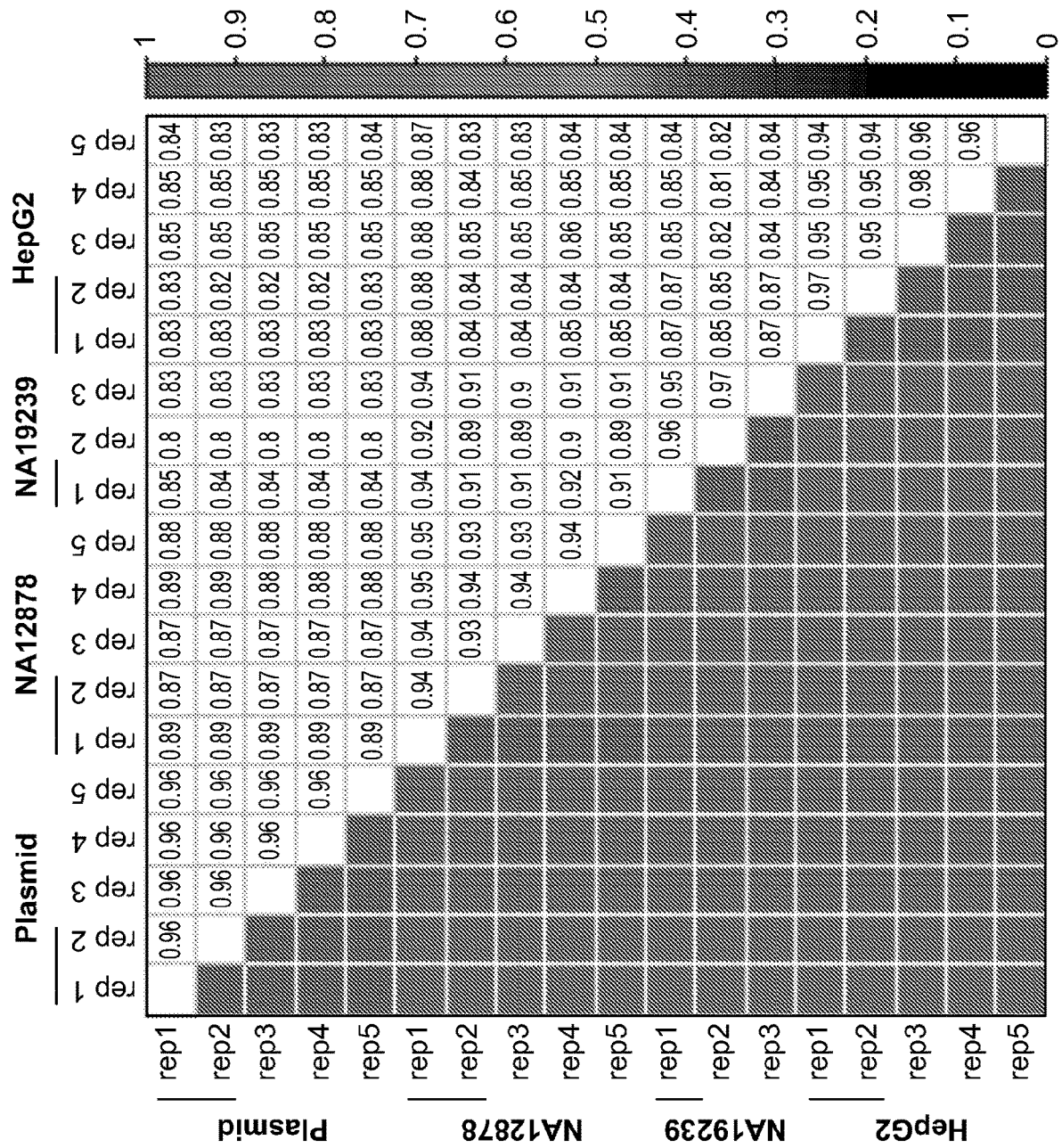

Analysis of the 7.5 k oligo MPRA experiment was performed as described for the initial 79 k library applying FDR cutoffs for expression and skew calling that matched those originally used with the 79 k library. Initial analysis of the full dataset showed the smaller library had greater power to detect weaker expression changes than the original library due to a 2.5-14 fold increase in the median number of barcodes tagging each oligo (FIGS. 7A and 7B). As expected from our previous observation of the effect of barcodes, we detected lower dispersion in the 7.5 k oligo pool as estimated by DESeq2. Therefore, to better match the two libraries, we downsampled the 7.5 k dataset to match the median number of barcodes representing each oligo in the 79 k pool while maintaining the rank and distribution for each 7.5 k experimental replicate. Specifically, we paired replicates between the two pools, calculated the ratio of the median number of barcodes per oligo in the old to its pair in the new, and sampled without replacement that proportion of the original number of barcodes for each oligo. We applied this to each replicate and repeated 500 times, each time calculating summary statistics including the number of expression positive variants and the number of emVars per subsampling. In the text, we report the mean of these 500 experiments.

This procedure caused both the dispersion and raw counts to better reflect the 79 k experiment. After downsampling, we saw no loss in our ability to call both expression and emVar positive controls included in the new library compared to the full dataset with 96% of expression variants and 72% of emVars detected (96% and 71% detected in the full dataset). In addition, Correlation was strong between predicted expression effects between the two experiments. We note that despite extensive downsampling, the dispersion was still lower for the 7.5 k library than in the 79 k library. As a result, it is probable that the 7.5 k library still maintains a slightly higher sensitivity to detect expression effects than the original 79 k library resulting in conservative false positive estimates. This conclusion is supported by the lower effect size of expression positive sites detected in all three negative control sets relative to the 264 expression positive controls.

Annotations Used for Enrichment Analysis

For enrichment analysis we downloaded narrowPeak files from the ENCODE project's FTP server. All enrichment analysis for regulatory oligos required an overlap of 1 bp or greater with an annotation at any position along the oligo.

For analysis using LCL DHS regions, unless otherwise specified we took the union of all LCL regions from UW, Duke and the Unified analysis. For the annotation positive designation we required the oligo to be overlap 2 of the following 4 categories; all TF-ChIP data (including POL), LCL DHS regions, CAGE regions for NA12878 (Nucleus, Cytosol and Cell) and chromatin marks (H3 k27ac,H2A.Z, H3K4me2,H3K4me3,H3K9ac). All fold enrichments are reported as odds-ratios unless otherwise stated.

For enrichments involving promoter proximity we defined transcription start sites (TSS) by analyzing the predicted transcript abundance within our mapped RNA-seq reads. Using the cufflinks generated estimation of transcript abundance we identified genes with an average FPKM of 0.5 or greater across all LCLs and selected TSSs from transcripts within 50% of the most abundant transcript's FPKM. We counted an overlap with the core promoter when the variant fell within 100 bp upstream and 50 bp downstream of the TSS. A hypergeometric test was used to evaluate significance of all emVars relative to either the proportion promoter sites in all 29 k variants tested or genome wide (all variants >=5% minor allele frequency in EUR). For strongly linked GWAS associated eQTL peaks (>=0.9 r2) we first tested enrichment of promoter emVars relative to all other emVars falling outside these peaks. Significance was calculated by Fisher's exact test splitting all variants into two categories; those strongly linked to a GWAS SNP (r2 of 0.9 or greater) and all non-gwas associated variants, and testing the number of emVars falling in a promoter compared to the total number of promoter variants. To verify our analysis is not confounded by the differences in how the variants were selected (variants with an r2 of 0.9 or greater to an eQTL peak compared to perfect LD) we performed the same analysis but using only the GWAS eQTL peaks. We split these variants into two groups based on the maximum LD value to a GWAS SNP. Using 0.9 r2 as a cutoff we then used Fisher's exact test to calculate significance of enrichment with promoter sites.

Transcription Factor Binding Sites

We used FIMO and HOCOMOCO v9 to calculate binding scores for the reference and alternative allele in all 29 k oligos (Grant et al., Bioinformatics (Oxford, England) 27, 1017-1018, 2011; Kulakovskiy et al., Nucleic Acids Research 41, D195-2022012). We identified SNPs and indels where the motif had a binding p-value of 1×10-5 or less and the predicted TF showed binding in the analogous ENCODE ChIP-seq experiments. From this list we calculated the difference in binding score between the reference and alternate allele for each TF predicted to bind. Where sites had multiple predicted binding partners we selected the TF with the greatest change between the alleles. We binned the variants based on the allele difference score and calculated the proportion these variants represented within the three classes of function (emVars, regulatory/non emVar, not significant).

Sensitivity Estimates

For the majority of eQTL peaks, only the top associated variant (and variants in perfect LD) were tested by MPRA. Therefore, an emVar may not be detected for a given eQTL peak for one of two reasons:
(1) The causal variant was not among the top associated variants for the eQTL peak and so was not tested (2) The causal variant was tested but the MPRA assay gave a false negative These two reasons for failure to detect an emVar in an eQTL peak correspond to two distinct sensitivity estimates, a technical sensitivity (2 alone), and the power of the study design to detect a causal variant (1 and 2 together). To estimate the power of experimental design, we first estimated the number of true positive emVars in EUR and YRI peak independently.

$$TP=(V)-N^*(1-\text{specificity})$$

Where V is the number of variants identified by the MPRA as emVars, N is the total number of variants tested across the peaks and a specificity of 99.04%. We then simulated the number of eQTL peaks explained within EUR and YRI when selecting the specified number of emVars (TP) randomly from the list of MPRA+ variants.

To estimate the MPRA's technical sensitivity, we first note that the probability of the causal variant being among those with the maximum r2 in the peak should increase with the difference in the variance explained ($\Delta r2$) between the top associated variant (and variants in perfect LD) and the second best association for each eQTL peak. To quantify this relationship, we fit a logistic regression to model the effect of a peak's $\Delta r2$ and the effect size of the top associated SNP (ES) on the probability of detecting an emVar in that peak. Specifically, we fit the following regression:

$$\text{Log it}(P(\text{emVar}))=\beta 2\ \ln(\Delta r2)+\beta 1|ES|+\beta 0$$

The regression was fit using the statsmodels toolbox in Python 3.3 (https://github.com/statsmodels/statsmodels). The natural log-transformation was used to capture the expected convexity of the covariates. Using this model, we estimated the technical sensitivity as a function only of effect size alone by setting â†r2=1, corresponding to the maximum possible separation between the top and second to top variant.

Detection of Allelic Skew in DHS and ChIP-Seq Data

Detecting allelic skew in DHS and ChIP-seq datasets is challenging because mapping of short reads produces a bias toward the reference allele, confounding measurements of skew. To circumvent this problem, we constructed personal reference genomes for the maternal and paternal haplotype of each of the lymphoblastoid cell lines for which we had DHS or ChIP-seq data using the software vcf2diploid (Rozowsky et al., Molecular Systems Biology 7, 522, 2010). We then aligned DHS or ChIP-seq data to the corresponding personal reference genomes using BWA aln/samse with the default parameters (Li and Durbin, Bioinformatics (Oxford, England) 25, 1754-1760, 2009). We then filtered out aligned reads with a mapping quality of 0 and obtained the set of reads overlapping heterozygous genomic variant using bedtools (Quinlan and Hall, Bioinformatics (Oxford, England) 26, 841-842, 2010). Finally, we obtained allele counts for reads overlapping each variant by counting the reads that mapped only to the maternal or paternal reference, or that mapped with a better alignment score to one reference than the other. Alignment scores were calculated as a −1 penalty per mismatched base and a −1 penalty for each base-pair difference of an indel. Reads with an equivalent alignment score when aligned to the maternal and paternal reference were discarded.

For calculating skew in DHS, allele counts were pooled across all replicates and all LCLs that were heterozygous for a given variant. All variants with a pooled-coverage greater than 20 with a count of at least 1 for each allele were scored for DHS skew. A p-value cutoff of 0.1 was used. For particular figures, a coverage cutoff of 10 and a p-value cutoff of 0.1 was used. In addition, variants that showed a substantial fraction of poorly mapped reads for one allele but not the other were discarded.

Figure 10D:
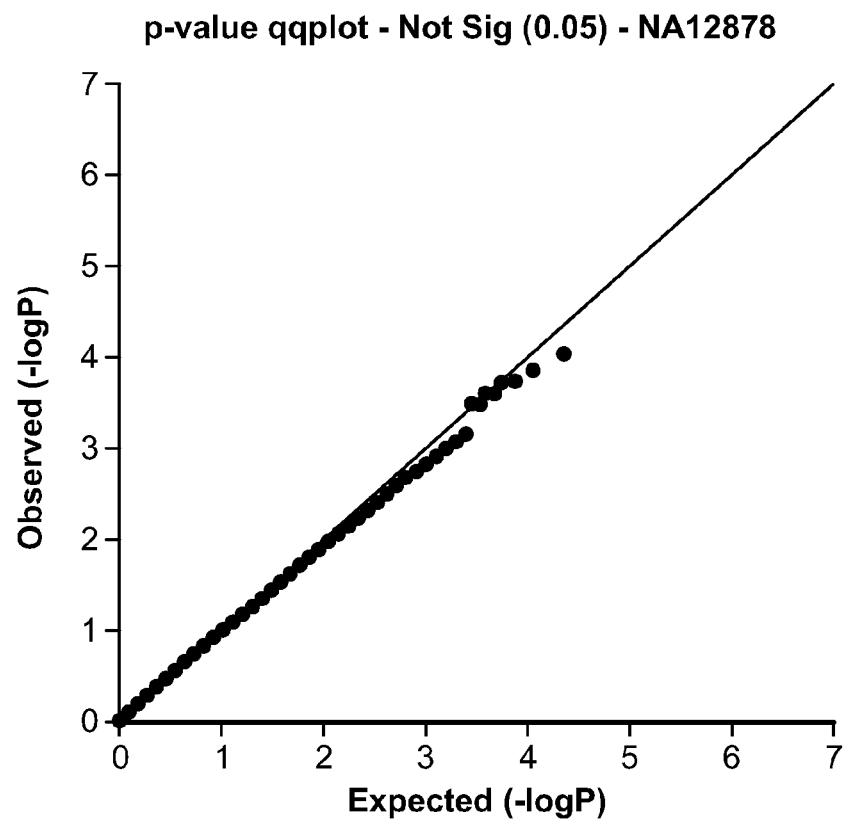
Figure 10E:
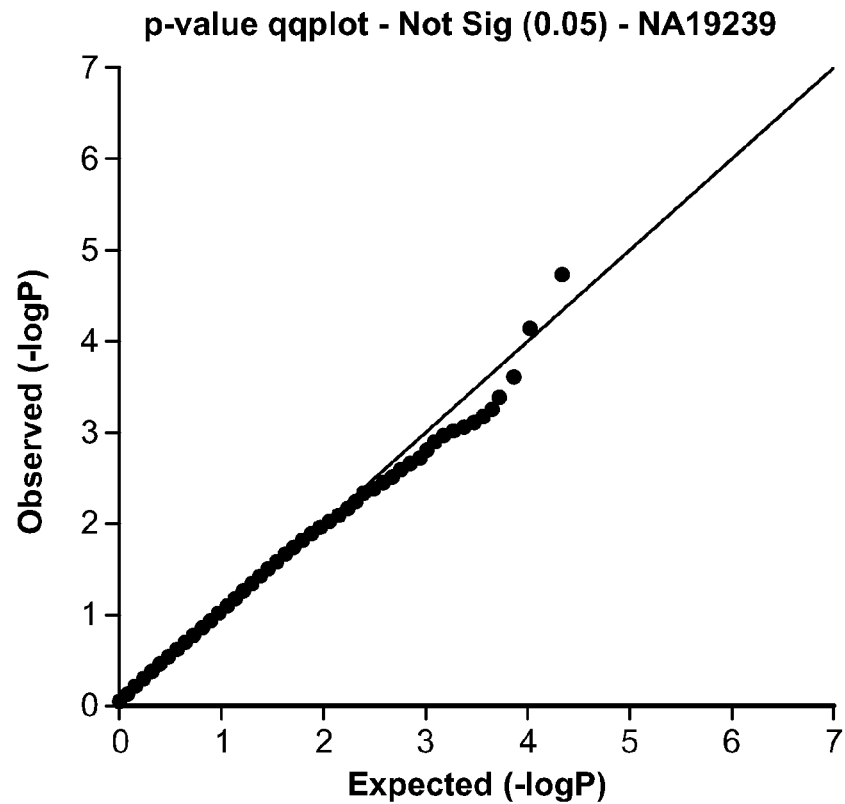

For calculating skew in transcription factor binding, allele counts were pooled across all LCL replicates for samples that were heterozygous for a given variant. All variants with a pooled-coverage greater than 20 for a transcription factor with a count of at least 1 for each allele were scored for TF skew. A p-value cutoff of 0.001 was used for calculating enrichment as well as for certain figures. See FIGS. 10D and 10E.

Allelic Replacement of rs9283753

We performed CRISPR editing in LCL to alter the rs9283753 SNP at PTGER4. We used a modified version of the pX458 cas9 vector with U6:gRNA and F1 ori removed and delivered the gRNA as a 455 bp dsDNA amplicon. A guide sequence was designed that overlapped rs9283753 at positive 6 of the gRNA (Table S3). Two versions of the guide were created changing only position 6 to match the variant to be edited. Off-target cutting was assessed by in silico mapping with no appreciable off-target sites identified. Homology repair templates were synthesized as 150 bp PAGE purified Ultramer oligonucleotides (IDT) with a phosphorothioate bind at the predicted cutting location of cas9 (Table S3). We used two cell lines for allelic replacement; NA12878 which is homozygous for the ancestral allele (alt, T) and NA11831 which is homozygous for the derived (ref, C). We electroporated 5×106 cells with 4 ug of cas9 vector, 400 ng of gRNA and 500 nM of the homology vector using the Neon system. Cells were sorted 24 hours post-transfection for GFP expression using a MoFlo Astrios EQ Cell Sorter (Beckman Coulter) at the Harvard University Bauer Core Facility.

Clonal populations of edited cells were isolated by single-cell dilution into 384-well plates. Genotypes of the clones were determined by Illumina sequencing of a the genomic regions surrounding the SNP using primers rs9283753_ILMN_F and rs9283753_ILMN_R (Table S3). Cell lysate were obtained for successful clonal populations after two weeks of growth by lysing 100 ul of cells in 100 ul of lysis buffer (100 mM KCl, 2 mM EDTA, 20 mM Tris-HCl, 2% Triton-X 100, 2% TWEEN 20, 0.08 U/ul proteinase K) at 55 C for 60 minutes followed by 95 C for 10 minutes. PCR was performed on an aliquot of the lysate using Q5 Hot Start Master Mix (NEB). After amplification of the genomic region, each clonal amplicon had unique indices for sequencing added by PCR. Amplicons were sequenced on a MiSeq (Illumina) with 2×150 bp reads. Clones that showed the edited genotypes after analysis were confirmed by Sanger sequencing.

To quantify changes in expression of the PTGER4 gene after CRISPR editing, we performed qPCR comparing edited cells to wild-type cells that had undergone the same cas9/clonal expansion process. Cells were seeded at 2.5×105 cells/mL 24 hours prior to RNA isolation. For RNA isolation, 7.5×105 cells were collected and RNA was isolated with the MagMAX-96 Total RNA Isolation Kit (Life Technologies) according to manufacturer's instructions. cDNA for each sample was produced from 1 ug of isolated RNA using the SuperScript III First Strand Synthesis System (Life Technologies). qPCR were performed with PowerUp SYBR Green Master Mix (Life Technologies), 10 ng of cDNA, and forward and reverse primers at 500 nM each in a total volume of 10 ul. Technical triplicates were performed for each reaction. For each edited cell line two biological (independent seedings) were performed, for the negative control samples (wild-type) 4 and 3 independent clonal populations were tested for NA12878 and NA11831 respectively. Expression values for two separate primer pairs for PTGER4 were averaged together and normalized using the ΔΔCt method using PPIA and TBP as references.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of identifying a nucleic acid expression-modulating variant, the method comprising
introducing into a population of cells a plurality of expression vectors comprising a candidate nucleic acid expression-modulating variant, an open reading frame (ORF), and an identifying randomized nucleic acid tag, wherein the ORF and the randomized nucleic acid tag are each expressed;
detecting expression of the randomized nucleic acid tag; and
comparing expression of the randomized nucleic acid tag with a reference level of expression, wherein detection of an alteration in expression identifies the candidate nucleic acid expression-modulating variant as a nucleic acid expression-modulating variant,
wherein the variant is a risk allele for ankylosing spondylitis.

2. The method of claim 1, wherein the expression is compared with two control sets, wherein the first set comprises regulatory sequence variants selected randomly from the genome, and a second set comprises regulatory sequence variants near but not associated with eQTL variants.

3. The method of claim 1, wherein the method identifies genetic elements that regulate gene expression.

4. The method of claim 1, wherein each candidate nucleic acid expression-modulating variant is tagged with at least about 10-100, 100 200, or 300 500 unique randomized identifying sequences.

5. The method of claim 1, wherein the method captures the unique randomized identifying sequence by hybridization.

6. The method of claim 1, wherein the expression vectors are transfected into lymphoblastoid cell lines or hepatocarcinoma cell lines.

7. The method of claim 1, wherein the method detects the over or under expression of the unique randomized identifying sequence.

8. The method of claim 1, wherein the method further comprises calculating the proportion of sequences that overlap open chromatin, as identified by DNase hypersensitivity sites (DHS).

9. The method of claim 1, wherein the method identifies a distal enhancer.

10. The method of claim 9, wherein the distal enhancer is the emVar rs9283753.

11. The method of claim 9, wherein the distal enhancer regulates expression of the prostaglandin E receptor 4 (PT-GER4).

12. The method of claim 1, wherein the method provides for the concurrent evaluation of at least about 10,000 to 100,000 variants.

13. The method of claim 1, wherein the method provides for the concurrent evaluation of at least about 30,000 to 300,000 variants.

14. The method of claim 1, wherein each candidate nucleic acid expression-modulating variant is tagged with at least about 100-200 unique randomized identifying sequences.

15. The method of claim 1, wherein each candidate nucleic acid expression-modulating variant is tagged with at least about 300-500 unique randomized identifying sequences.

* * * * *